US012643956B2

(12) United States Patent　　(10) Patent No.:　US 12,643,956 B2

Durrant et al.　　(45) Date of Patent:　Jun. 2, 2026

(54) BINDING MEMBERS

(71) Applicant: Scancell Limited, Oxford (GB)

(72) Inventors: Linda Gillian Durrant, Oxford (GB);
Mireille Vankemmelbeke, Oxford (GB); Tina Rose Parsons, Oxford (GB)

(73) Assignee: Scancell Limited, Oxford (GB)

( * ) Notice: Subject to any disclaimer, the term of this patent is extended or adjusted under 35 U.S.C. 154(b) by 162 days.

(21) Appl. No.: 17/631,002

(22) PCT Filed: Jul. 31, 2020

(86) PCT No.: PCT/EP2020/071725

§ 371 (c)(1),
(2) Date: Jan. 28, 2022

(87) PCT Pub. No.: WO2021/019095

PCT Pub. Date: Feb. 4, 2021

(65) Prior Publication Data

US 2022/0267465 A1　　Aug. 25, 2022

(30) Foreign Application Priority Data

Jul. 31, 2019　(GB) ...................................... 1910899

(51) Int. Cl.
C07K 16/30 (2006.01)
A61K 39/00 (2006.01)
A61P 35/00 (2006.01)

(52) U.S. Cl.
CPC .......... C07K 16/3076 (2013.01); A61P 35/00 (2018.01); C07K 16/3046 (2013.01); A61K 2039/505 (2013.01); C07K 2317/24 (2013.01); C07K 2317/33 (2013.01); C07K 2317/567 (2013.01); C07K 2317/732 (2013.01); C07K 2317/734 (2013.01); C07K 2317/77 (2013.01); C07K 2317/92 (2013.01); C07K 2317/94 (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,544,545 A | 10/1985 | Ryan et al. | |
| 2006/0002942 A1 * | 1/2006 | Kunz ...................... | A61P 43/00 530/391.1 |
| 2017/0101481 A1 * | 4/2017 | Holmes .................. | C07K 16/44 |

FOREIGN PATENT DOCUMENTS

| | | | | |
|---|---|---|---|---|
| DE | 3218121 A1 | 11/1983 | | |
| EP | 0125023 A1 | 11/1984 | | |
| EP | 0120694 A3 | 7/1985 | | |
| EP | 0058481 B1 | 10/1986 | | |
| EP | 0142541 B1 | 7/1987 | | |
| EP | 0239400 A2 | 9/1987 | | |
| EP | 0528767 A1 | 2/1993 | | |
| EP | 0285059 B1 | 11/1994 | | |
| GB | 2188638 A | 10/1987 | | |
| JP | H06153955 A | * 6/1994 | | |
| KR | 2013020393 A | * 2/2013 | ......... | H04L 63/0884 |
| WO | 9201047 A1 | 1/1992 | | |
| WO | 9311161 A1 | 6/1993 | | |
| WO | 9413804 A1 | 6/1994 | | |
| WO | 9524484 A1 | 9/1995 | | |
| WO | 9613594 A1 | 5/1996 | | |
| WO | 02092126 A1 | 11/2002 | | |
| WO | WO-03093317 A1 | * 11/2003 | ............. | A61P 37/00 |
| WO | 2008034181 A1 | 3/2008 | | |
| WO | WO-2012148003 A1 | * 11/2012 | ............. | A61P 43/00 |

OTHER PUBLICATIONS

Durrant et al. Immunology in the clinic review series; focus on cancer: glycolipids as targets for tumour immunotherapy. Clinical and Experimental Immunology, 167: 206â215. (Year: 2012).*

Sela-Culang et al. The structural basis of antibody-antigen recognition. Fron. Immuno., vol. 4, Article 302, Oct. 2013. (Year: 2013).*

Herold et al. Determinants of the assembly and function of antibody variable domains. Nature Scientific Reports, 7:12276, Sep. 25, 2017. (Year: 2017).*

Merriam-Webster. Prevent Definition. website saved Apr. 24, 2025. (Year: 2025).*

ACS. Cancer Risk and Prevention. website saved Mar. 21, 2025. (Year: 2025).*

Holliger, P., et al., ""Diabodies:" small bivalent and bispecific antibody fragments", PNAS USA, 90(14), 6444-6448, 1993.

Traunecker, A., et al., "Bispecific single chain molecules (Janusins) target cytotoxic lymphocytes on HIV infected cells", EMBO J., 10(12), 3655-3659, 1991.

Office Action for EP Application No. 20756785.0, mailed Jan. 20, 2025.

Search Report for GB19108992, mailed Jan. 14, 2020.

Co, M. S. et al., "Humanized Anti-Lewis Y Antibodies: In Vitro Properties and Pharmacokinetics In Rhesus Monkeys", Cancer Research, American Association For Cancer Research, 56(5), Mar. 1, 1996, 1118-1125.

(Continued)

*Primary Examiner* — Julie Wu

*Assistant Examiner* — Amy M. Chattin

(74) *Attorney, Agent, or Firm* — Elmore Patent Law Group, P.C.; Mahreen Chaudhry Hoda; Carolyn S. Elmore

(57) ABSTRACT

The present invention relates to specific binding members, such as antibodies and fragments thereof, that are capable of specifically binding a Lewis Y (Le$^y$) carbohydrate. It also relates to the use of such binding members in medicine and to nucleic acids encoding such binding members.

15 Claims, 42 Drawing Sheets

Figure 1C:
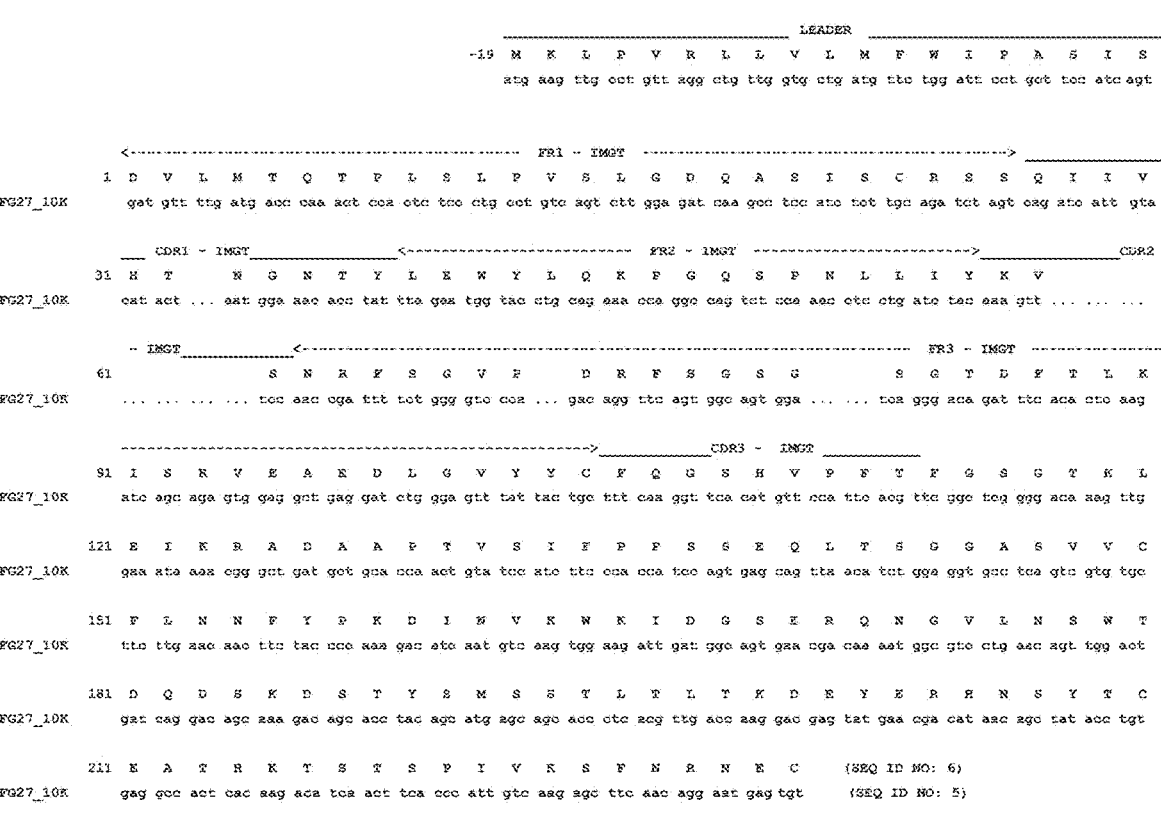

Specification includes a Sequence Listing.

(56)           References Cited

OTHER PUBLICATIONS

Scott, A. M. et al., "Construction, production, and characterization of humanized anti-Lewis Y monoclonal antibody 3S193 for targeted immunotherapy of solid tumors", Cancer Research, American Association For Cancer Research, 60(12), Jun. 15, 2000, 3254-3261.
Smaletz, O. et al., "A phase II trial with anti-Lewis-Y monoclonal antibody (hu3S193) for the treatment of platinum resistant/refractory ovarian, fallopian tube and primary peritoneal carcinoma", Gynecologic Oncology, 138(2), DOI: 10.1016/J.YGYNO.2015.05.023, 272-277.

* cited by examiner

Figure 1a

```
                                                          LEADER
----------------------------------------------------------                _____
                                          atg aac ttc tgg ctc agc ttg att ttc ctt gtc ctt gtt tta aaa ggt gtc cag tgt
                                     -19  M   N   F   W   L   S   L   I   F   L   V   L   V   L   K   G   V   Q   C <---------------------------------------- FR1 - IMGT ---------------------------------------->  _____
        1   E   V   K   L   V   E   S   G   G       G   L   V   Q   P   G   G   S   L   K   L   S   C   A   T   S   G   F   T   F
FG27_10H    gaa gtg aag ctg gtg gag tct ggg gga ... ggc tta gtg cag cct gga ggg tcc ctg aaa ctc tcc tgt gca acc tct gga ttc act ttc ____ CDR1 - IMGT_____<------------------------ FR2 - IMGT ------------------------>_____CDR2
        31                      S   H   Y   Y   M   Y   W   V   R   Q   T   P   E   K   R   L   E   W   V   A   Y   I   S   N   D
FG27_10H    ... ... ... ...     agt cac tat tac atg tat tgg gtt cgc cag act cca gag aag agg ctg gag tgg gtc gca tac att agt aat gat ...

- IMGT_____<------------------------------------------------------------------- FR3 - IMGT ----------------
        61           G   D   N   T   Y   Y   P   D   T   I   R       G   R   F   T   I   S   R   D   N   A   R   N   T   L   Y   L   Q
FG27_10H    ... ggt gat aac acc tat tat cca gac act ata agg ... ggc cga ttc acc atc tcc aga gac aat gcc agg aac acc ctg tac ctg caa ------------------------------------------------->_____CDR3 - IMGT_____
        91  M   S   R   L   K   S   E   D   T   A   M   Y   Y   C   A   R   G   K   Y   D   G   A   W   F   A   Y   W   G   Q   G
FG27_10H    atg agc cgt ctg aag tct gag gac aca gcc atg tat tac tgt gca aga ggg aag tac gac ggg gcc tgg ttt gct tac tgg ggc caa ggg 121 T   L   V   T   V   S   A   A   T   T   T   A   P   S   V   Y   P   L   V   P   G   C   S   D   T   S   G   S   S   V
FG27_10H    act ctg gtc act gtc tct gca gct aca aca aca gcc cca tct gtc tat ccc ttg gtc cct ggc tgc agt gac aca tct gga tcc tcg gtg 151 T   L   G   C   L   V   K   G   Y   F   P   E   P   V   T   V   K   W   N   Y   G   A   L   S   S   G   V   R   T   V
FG27_10H    aca ctg gga tgc ctt gtc aaa ggc tac ttc cct gag ccg gta act gta aaa tgg aac tat gga gcc ctg tcc agc ggt gtg cgc aca gtc 181 S   S   V   L   Q   S   G   F   Y   S   L   S   S   L   V   T   V   P   S   S   T   W   P   S   Q   T   V   I   C   N
FG27_10H    tca tct gtc ctg cag tct ggg ttc tat tcc ctc agc agc ttg gtg act gta ccc tcc agc acc tgg ccc agc cag act gtc atc tgc aac 211 V   A   R   P   A   S   K   T   E   L   I   K   R   I   E   P   R   I   P   K   P   S   T   P   P   G   S   S   C   P
FG27_10H    gta gcc cgc cca gcc agc aag act gag ttg atc aag aga atc gag cct aga ata ccc aag ccc agt acc ccc cca ggt tct tca tgc cca 241 P   G   N   I   L   G   G   P   S   V   F   I   F   P   P   K   P   K   D   A   L   M   I   S   L   T   P   K   V   T
FG27_10H    cct ggt aac atc ttg ggt gga cca tcc gtc ttc atc ttc ccc cca aag ccc aag gat gca ctc atg atc tcc cta acc ccc aag gtt acg 271 C   V   V   V   D   V   S   E   D   D   P   D   V   R   V   S   W   F   V   D   N   K   E   V   R   T   A   W   T   Q
FG27_10H    tgt gtg gtg gtg gat gtg agc gag gat gac cca gat gtc cgt gtc agc tgg ttt gtg gac aac aaa gaa gta cac aca gcc tgg aca cag 301 P   R   E   A   Q   Y   N   S   T   F   R   V   V   S   A   L   P   I   Q   H   Q   D   W   M   R   G   K   E   F   K
FG27_10H    ccc cgt gaa gct cag tac aac agt acc ttc cga gtg gtc agt gcc ctc ccc atc cag cac cag gac tgg atg agg ggc aag gag ttc aaa 331 C   K   V   N   N   K   A   L   P   A   P   I   E   R   T   I   S   K   P   K   G   R   A   Q   T   P   Q   V   Y   T
FG27_10H    tgc aag gtc aac aac aaa gcc ctc cca gcc ccc atc gag aga acc atc tca aaa ccc aaa gga aga gcc cag aca cct caa gta tac acc 361 I   P   P   P   R   E   Q   M   S   K   E   K   V   S   L   T   C   L   V   T   N   F   F   S   E   A   I   S   V   E
FG27_10H    ata ccc cca cct cgt gaa caa atg tcc aag aag aag gtt agt ctg acc tgc ctg gtc acc aac ttc ttc tct gaa gcc atc agt gtg gag 391 W   E   R   N   G   E   L   E   Q   D   Y   K   N   T   P   P   I   L   D   S   D   G   T   Y   F   L   Y   S   K   L
FG27_10H    tgg gaa agg aac gga gaa ctg gag cag gat tac aag aac act cca ccc atc ctg gac tca gat ggg acc tac ttc ctc tac agc aag ctc 421 T   V   D   T   D   S   W   L   Q   G   E   I   F   T   C   S   V   V   H   E   A   L   H   N   H   H   T   Q   K   N
FG27_10H    act gtg gat aca gac agt tgg ttg cag gga gaa att ttt acc tgc tcc gtg gtg cat gag gct ctc cat aac cac cac aca cag aag aac 451 L   S   R   S   P   G   K       (SEQ ID NO: 24)
FG27_10H    ctg tct agc tcc cct ggt aaa       (SEQ ID NO: 23)
```

Figure 1b

```
                                                    LEADER
                       atg aac ttc tgg ctc agc ttg att ttc ctt gtc ctt gtt tta aaa ggt gtc cag tgt
                   -19  M   N   F   W   L   S   L   I   F   L   V   L   V   L   K   G   V   Q   C <----------------------------------- FR1 - IMGT ----------------------------------->
          1  E   V   K   L   V   E   S   G   G       G   L   V   Q   P   G   G   S   L   K   L   S   C   A   T   S   G   F   T   F
FG27_18H     gaa gtg aag ctg gtg gag tct ggg gga ... ggc tta gtg cag cct gga ggg tcc ctg aaa ctc tcc tgt gca acc tct gga ttc act ttc _____ CDR1 - IMGT_____<----------------------- FR2 - IMGT ----------------------->_____CDR2
         31              S   H   Y   Y   M   Y   W   V   R   Q   T   P   E   K   R   L   E   W   V   A   Y   I   S   N   D
FG27_18H     ... .. ... .. agt cac tat tac atg tat tgg gtt cgc cag act cca gag aag agg ctg gag tgg gtc gca tac att agt aat gat ...

- IMGT_____<------------------------------------------------------------ FR3 - IMGT ----------------
         61          G   D   N   T   Y   Y   P   D   T   I   R       G   R   F   T   I   S   R   D   N   A   R   N   T   L   Y   L   Q
FG27_18H     ... ggt gat aac acc tat tat cca gac act ata agg ... ggc cga ttc acc atc tcc aga gac aat gcc agg aac acc ctg tac ctg caa ----------------------------------->_____CDR3 - IMGT _____
         91  M   S   R   L   K   S   E   D   T   A   N   Y   Y   C   A   R   G   K   Y   D   G   A   W   F   A   Y   W   G   Q   G
FG27_18H     atg agc cgt ctg aag tct gag gac aca gcc atg tat tac tgt gca aga ggg aag tac gac ggg gcc tgg ttt gct tac tgg ggc caa ggg 121  T   L   V   T   V   S   A   A   K   T   T   P   P   S   V   Y   P   L   A   P   G   S   A   A   Q   T   N   S   M   V
FG27_18H     act ctg gtc act gtc tct gca gcc aaa acg aca ccc cca tct gtc tat cca ctg gcc cct gga tct gct gcc caa act aac tcc atg gtg 151  T   L   G   C   L   V   K   G   Y   F   P   E   P   V   T   V   T   W   N   S   G   S   L   S   S   G   V   H   T   F
FG27_18H     acc ctg gga tgc ctg gtc aag ggc tat ttc cct gag cca gtg aca gtg acc tgg aac tct gga tcc ctg tcc agc ggt gtg cac acc ttc 181  P   A   V   L   E   S   D   L   Y   T   L   S   S   S   V   T   V   P   S   S   P   R   P   S   E   T   V   T   C   N
FG27_18H     cca gct gtc ctg gag tct gac ctc tac act ctg agc agc tca gtg act gtc ccc tcc agc cct cgg ccc agc gag acc gtc acc tgc aac 211  V   A   H   P   A   S   S   T   K   V   D   K   I   V   P   R   D   C   G   C   K   P   C   I   C   T   V   P   E
FG27_18H     gtt gcc cac ccg gcc agc agc acc aag gtg gac aag aaa att gtg ccc agg gat tgt ggt tgt aag cct tgc ata tgt aca gtc cca gaa 241  V   S   S   V   F   I   F   P   P   K   P   K   D   V   L   T   I   T   L   T   P   K   V   T   C   V   V   V   D   I
FG27_18H     gta tca tct gtc ttc atc ttc ccc cca aag ccc aag gat gtg ctc acc att act ctg act cct aag gtc acg tgt gtt gtg gta gac atc 271  S   K   D   D   P   E   V   Q   F   S   W   F   V   D   D   V   E   V   H   T   A   Q   T   Q   P   R   E   E   Q   F
FG27_18H     agc aag gat gat ccc gag gtc cag ttc agc tgg ttt gta gat gat gtg gag gtg cac aca gct cag acg caa ccc cgg gag gag cag ttc 301  N   S   T   F   R   S   V   S   E   L   P   I   M   H   Q   D   W   L   N   G   K   E   F   K   C   R   V   N   S   A
FG27_18H     aac agc act ttc cgc tca gtc agt gaa ctt ccc atc atg cac cag gac tgg ctc aat ggc aag gag ttc aaa tgc agg gtc aac agt gca 331  A   F   P   A   P   I   E   K   T   I   S   K   T   K   G   R   P   K   A   P   Q   V   Y   T   I   P   P   P   K   E
FG27_18H     gct ttc cct gcc ccc atc gag aaa acc atc tcc aaa acc aaa ggc aga ccg aag gct cca cag gtg tac acc att cca cct ccc aag gag 361  Q   M   A   K   D   K   V   S   L   T   C   M   I   T   D   F   F   P   E   D   I   T   V   E   W   Q   W   N   G   Q
FG27_18H     cag atg gcc aag gat aaa gtc agt ctg acc tgc atg ata aca gac ttc ttc cct gaa gac att act gtg gag tgg cag tgg aat ggg cag 391  P   A   E   N   Y   K   N   T   Q   P   I   M   N   T   N   G   S   Y   F   V   Y   S   K   L   N   V   Q   K   S   N
FG27_18H     cca gcg gag aac tac aag aac act cag ccc atc atg aac acg aat ggc tct tac ttc gtc tac agc aag ctc aat gtg cag aag agc aac 421  W   E   A   G   N   T   F   T   C   S   V   L   H   E   G   L   H   N   H   H   T   E   K   S   L   S   H   S   P   G
FG27_18H     tgg gag gca gga aat act ttc acc tgc tct gtg tta cat gag ggc ctg cac aac cac cat act gag aag agc ctc tcc cac tct cct ggt 451  K       (SEQ ID NO: 25)
FG27_18H     Aaa     (SEQ ID NO: 3)
```

Figure 2a

```
                                     _____ LEADER _____
                                     atg aac ttc tgg ctc agc ttg att ttc ctt gtc ctt gtt tta aaa ggt gtc cag tgt
                                     -19  M   N   F   W   L   S   L   I   F   L   V   L   V   L   K   G   V   Q   C <---------------------------------------- FR1 - IMGT ------------------------------------------>  _____
            1  E   V   K   L   V   E   S   G   G       G   L   V   Q   P   G   G   S   L   K   L   S   C   A   T   S   G   F   T   F
Ch27_10H    gaa gtg aag ctg gtg gag tct ggg gga ... ggc tta gtg cag cct gga ggg tcc ctg aaa ctc tcc tgt gca acc tct gga ttc act ttc ____ CDR1 - IMGT_____<------------------------------ FR2 - IMGT ------------------------------->_____CDR2
           31                          S   R   Y   Y   M   Y   W   V   R   Q   T   P   E   K   R   L   E   W   V   A   Y   I   S   N   D
Ch27_10H    ... ... ... ... agt cac tat tac atg tat tgg gtt cgc cag act cca gag aag agg ctg gag tgg gtc gca tac att agt aat gat ...

- IMGT_____<----------------------------------------------------------- FR3 - IMGT ------------------
           61       G   D   N   T   Y   Y   P   D   T   Y   R       G   R   F   T   I   S   R   D   N   A   R   N   T   L   Y   L   Q
Ch27_10H    ... ggt gat aac acc tat tat cca gac act ata agg ... ggc cga ttc acc atc tcc aga gac aat gcc agg aac acc ctg tac ctg caa ---------------------------------------------------------->_____CDR3 - IMGT _____
           91  M   S   R   L   K   S   E   D   T   A   M   Y   Y   C   A   R   G   K   Y   D   G   A   W   F   A   Y   W   G   Q   G
Ch27_10H    atg agc cgt ctg aag tct gag gac aca gcc atg tat tac tgt gca aga ggg aag tac gac ggg gcc tgg ttt gct tac tgg ggc caa ggg 121  T   L   V   T   V   S  [ S   A ] S   T   K   G   P   S   V   F   P   L   A   P   S   S   K   S   T   S   G   G   T   A
Ch27_10H    act ctg gtc act gtc tct agc gct tcc acc aag ggc cca tcg gtc ttc ccc ctg gca ccc tcc tcc aag agc acc tct ggg ggc aca gcg 151  A   L   G   C   L   V   K   D   Y   F   P   E   P   V   T   V   S   W   N   S   G   A   L   T   S   G   V   H   T   F
Ch27_10H    gcc ctg ggc tgc ctg gtc aag gac tac ttc ccc gaa ccg gtg acg gtg tcg tgg aac tca ggc gcc ctg acc agc ggc gtg cac acc ttc 181  P   A   V   L   Q   S   S   G   L   Y   S   L   S   S   V   V   T   V   P   S   S   S   L   G   T   Q   T   Y   I   C
Ch27_10H    ccg gct gtc cta cag tcc tca gga ctc tac tcc ctc agc agc gtg gtg acc gtg ccc tcc agc agc ttg ggc acc cag acc tac atc tgc 211  N   V   N   H   K   P   S   N   T   K   V   D   K   K   V   E   P   K   S   C   D   K   T   H   T   C   P   P   C   P
Ch27_10H    aac gtg aat cac aag ccc agc aac acc aag gtg gac aag aaa gtt gag ccc aaa tct tgt gac aaa act cac aca tgc cca ccg tgc cca 241  A   P   E   L   L   G   G   P   S   V   F   L   F   P   P   K   P   K   D   T   L   M   I   S   R   T   P   E   V   T
Ch27_10H    gca cct gaa ctc ctg ggg gga ccg tca gtc ttc ctc ttc ccc cca aaa ccc aag gac acc ctc atg atc tcc cgg acc cct gag gtc aca 271  C   V   V   V   D   V   S   H   E   D   P   E   V   K   F   N   W   Y   V   D   G   V   E   V   H   N   A   K   T   K
Ch27_10H    tgc gtg gtg gtg gac gtg agc cac gaa gac cct gag gtc aag ttc aac tgg tac gtg gac ggc gtg gag gtg cat aat gcc aag aca aag 301  P   R   E   E   Q   Y   N   S   T   Y   R   V   V   S   V   L   T   V   L   H   Q   D   W   L   N   G   K   E   Y   K
Ch27_10H    ccg cgg gag gag cag tac aac agc acg tac cgt gtg gtc agc gtc ctc acc gtc ctg cac cag gac tgg ctg aat ggc aag gag tac aag 331  C   K   V   S   N   K   A   L   P   A   P   I   E   K   T   I   S   K   A   K   G   Q   P   R   E   P   Q   V   Y   T
Ch27_10H    tgc aag gtc tcc aac aaa gcc ctc cca gcc ccc atc gag aaa acc atc tcc aaa gcc aaa ggg cag ccc cga gaa cca cag gtg tac acc 361  L   P   P   S   R   D   E   L   T   K   N   Q   V   S   L   T   C   L   V   K   G   F   Y   P   S   D   I   A   V   E
Ch27_10H    ctg ccc cca tcc cgg gat gag ctg acc aag aac cag gtc agc ctg acc tgc ctg gtc aaa ggc ttc tat ccc agc gac atc gcc gtg gag 391  W   E   S   N   G   Q   P   E   N   N   Y   K   T   T   P   P   V   L   D   S   D   G   S   F   F   L   Y   S   K   L
Ch27_10H    tgg gag agc aat ggg cag ccg gag aac aac tac aag acc acg cct ccc gtg ctg gac tcc gac ggc tcc ttc ttc ctc tac agc aag ctc 421  T   V   D   K   S   R   W   Q   Q   G   N   V   F   S   C   S   V   M   H   E   A   L   H   N   H   Y   T   Q   K   S
Ch27_10H    acc gtg gac aag agc agg tgg cag cag ggg aac gtc ttc tca tgc tcc gtg atg cat gag gct ctg cac aac cac tac acg cag aag agc 451  L   S   L   S   P   G   K       (SEQ ID NO: 26)
Ch27_10H    ctc tcc ctg tct ccg ggt aaa       (SEQ ID NO: 7)
```

Figure 3a

FG27 RHA (DNA Sequence)

CAGGTCCAGCTGGTCGAATCAGGGGGAGGCGTCGTGCAGCCCGGAAGGTCACTGAGACTGTCATGTGCCGCATC
AGGGTTTACTTTCTCACACTACTATATGTACTGGGTGCGACAGGCTCCAGGCAAGGGACTGGAGTGGGTCGCATA
TATCAGCAACGACGGCGATAATACTTACTATCCTGACACCATCCGGGGGAGATTCACAATCTCTAGAGATAACAG
TAAGAACACTCTGTACCTGCAGATGAACTCTCTGAGGGCAGAAGACACCGCCGTGTACTATTGCGCCCGCGGGAA
ATACGATGGAGCCTGGTTTGCTTATTGGGGACAGGGCACCCTGGTGACAGTCAGCTCC    (SEQ ID NO: 11)

FG27 RHA (Protein Sequence)

CDR1                                            CDR2

QVQLVESGGGVVQPGRSLRLSCAASGFTFSHYYMYWVRQAPGKGLEWVAYISNDGDNTYPDTIRGRFTISRDNSKN
TLYLQMNSLRAEDTAVYYCARGKYDGAWFAYWGQGTLVTVSS    (SEQ ID NO: 12)

CDR3

CONSTANT REGION SEQUENCES

DNA SEQUENCE- HuG1

GCCTCCACCAAGGGCCCTTCCGTGTTCCCTCTGGCCCCTTCCTCCAAGTCCACCTCCGGC
GGCACCGCCGCTCTGGGCTGCCTGGTGAAGGACTACTTCCCTGAGCCTGTGACCGTGTCC
TGGAACTCTGGCGCCCTGACCAGCGGCGTGCACACCTTCCCTGCCGTGCTGCAGTCCTCC
GGCCTGTACTCCCTGTCCTCCGTGGTGACCGTGCCTTCCTCCTCCCTGGGCACCCAGACC
TACATCTGCAACGTGAACCACAAGCCTTCCAACACCAAGGTGGACAAGAAGGTGGAGCCT
AAGTCCTGCGACAAGACCCACACGTGCCCTCCATGCCCAGCTCCCGAGCTGCTGGGCGGA
CCAAGCGTGTTTCTGTTCCCTCCTAAGCCTAAGGACACCCTGATGATCTCCCGGACCCCT
GAGGTGACGTGCGTGGTGGTGGACGTGTCCCACGAGGACCCAGAGGTGAAGTTCAATTGG
TACGTGGACGGCGTGGAGGTGCACAACGCCAAGACCAAGCCTCGGGAGGAACAGTACAAC
TCCACCTACCGGGTGGTGTCTGTGCTGACCGTGCTGCACCAGGACTGGCTGAACGGCAAG
GAATACAAGTGCAAAGTCTCCAACAAGGCCCTGCCTGCCCCCATCGAAAAGACCATCTCC
AAGGCCAAGGGCCAGCCTCGCGAGCCTCAGGTGTACACCCTGCCTCCAAGCAGGGAGGAA
ATGACCAAGAACCAGGTGTCCCTGACCTGTCTGGTGAAGGGCTTCTACCCTTCCGATATC
GCCGTGGAGTGGGAGTCCAACGGCCAGCCTGAGAACAACTACAAGACCACCCCTCCTGTG
CTGGACTCCGACGGCTCCTTCTTCCTGTACTCCAAGCTGACCGTGGACAAGTCCCGGTGG
CAGCAGGGCAACGTGTTCTCCTGCTCCGTGATGCACGAGGCCCTGCACAACCACTACACC
CAGAAGAGCCTCTCCCTGTCCCCGGGTAAA    (SEQ ID NO: 13)

PROTEIN SEQUENCE- HuG1

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREE
MTKNQVSLTCLVKGFYPSDIAVEWESNGQPENNYKTTPPVLDSDGSFFLYSKLTVDKSRW
QQGNVFSCSVMHEALHNHYTQKSLSLSPGK    (SEQ ID NO: 14)

Figure 3b

FG27 RKC (DNA Sequence)
ATGGAAGCCCCAGCGCAGCTTCTCTTCCTCCTGCTACTCTGGCTCCCTGATACCACCGGAGACGTCGTGATGACCC
AGAGCCCACTGAGCCTGCCTGTGACACCCGGCGAGCCCGCAAGTATTTCCTGTAGAAGTTCCCAGATTATCGTGC
ACACTAACGGGAATACCTACCTGGAGTGGTATCTGCAGAAGCCCGGCCAGAGTCCTCAGCTGCTGATCTACAAAG
TGAGTAACCGGTTCTCAGGAGTCCCAGACCGGTTCAGCGGCTCCGGGTCTGGAACCGATTTCACACTGAAGATTA
GCAGGGTGGAGGCCGAAGACGTGGGAGTCTACTATTGCTTTCAGGGCTCCCATGTCCCCTTCACATTTGGCCAGG
GGACCAAGCTGGAAATCAAA    (SEQ ID NO: 15)

FG27 RKC (Protein Sequence)

CDR1

MEAPAQLLFLLLLWLPDTTGDVVMTQSPLSLPVTPGEPASISC⌐RSSQIIVHTNGNTYLE¬WYLQKPGQSPQLLIY
⌐KVSNRFS¬GVPDRFSGSGSGTDFTLKISRVEAEDVGVYYC⌐FQGSHVPFT¬GQGTKLEIK    (SEQ ID NO: 16)
   CDR2                                            CDR3

DNA SEQUENCE- HuK
AGAACTGTGGCAGCACCAAGCGTCTTCATCTTCCCGCCATCTGATGAGCAGTTGAAATCT
GGAACTGCCTCTGTTGTGTGCCTGCTGAATAACTTCTATCCCAGAGAGGCCAAAGTACAG
TGGAAGGTGGATAACGCCCTCCAATCGGGTAACTCCCAGGAGAGTGTCACAGAGCAGGAC
AGCAAGGACAGCACCTACAGCCTCAGCAGCACCCTGACGCTGAGCAAAGCAGACTACGAG
AAACACAAAGTCTACGCCTGCGAAGTCACCCATCAGGGCCTGAGCTCGCCCGTCACAAAG
AGCTTCAACAGGGGAGAGTGT    (SEQ ID NO: 17)

PROTEIN SEQUENCE- HuK
RTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC    (SEQ ID NO: 18)

Figure 6

Figure 7
a)
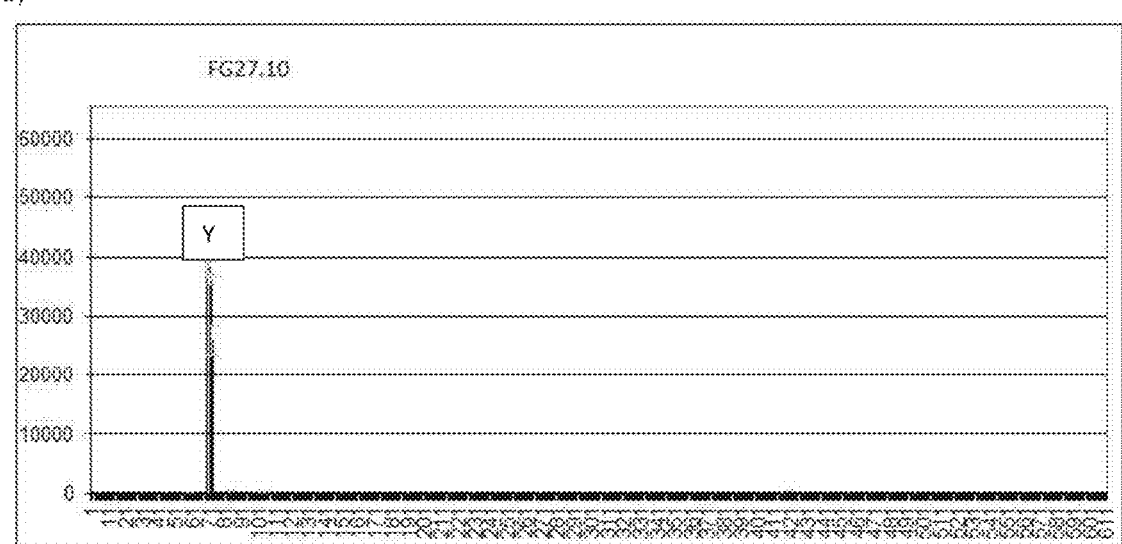
b)
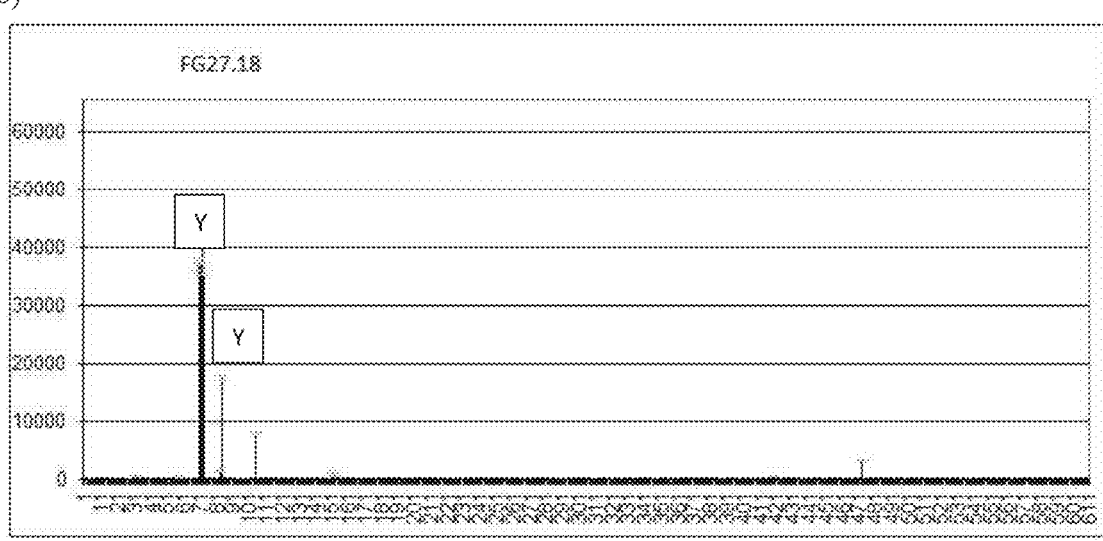

Figure 7 contd
c)
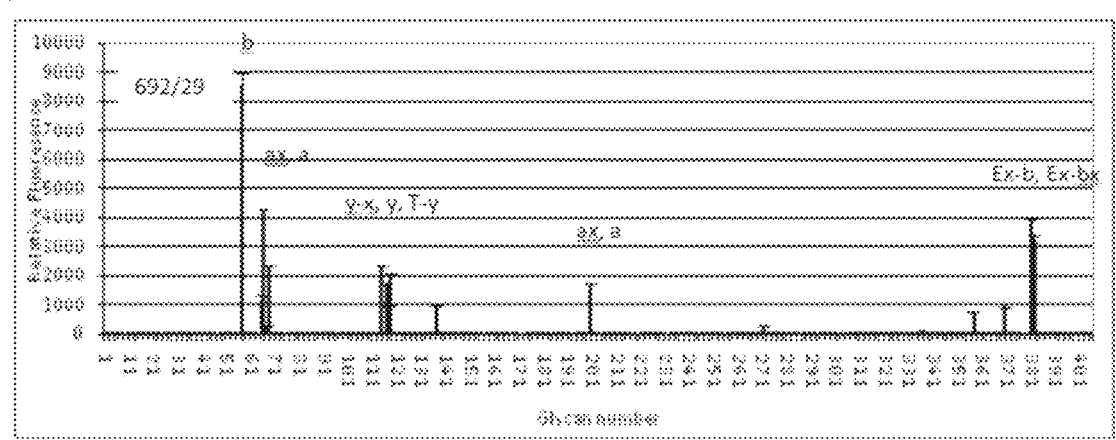
d)
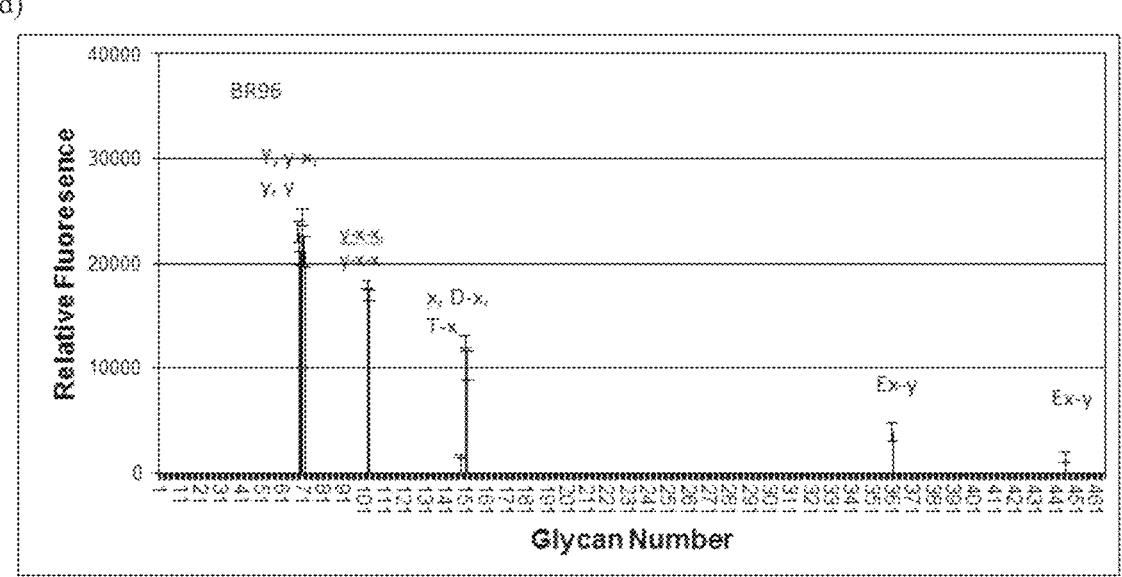

M: Marker
1. AGS: PM
2. AGS: L
3. HCT15: PM
4. HCT15: L
5. OVCAR3: PM
6. OVCAR3: L
7. MCF7: PM
8. MCF7: L
9. H322: PM
10. H322: L Figure 9
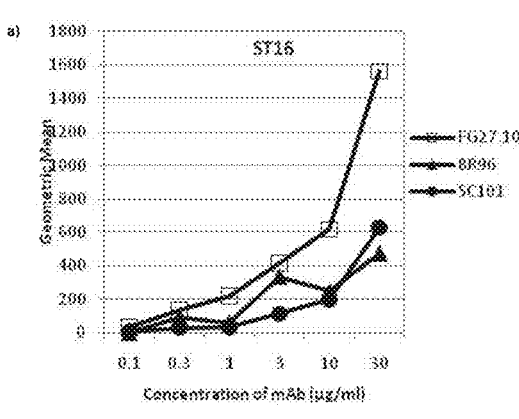
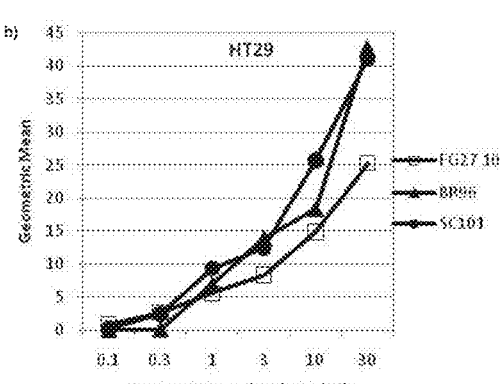
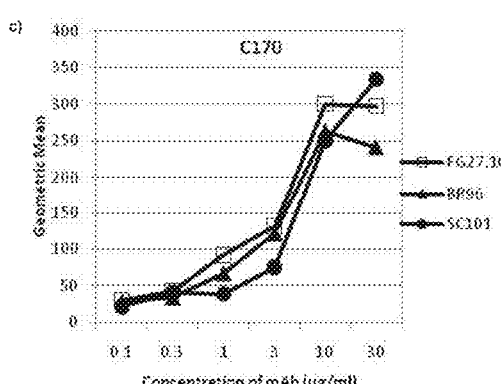
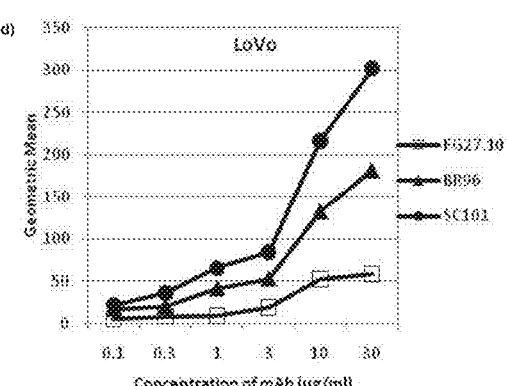
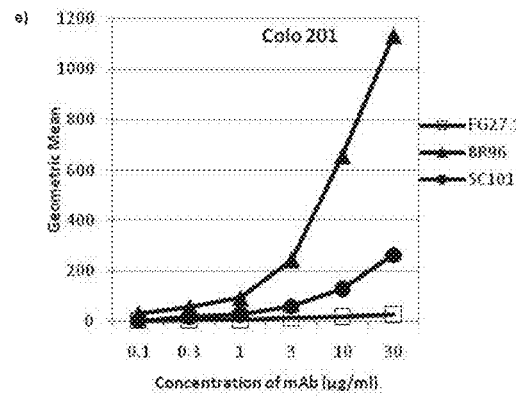
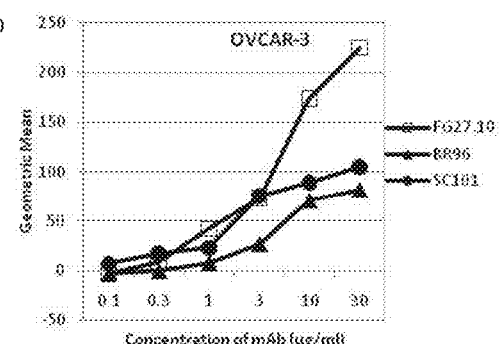
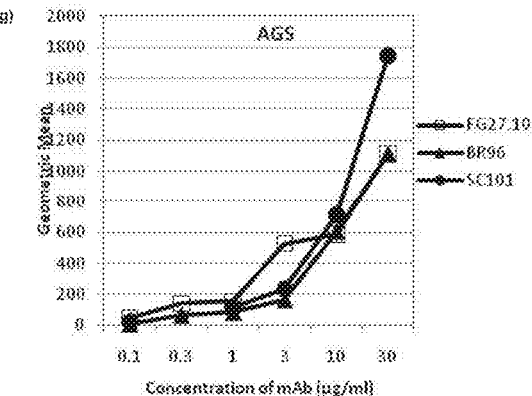

Figure 13a

Figure 13a cont.

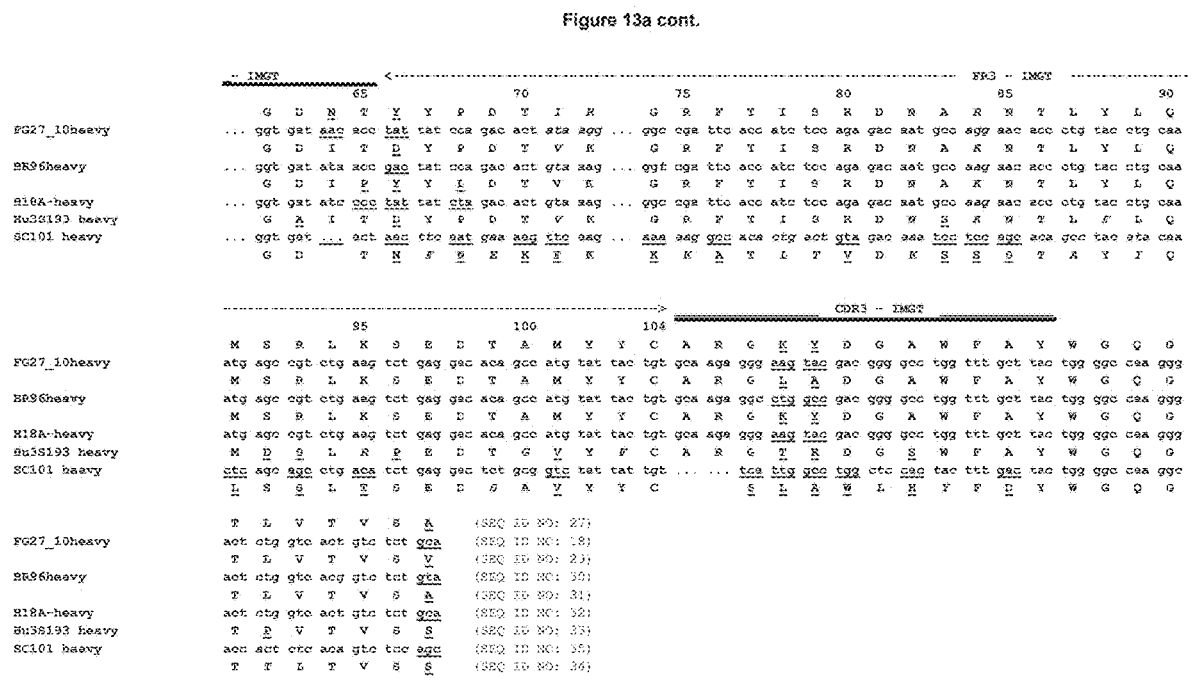

```
                    ~ IMGT          <---------------------------------------------------------------------     FR3 - IMGT   --------------
                         65                        70                     75                 80                 85                  90
                      G   D   N   T   Y   Y   P   D   T   I   R       G   R   F   T   I   S   R   D   N   A   R   N   T   L   Y   L   Q
FG27_10heavy      ... ggt gat aac acc tat tat cca gac act ata agg ... ggc cga ttc acc atc tcc aga gac aat gcc agg aac acc ctg tac ctg caa
                      G   D   I   T   D   Y   P   D   T   V   K       G   R   F   T   I   S   R   D   N   A   K   N   T   L   Y   L   Q
BR96heavy         ... ggt gat ata acc gac tat cca gac act gta aag ... ggt cga ttc acc atc tcc aga gac aat gcc aag aac acc ctg tac ctg caa
                      G   D   I   P   Y   Y   L   D   T   V   K       G   R   F   T   I   S   R   D   N   A   K   N   T   L   Y   L   Q
R18A-heavy        ... ggt gat atc ccc tat tat cta gac act gta aag ... ggc cga ttc acc atc tcc aga gac aat gcc aag aac acc ctg tac ctg caa
Hu3S193 heavy         G   A   I   T   D   Y   P   D   T   V   K       G   R   F   T   I   S   R   D   N   S   K   N   T   L   F   L   Q
SC101 heavy       ... ggt gat ... act aac ttc aat gaa aag ttc aag ..  aaa aag gcc aca ctg act gta gac aaa tcc tcc agc aca gcc tac ata caa
                      G   D       T   N   F   N   E   K   F   K       K   K   A   T   L   T   V   D   K   S   S   S   T   A   Y   I   Q ------------------------------------------------------------>       CDR3 - IMGT
                             85                   100                 104
                      M   S   R   L   K   S   E   D   T   A   M   Y   Y   C   A   R   G   K   Y   D   G   A   W   F   A   Y   W   G   Q   G
FG27_10heavy      atg agc cgt ctg aag tct gag gac aca gcc atg tat tac tgt gca aga ggg aag tac gac ggg gcc tgg ttt gct tac tgg ggc caa ggg
                      M   S   R   L   K   S   E   D   T   A   M   Y   Y   C   A   R   G   L   A   D   G   A   W   F   A   Y   W   G   Q   G
BR96heavy         atg agc cgt ctg aag tct gag gac aca gcc atg tat tac tgt gca aga ggc ctg gcc gac ggg gcc tgg ttt gct tac tgg ggc caa ggg
                      M   S   R   L   K   S   E   D   T   A   M   Y   Y   C   A   R   G   K   Y   D   G   A   W   F   A   Y   W   G   Q   G
R18A-heavy        atg agc cgt ctg aag tct gag gac aca gcc atg tat tac tgt gca aga ggg aag tac gac ggg gcc tgg ttt gct tac tgg ggc caa ggg
Hu3S193 heavy         M   D   Q   L   R   P   E   D   T   G   V   Y   Y   F   C   A   R   G   T   R   D   G   S   W   F   A   Y   W   G   Q   G
SC101 heavy       ctc agc agc ctg aca tct gag gac tct gcg gtc tat tat tgt ... ... tca ttg gcc tgg ctc cac tac ttt gac tac tgg ggc caa ggc
                      L   S   S   L   T   S   E   D   S   A   V   Y   Y   C       S   L   A   W   L   H   Y   F   D   Y   W   G   Q   G T   L   V   T   V   S   A     (SEQ ID NO: 27)
FG27_10heavy      act ctg gtc act gtc tct gca       (SEQ ID NO: 18)
                      T   L   V   T   V   S   V     (SEQ ID NO: 29)
BR96heavy         act ctg gtc acg gtc tct gta       (SEQ ID NO: 30)
                      T   L   V   T   V   S   A     (SEQ ID NO: 31)
R18A-heavy        act ctg gtc act gtc tct gca       (SEQ ID NO: 32)
Hu3S193 heavy         T   P   V   T   V   S   S     (SEQ ID NO: 33)
SC101 heavy       acc act ctc aca gtc tcc agc       (SEQ ID NO: 35)
                      T   T   L   T   V   S   S     (SEQ ID NO: 36)
```

Figure 13b

Figure 13b cont.

Figure 17a
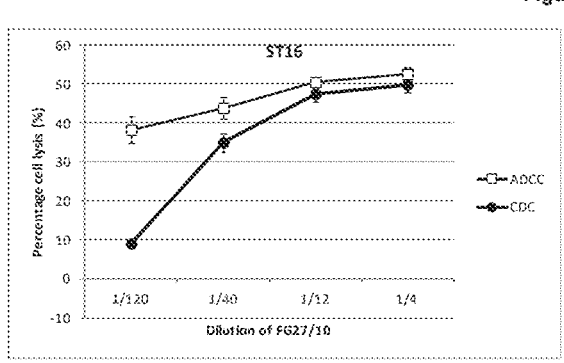
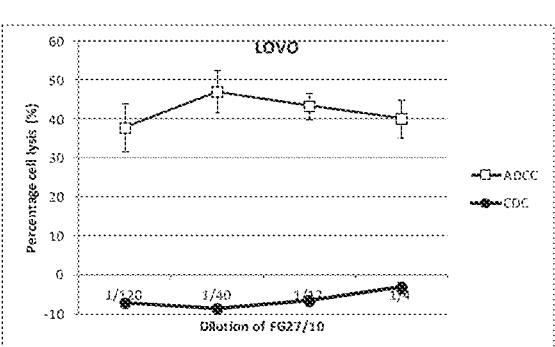
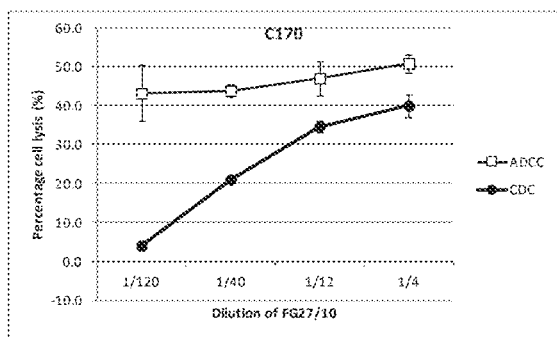
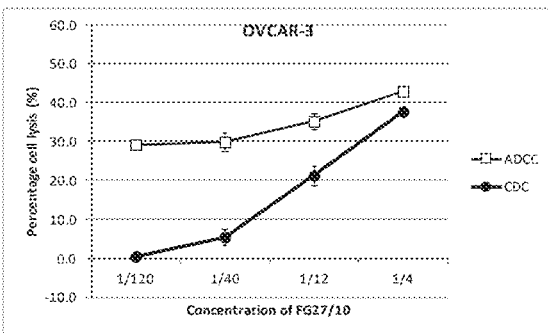
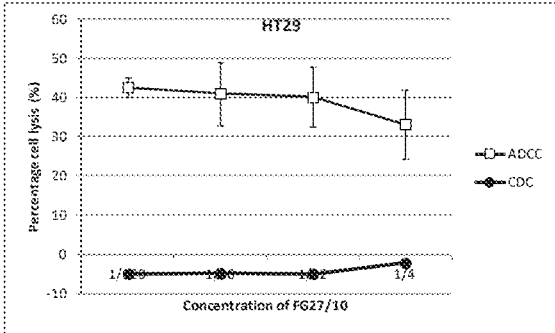
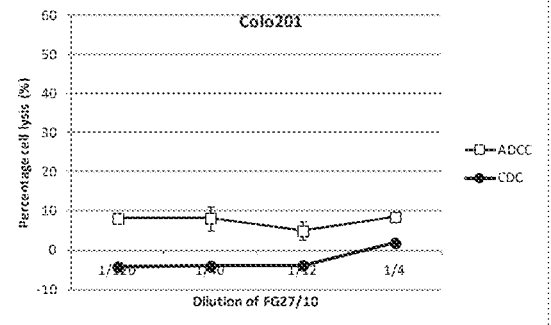

Figure 18

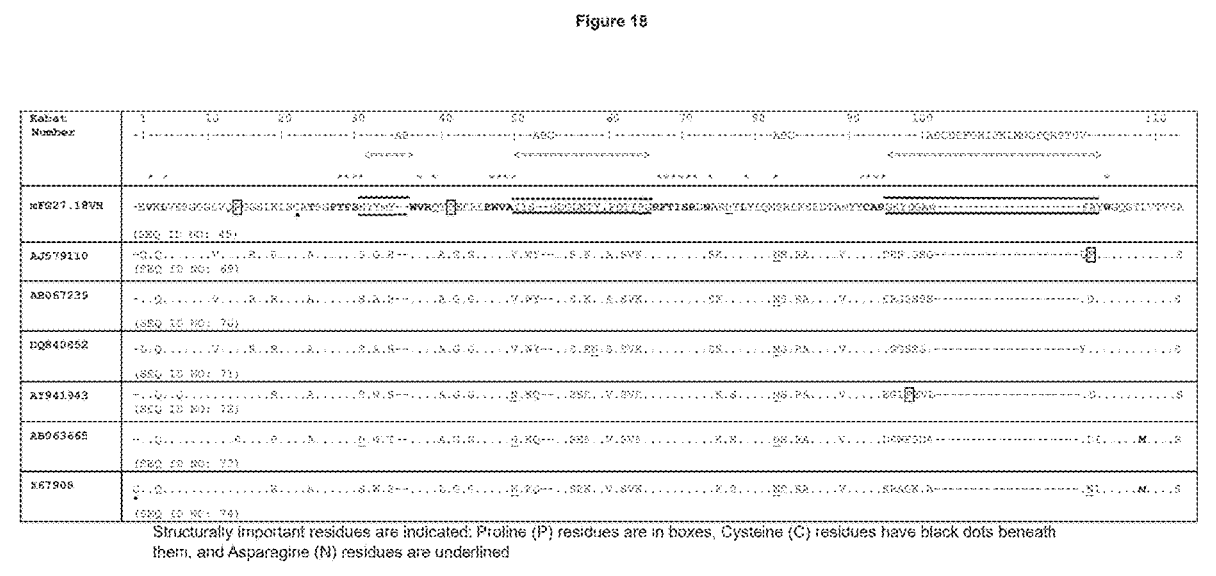

Structurally important residues are indicated: Proline (P) residues are in boxes, Cysteine (C) residues have black dots beneath them, and Asparagine (N) residues are underlined

Figure 19

| | ID | SIM | FR | FRs | VCI | VCIs | Prox | 4Å Proximity Residues | H1 | H2 | H3 |
|---|---|---|---|---|---|---|---|---|---|---|---|
| FG27_Heavy | | | | | 22 | | | VLTFTFSWVREWVARFTISRNLCARW<br>(SEQ ID NO: 46) | 5 | 17 | 10 |
| AJ579110 | 82 | 450 | 70 | 381 | 21 | 115 | 25 | ..A......................<br>(SEQ ID NO: 75) | 5 | 17 | 10 |
| AB067239 | 83 | 449 | 71 | 384 | 21 | 115 | 25 | ..A......................<br>(SEQ ID NO: 75) | 5 | 17 | 10 |
| DQ840852 | 83 | 453 | 70 | 376 | 21 | 115 | 25 | ..A......................<br>(SEQ ID NO: 75) | 5 | 7 | 10 |
| AY941943 | 83 | 444 | 72 | 391 | 21 | 115 | 25 | ..A......................<br>(SEQ ID NO: 75) | 5 | 17 | 10 |
| AB063665 | 81 | 437 | 71 | 383 | 21 | 115 | 25 | ..A......................<br>(SEQ ID NO: 75) | 5 | 17 | 10 |
| X67908 | 83 | 444 | 72 | 391 | 21 | 115 | 25 | ..A......................<br>(SEQ ID NO: 75) | 5 | 17 | 10 |

Cysteine residue is highlighted with a black dot beneath

Figure 20

AJ579110

*Closest V-REGIONs (evaluated from the V-REGION first nucleotide to the 2nd-CYScodon)*

Figure 21

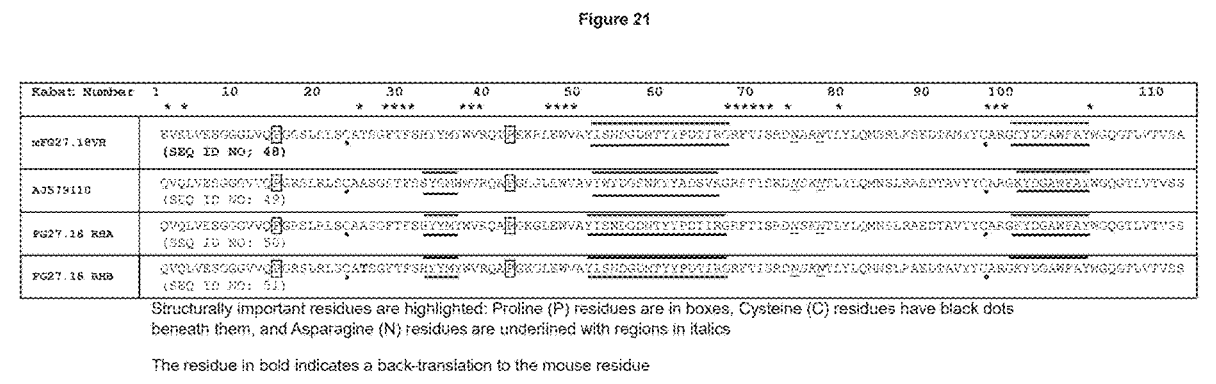

Structurally important residues are highlighted: Proline (P) residues are in boxes, Cysteine (C) residues have black dots beneath them, and Asparagine (N) residues are underlined with regions in italics The residue in bold indicates a back-translation to the mouse residue

Figure 22

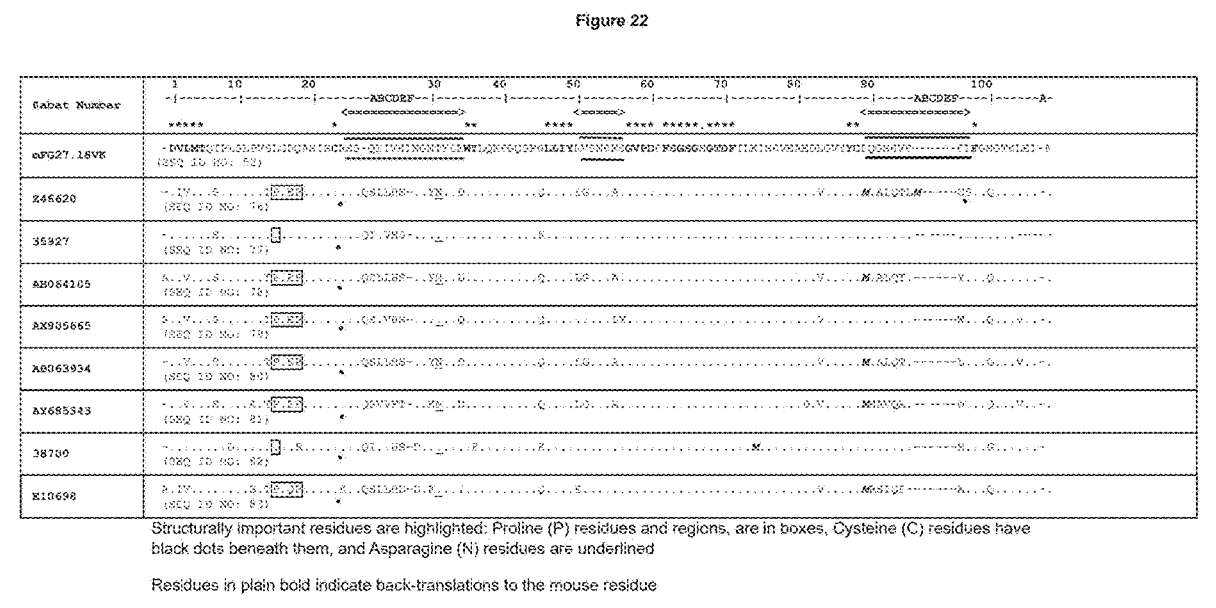

Structurally important residues are highlighted: Proline (P) residues and regions, are in boxes, Cysteine (C) residues have black dots beneath them, and Asparagine (N) residues are underlined Residues in plain bold indicate back-translations to the mouse residue

Figure 23

| | ID | SIM | FR | FRs | VCI | VCIs | Prox | 4Å Proximity Residues | L1 | L2 | L3 |
|---|---|---|---|---|---|---|---|---|---|---|---|
| FG27_Kappa | | | | | 17 | | 28 | DVLMTCWYLLIYGVPDFSGSGGIDFYCF (SEQ ID NO: 93) | 16 | 7 | 10 |
| Z46620 | 82 | 425 | 70 | 378 | 16 | 99 | 26 | .IV............................ (SEQ ID NO: 84) | 16 | 7 | 9 |
| 35927 | 101 | 528 | 74 | 391 | 17 | 100 | 28 | .............................. (SEQ ID NO: 93) | 16 | 7 | 9 |
| AB064105 | 85 | 445 | 71 | 379 | 17 | 100 | 27 | ..V........................... (SEQ ID NO: 85) | 16 | 7 | 9 |
| AX805665 | 93 | 496 | 70 | 376 | 17 | 100 | 27 | ..V........................... (SEQ ID NO: 85) | 16 | 7 | 9 |
| AB063934 | 84 | 439 | 70 | 376 | 17 | 100 | 27 | ..V........................... (SEQ ID NO: 85) | 16 | 7 | 9 |
| AY685343 | 81 | 429 | 68 | 365 | 17 | 100 | 27 | ..V........................... (SEQ ID NO: 85) | 16 | 7 | 9 |
| 38700 | 99 | 508 | 73 | 382 | 16 | 96 | 27 | .......F...................... (SEQ ID NO: 86) | 16 | 7 | 9 |
| E10698 | 83 | 434 | 70 | 372 | 16 | 99 | 26 | .IV........................... (SEQ ID NO: 84) | 16 | 7 | 8 |

Figure 24

X72449

Closest V-REGIONs (evaluated from the V-REGION first nucleotide to the 2nd-CYS codon plus 15 nt of the CDR3-IMGT)

```
                             Score      Identity
X63397 Homsap IGKV2-28*01 F  1447       99,32% (292/294 nt)
X12691 Homsap IGKV2D-28*01 F 1447       99,32% (292/294 nt)
Z59318 Homsap IGKV2-40*01 F  1213       90,14% (265/294 nt)
X59311 Homsap IGKV2D-40*01 F 1213       90,14% (265/294 nt)
X63400 Homsap IGKV2-18*01 P  1177       88,78% (261/294 nt)
```

```
            ----------+---------+---------+---------+---------+---------+---------+---------+---------+---------+
                 10        20        30        40        50        60        70        80        90        100
            ----------+---------+---------+---------+---------+---------+---------+---------+---------+---------+
X63397.seq  DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPP(SEQ ID NO 54)
X12691.seq  .....................................................................................................
X72449.seq  ...............................I.....................................T.............................PWT
```

Figure 25

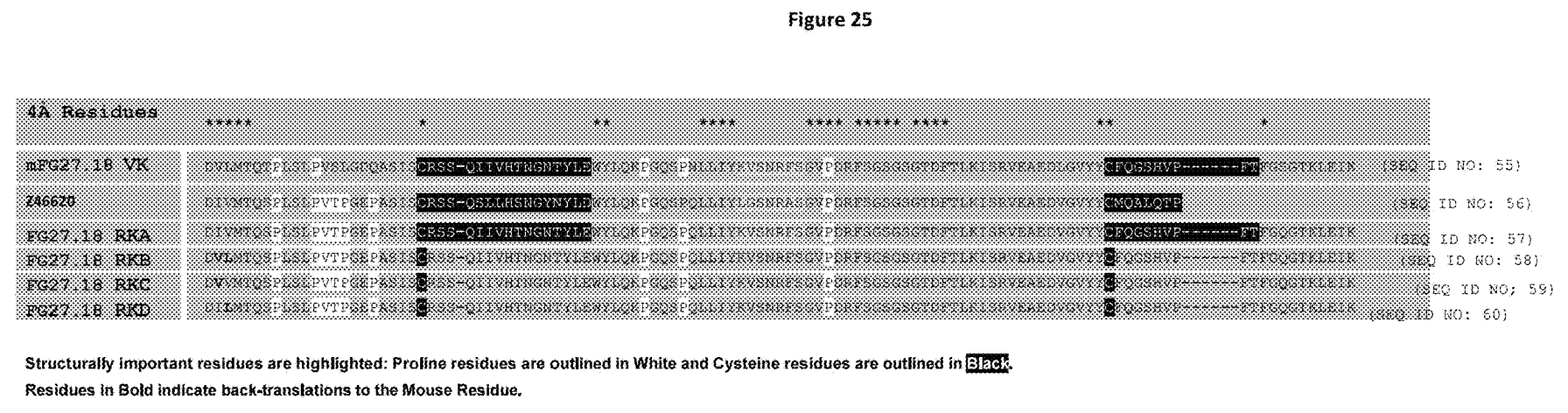

Structurally important residues are highlighted: Proline residues are outlined in White and Cysteine residues are outlined in Black.

Residues in Bold indicate back-translations to the Mouse Residue.

Figure 26

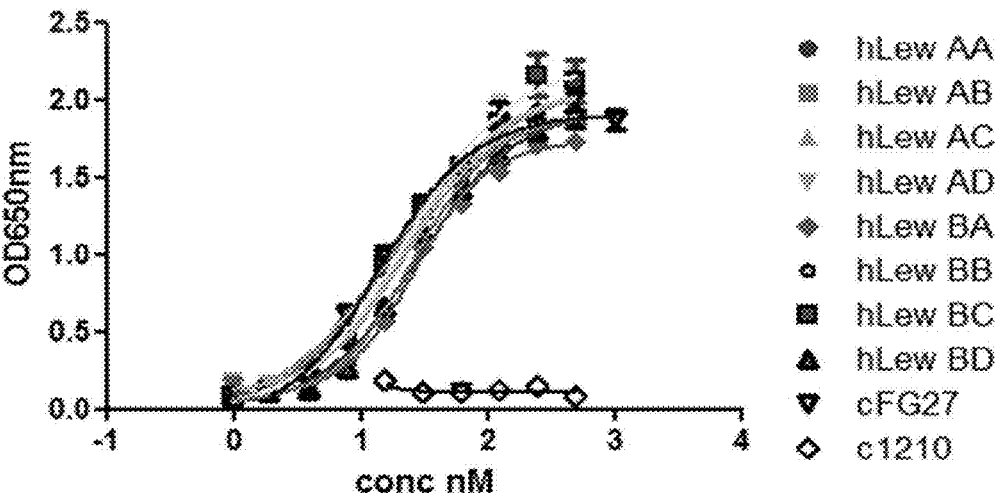

| Antibody | hLewAA | hLewAB | hLewAC | hLewAD | hLewBA | hLewBB | hLewBC | hLewBD | cFG27 | c1210 |
|---|---|---|---|---|---|---|---|---|---|---|
| Expression ug/ml | 71 | 32 | 50 | 64 | 68 | 68 | 56 | 64 | 50 | 110 |
| EC50 nM | 28 | 18 | 18 | 23 | 27 | 23 | 24 | 26 | 14 | |

Legend: Comparison of antibody binding to LewisY-HSA antigen for combinations of antibody expressed as LewRHA with LewRKA, LewRKB, LewRKC or LewRKD and LewRHB with LewRKA, LewRKB, LewRKC or LewRKD, including cFG27 positive control antibody and c1210 negative control antibody.

Figure 27

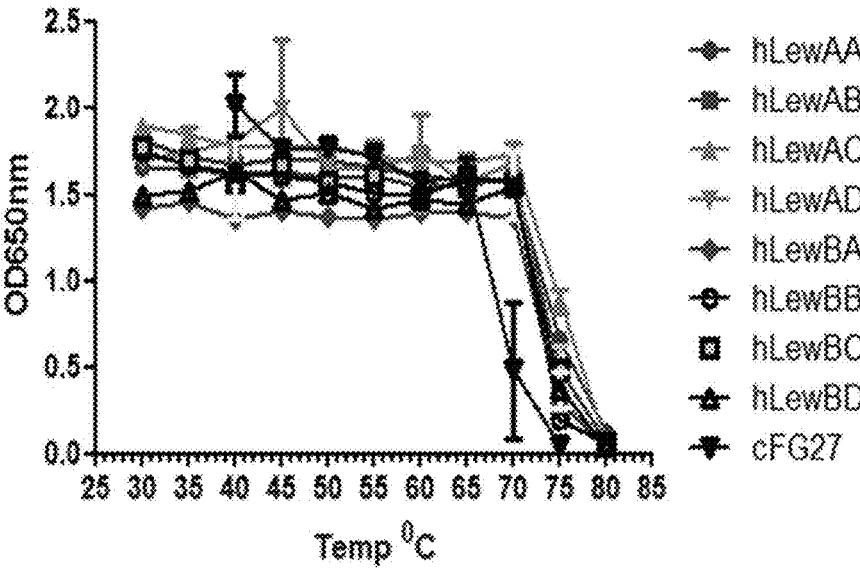

| Antibody | Tm (°C) |
|----------|---------|
| cFG27    | 72      |
| hLewAB   | 72      |
| hLewAC   | 72      |
| hLewAD   | 72      |
| hLewBC   | 72      |

| | Kon(1/Ms) | Koff (1/s) | Kd (M) | Rmax (RU) |
|---|---|---|---|---|
| Ch27_fc34 | 6.6E+04 | 2.2E-04 | 3.3E-09 | 1374 |
| MRC chim27 | 7.1E+05 | 2.8E-04 | 4.0E-10 | 1816 |
| RHA/RKD | 3.48E+04 | 4.6E-04 | 1.3E-08 | 1040 |
| RHA/RKB | 5.72E+04 | 8.2E-05 | 1.4E-09 | 1296 |
| RHA/RKC | 5.9E+04 | 1.3E-04 | 2.2E-09 | 1274 |
| RHB/RKC | 3.0E+05 | 9.5E-04 | 3.1E-09 | 1477 |

| Antibody | Retention Index (k') |
|---|---|
| Commercial | 0.044 |
| CNTO607 | 0.685 |
| Lewis Y AB | 0.219 |
| Lewis Y AC | -0.014 |
| Lewis Y AD | -0.023 |
| Lewis Y BC | -0.012 |

Figure 33

27 Light chain DNA sequence (variable region + Kappa constant)

Atgaagttgcctgttaggctgttggtgctgatgttctggattcctgcttccatcagtgatgtttttgatgacccaaactccactctccctgcctgtcagt
cttggagatcaagcctccatctcttgcagatctagtcagatcattgtacatactaatggaaacacctatttagaatggtacctgcagaaaccaggccag
tctccaaacctcctgatctacaaagtttccaaccgattttctggggtcccagacaggttcagtggcagtggatcagggacagatttcacactcaagatc
agcagagtggaggctgaggatctgggagtttattactgctttcaaggtcacatgttccattcacgttcggctcggggacaaagttggaaataaaacgt
acggtagcggccccatctgtcttcatcttcccgccatctgatgagcagttgaaatctggaactgcctctgttgtgtgcctgctgaataacttctatccc
agagaggccaaagtacagtggaaggtggataacgccctccaatcgggtaactcccaggagagtgtcacagagcaggacagcaaggacagcacctacagc
ctcagcagcaccctgacgctgagcaaagcagactacgagaaacacaaagtctacgcctgcgaagtcacccatcagggcctgagctcgcccgtcacaaag
agcttcaacaggggagagtgt     (SEQ ID NO: 19)

27 Light chain protein sequence (variable region + Kappa constant)

MKLPVRLLVLMFWIPASISDVLMTQTPLSLPVSLGDQASISCRSSQIIVHTNGNTYLEWYL

QKPGQSPNLLIYKVSNRFSGVPDRFSGSGSGTDFTLKISRVEAEDLGVYYCFQGHVPFTF

GSGTKLEIKRTVAAPSVFIFPPSDEQLKSGTASVVCLLNNFYPREAKVQWKVDNALQSGNS

QESVTEQDSKDSTYSLSSTLTLSKADYEKHKVYACEVTHQGLSSPVTKSFNRGEC     (SEQ ID NO: 20)

Heavy chain DNA sequence of i27vl (variable + 'improved' vl constant region)

atgaacttctggctcagcttgattttccttgtccttgttttaaaaggtgtccagtgtgaagtgaagctggtggagtctggggaggcttagtgcagcct
ggagggtccctgaaactctcctgtgcaacctctggattcactttcagtcactattacatgtattgggttcgccagactccagagaagaggctggagtgg
gtcgcatacattagtaatgatggtgataacacctattatccagacataagggccgattcaccatctccagagacaatgccaggaacaccctgtac
ctgcaaatgagccgtctgaagtctgaggacacagccatgtattactgtgcaagagggaagtacgacggggctggtttgcttactgggggccaaggggact
ctggtcactgtctctagcgcttccaccaaggggccatcggtcttccccctggcaccctcctccaagagcacctctgggggcacagcggccctgggctgc
ctggtcaaggactacttccccgaaccggtgacggtgtcgtggaactcaggcgccctgaccagcggcgtgcacaccttcccggctgtcctacagtcctca
ggactctactccctcagcagcgtggtgaccgtgccctccagcagcttgggcacccagacctacatctgcaacgtgaatcacaagcccagcaacaccaag
gtggacaagaaagttgagcccaaatcttgtgacaaaactcacacatgcccaccgtgcccagcacctgaactcctggggggaccgtcagtcttcctcttc
cccccaaaacccaaggacaccctcatgatctcccggacccctgaggtcacatgcgtggtggtggacgtgagccacgaagaccctgaggtcaagttcaac
tggtacgtggacggcgtggaggtgcatacagcctggacacagcccgtgaagagcagtacaacagtacctacaccgtggtggagtgtcctcaccgtcctg
caccaggactggctgaatggcaaggagtacaagtgtccaacaaagcccaccatctccaaagccaaaggtgtacaccctgcccccatcccgggaggagatg
gccacagaccctcaagtatacaccataccccacctcgtgcaaaatgtccaagaagaaggttagtctgacctgcctggtcaaaggcttctatcctagcgac
atcagtgtggagtgggagagcaatgggcagccggagaacaactacaagaccacgcctcccgtgctggactccgacggctccttcttcctctacagc
aagctcaccgtggacaagagcaggtggcagcaggggaacgtcttctcatgctccgtgatgcatgaggctctgcacaaccactacacgcagaagagcctc
tccctgtctccgggtaaa     (SEQ ID NO: 21)

Heavy chain Protein sequence of i27vl (variable + 'improved' vl constant region)

MNFWLSLIFLVLVLKGVQCEVKLVESGGGLVQPGGSLKLSCATSGFTFSHYYMYWVRQTP

EKRLEWVAYISNDGDNYYPDTIRGRFTISRDNARNTLYLQMSRLKSEDTAMYYCARGRY

DGAWFAYWGQGTLVTVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHTAWTQPREEQYN

STYRVVSVLTVLHQDWLNGKEYKCKVSNKALPAPIEKTISKPKGRAQTPQVYTIPPPREQ

MSKKKVSLTCLVTNFFSEAISVEWESNGQPENNYKTTPPVLDSDGSFFLYSKLTVDKSRW

QQGNVFSCSVMHEALHNHYTQKSLSLSPGK     (SEQ ID NO: 22)

SEQUENCE LISTING

<160> NUMBER OF SEQ ID NOS: 90

<210> SEQ ID NO 1
<211> LENGTH: 1401

```
<212> TYPE: DNA
<213> ORGANISM: Artificial sequence
<220> FEATURE:
<223> OTHER INFORMATION: Heavy chain DNA sequence of 27.10

<400> SEQUENCE: 1
atgaacttct ggctcagctt gattttcctt gtccttgttt taaaaggtgt ccagtgtgaa      60
gtgaagctgg tggagtctgg gggaggctta gtgcagcctg agggtccct gaaactctcc      120 tgtgcaacct ctggattcac tttcagtcac tattacatgt attgggttcg ccagactcca      180
gagaagaggc tggagtgggt cgcatacatt agtaatgatg gtgataacac ctattatcca      240
gacactataa ggggccgatt caccatctcc agagacaatg ccaggaacac cctgtacctg      300
caaatgagcc gtctgaagtc tgaggacaca gccatgtatt actgtgcaag agggaagtac      360
gacggggcct ggtttgctta ctggggccaa gggactctgg tcactgtctc tgcagctaca      420
acaacagccc catctgtcta tcccttggtc cctggctgca gtgacacatc tggatcctcg      480
gtgacactgg atgccttgt caaaggctac ttccctgagc cggtaactgt aaaatggaac      540
tatggagccc tgtccagcgg tgtgcgcaca gtctcatctg tcctgcagtc tgggttctat      600
tccctcagca gcttggtgac tgtaccctcc agcacctggc ccagccagac tgtcatctgc      660
aacgtagccc acccagccag caagactgag ttgatcaaga aatcgagcc tagaataccc      720 aagcccagta cccccccagg ttcttcatgc ccacctggta acatcttggg tggaccatcc      780
gtcttcatct ccccccaaa gcccaaggat gcactcatga tctccctaac ccccaaggtt      840
acgtgtgtgg tggtggatgt gagcgaggat gacccagatg tccatgtcag ctggtttgtg      900
gacaacaaag aagtacacac agcctggaca cagccccgtg aagctcagta caacagtacc      960
ttccgagtgg tcagtgccct ccccatccag caccaggact ggatgagggg caaggagttc      1020
aaatgcaagg tcaacaacaa agccctccca gcccccatcg agagaaccat ctcaaaaccc      1080
aaaggaagag cccagacacc tcaagtatac accataccc cacctcgtga acaaatgtcc      1140
aagaagaagg ttagtctgac ctgcctggtc accaacttct tctctgaagc catcagtgtg      1200
gagtgggaaa ggaacggaga actggagcag gattacaaga acactccacc catcctggac      1260
tcagatggga cctacttcct ctacagcaag ctcactgtgg atacagacag ttggttgcaa      1320
ggagaaattt ttacctgctc cgtggtgcat gaggctctcc ataaccacca cacacagaag      1380
ctgtctcgct cccctggtaa a                                                1401

<210> SEQ ID NO 2
<211> LENGTH: 465
<212> TYPE: PRT
<213> ORGANISM: Artificial sequence
<220> FEATURE:
<223> OTHER INFORMATION: Heavy chain protein sequence of 27.10

<400> SEQUENCE: 2

Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Tyr Tyr Met Tyr Trp Val Arg Gln Thr Pro Glu Lys Arg Leu Glu Trp
    50                  55                  60

Val Ala Tyr Ile Ser Asn Asp Asp Asn Thr Tyr Tyr Pro Asp Thr Ile
65                  70                  75                  80
```

Arg Gly Arg Phe Thr Ile Ser Arg Asp Asn Ala Arg Asn Thr Leu Tyr
            85              90              95

Leu Gln Met Ser Arg Leu Lys Ser Glu Asp Thr Ala Met Tyr Tyr Cys
            100             105             110

Ala Arg Gly Lys Tyr Asp Gly Ala Trp Phe Ala Tyr Trp Gly Gln Gly
            115             120             125

Thr Leu Val Thr Val Ser Ala Ala Thr Thr Thr Ala Pro Ser Val Tyr
    130             135             140

Pro Leu Val Pro Gly Cys Ser Asp Thr Ser Gly Ser Ser Val Thr Leu
145             150             155             160

Gly Cys Leu Val Lys Gly Tyr Phe Pro Glu Pro Val Thr Val Lys Trp
            165             170             175

Asn Tyr Gly Ala Leu Ser Ser Gly Val Arg Thr Val Ser Ser Val Leu
            180             185             190

Gln Ser Gly Phe Tyr Ser Leu Ser Ser Leu Val Thr Val Pro Ser Ser
            195             200             205

Thr Trp Pro Ser Gln Thr Val Ile Cys Asn Val Ala His Pro Ala Ser
    210             215             220

Lys Thr Glu Leu Ile Lys Arg Ile Glu Pro Arg Ile Pro Lys Pro Ser
225             230             235             240

Thr Pro Pro Gly Ser Ser Cys Pro Pro Gly Asn Ile Leu Gly Gly Pro
            245             250             255

Ser Val Phe Ile Phe Pro Pro Lys Pro Lys Asp Ala Leu Met Ile Ser
            260             265             270

Leu Thr Pro Lys Val Thr Cys Val Val Val Asp Val Ser Glu Asp Asp
            275             280             285

Pro Asp Val His Val Ser Trp Phe Val Asp Asn Lys Glu Val His Thr
    290             295             300

Ala Trp Thr Gln Pro Arg Glu Ala Gln Tyr Asn Ser Thr Phe Arg Val
305             310             315             320

Val Ser Ala Leu Pro Ile Gln His Gln Asp Trp Met Arg Gly Lys Glu
            325             330             335

Phe Lys Cys Lys Val Asn Asn Lys Ala Leu Pro Ala Pro Ile Glu Arg
            340             345             350

Thr Ile Ser Lys Pro Lys Gly Arg Ala Gln Thr Pro Gln Val Tyr Thr
            355             360             365

Ile Pro Pro Pro Arg Glu Gln Met Ser Lys Lys Val Ser Leu Thr
    370             375             380

Cys Leu Val Thr Asn Phe Phe Ser Glu Ala Ile Ser Val Glu Trp Glu
385             390             395             400

Arg Asn Gly Glu Leu Glu Gln Asp Tyr Lys Asn Thr Pro Pro Ile Leu
            405             410             415

Asp Ser Asp Gly Thr Tyr Phe Leu Tyr Ser Lys Leu Thr Val Asp Thr
            420             425             430

Asp Ser Trp Leu Gln Gly Glu Ile Phe Thr Cys Ser Val Val His Glu
            435             440             445

Ala Leu His Asn His His Thr Gln Lys Asn Leu Ser Arg Ser Pro Gly
    450             455             460

Lys
465

<210> SEQ ID NO 3
<211> LENGTH: 1386

<212> TYPE: DNA
<213> ORGANISM: Artificial sequence
<220> FEATURE:
<223> OTHER INFORMATION: Heavy chain DNA sequence of 27.18

<400> SEQUENCE: 3

```
atgaacttct ggctcagctt gattttcctt gtccttgttt taaaaggtgt ccagtgtgaa     60
gtgaagctgg tggagtctgg gggaggctta gtgcagcctg agggtccct gaaactctcc     120 tgtgcaacct ctggattcac tttcagtcac tattacatgt attgggttcg ccagactcca     180
gagaagaggc tggagtgggt cgcatacatt agtaatgatg gtgataacac ctattatcca     240
gacactataa ggggccgatt caccatctcc agagacaatg ccaggaacac cctgtacctg     300
caaatgagcc gtctgaagtc tgaggacaca gccatgtatt actgtgcaag agggaagtac     360
gacggggcct ggtttgctta ctggggccaa gggactctgg tcactgtctc tgcagccaaa     420
acgacacccc catctgtcta tccactggcc cctggatctg ctgcccaaac taactccatg     480
gtgaccctgg gatgcctggt caagggctat ttccctgagc cagtgacagt gacctggaac     540
tctggatccc tgtccagcgg tgtgcacacc ttcccagctg tcctggagtc tgacctctac     600
actctgagca gctcagtgac tgtccctcc agcctcggc ccagcgagac cgtcacctgc     660
aacgttgccc acccggccag cagcaccaag gtggacaaga aaattgtgcc cagggattgt     720
ggttgtaagc cttgcatatg tacagtccca gaagtatcat ctgtcttcat cttcccccca     780
aagcccaagg atgtgctcac cattactctg actcctaagg tcacgtgtgt tgtggtagac     840
atcagcaagg atgatcccga ggtccagttc agctggtttg tagatgatgt ggaggtgcac     900
acagctcaga cgcaacccg ggaggagcag ttcaacagca ctttccgctc agtcagtgaa     960
cttcccatca tgcaccagga ctggctcaat ggcaaggagt tcaaatgcag ggtcaacagt     1020
gcagctttcc ctgcccccat cgagaaaacc atctccaaaa ccaaaggcag accgaaggct     1080
ccacaggtgt acaccattcc acctcccaag gagcagatgg ccaaggataa agtcagtctg     1140
acctgcatga taacagactt cttccctgaa gacattactg tggagtggca gtggaatggg     1200
cagccagcgg agaactacaa gaacactcag cccatcatga acacgaatgg ctcttacttc     1260
gtctacagca agctcaatgt gcagaagagc aactgggagg caggaaatac tttcacctgc     1320
tctgtgttac atgagggcct gcacaaccac catactgaga agagcctctc ccactctcct     1380
ggtaaa                                                                1386
```

<210> SEQ ID NO 4
<211> LENGTH: 461
<212> TYPE: PRT
<213> ORGANISM: Artificial sequence
<220> FEATURE:
<223> OTHER INFORMATION: Heavy chain protein sequence of 27.18

<400> SEQUENCE: 4

```
Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

His Tyr Tyr Met Tyr Trp Val Arg Gln Thr Pro Glu Lys Arg Leu Glu
    50                  55                  60

Trp Val Ala Tyr Ile Ser Asn Asp Gly Asp Asn Thr Tyr Tyr Pro Asp
65                  70                  75                  80
```

-continued

```
Thr Ile Arg Gly Arg Phe Thr Ile Ser Arg Asp Asn Ala Arg Asn Thr
              85                  90                  95

Leu Tyr Leu Gln Met Ser Arg Leu Lys Ser Glu Asp Thr Ala Met Tyr
             100                 105                 110

Tyr Cys Ala Arg Gly Lys Tyr Asp Gly Ala Trp Phe Ala Tyr Trp Gly
             115                 120                 125

Gln Gly Thr Leu Val Thr Val Ser Ala Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
             165                 170                 175

Thr Trp Asn Ser Gly Ser Leu Ser Ser Gly Val His Thr Phe Pro Ala
             180                 185                 190

Val Leu Glu Ser Asp Leu Tyr Thr Leu Ser Ser Ser Val Thr Val Pro
             195                 200                 205

Ser Ser Pro Arg Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
             245                 250                 255

Phe Pro Pro Lys Pro Lys Asp Val Leu Thr Ile Thr Leu Thr Pro Lys
             260                 265                 270

Val Thr Cys Val Val Val Asp Ile Ser Lys Asp Asp Pro Glu Val Gln
             275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
             325                 330                 335

Val Asn Ser Ala Ala Phe Pro Ala Pro Ile Glu Lys Thr Ile Ser Lys
             340                 345                 350

Thr Lys Gly Arg Pro Lys Ala Pro Gln Val Tyr Thr Ile Pro Pro Pro
             355                 360                 365

Lys Glu Gln Met Ala Lys Asp Lys Val Ser Leu Thr Cys Met Ile Thr
    370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asn Thr Asn Gly
             405                 410                 415

Ser Tyr Phe Val Tyr Ser Lys Leu Asn Val Gln Lys Ser Asn Trp Glu
             420                 425                 430

Ala Gly Asn Thr Phe Thr Cys Ser Val Leu His Glu Gly Leu His Asn
             435                 440                 445

His His Thr Glu Lys Ser Leu Ser His Ser Pro Gly Lys
    450                 455                 460
```

<210> SEQ ID NO 5
<211> LENGTH: 714
<212> TYPE: DNA
<213> ORGANISM: Artificial sequence
<220> FEATURE:

-continued

<223> OTHER INFORMATION: Light chain DNA sequence FG27.10

<400> SEQUENCE: 5

```
atgaagttgc ctgttaggct gttggtgctg atgttctgga ttcctgcttc catcagtgat      60
gttttgatga cccaaactcc actctccctg cctgtcagtc ttggagatca agcctccatc     120
tcttgcagat ctagtcagat cattgtacat actaatggaa acacctattt agaatggtac     180
ctgcagaaac aggccagtc tccaaacctc ctgatctaca agtttccaa ccgattttct     240 ggggtcccag acaggttcag tggcagtgga tcagggacag atttcacact caagatcagc     300
agagtggagg ctgaggatct gggagtttat tactgctttc aaggttcaca tgttccattc     360
acgttcggct cggggacaaa gttggaaata aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600 agcacctca cgttgaccaa ggacgagtat gaacgacata acagctatac ctgtgaggcc     660
actcacaaga catcaacttc acccattgtc aagagcttca acaggaatga gtgt          714
```

<210> SEQ ID NO 6
<211> LENGTH: 238
<212> TYPE: PRT
<213> ORGANISM: Artificial sequence
<220> FEATURE:
<223> OTHER INFORMATION: Light chain protein sequence FG27.10

<400> SEQUENCE: 6

```
Met Lys Leu Pro Val Arg Leu Leu Val Leu Met Phe Trp Ile Pro Ala
1               5                   10                  15

Ser Ile Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ile Ile
        35                  40                  45

Val His Thr Asn Gly Asn Thr Tyr Leu Glu Trp Tyr Leu Gln Lys Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220
```

Ser Thr Ser Pro Ile Val Lys Ser Phe Asn Arg Asn Glu Cys
225                 230                 235

<210> SEQ ID NO 7
<211> LENGTH: 1404
<212> TYPE: DNA
<213> ORGANISM: Artificial sequence
<220> FEATURE:
<223> OTHER INFORMATION: Heavy chain DNA sequence CH27.10

<400> SEQUENCE: 7
atgaacttct ggctcagctt gattttcctt gtccttgttt taaaaggtgt ccagtgtgaa      60
gtgaagctgg tggagtctgg gggaggctta gtgcagcctg agggtccct gaaactctcc     120 tgtgcaacct ctggattcac tttcagtcac tattacatgt attgggttcg ccagactcca     180
gagaagaggc tggagtgggt cgcatacatt agtaatgatg gtgataacac ctattatcca     240
gacactataa ggggccgatt caccatctcc agagacaatg ccaggaacac cctgtacctg     300
caaatgagcc gtctgaagtc tgaggacaca gccatgtatt actgtgcaag agggaagtac     360
gacgggGcct ggtttgctta ctggggccaa gggactctgg tcactgtctc tagcgcttcc     420
accaagggcc catcggtctt ccccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttccggctg tcctacagtc ctcaggactc     600
tactccctca gcagcgtggt gaccgtgccc tccagcagct tgggcaccca gacctacatc     660
tgcaacgtga atcacaagcc cagcaacacc aaggtggaca gaaagttga gcccaaatct     720 tgtgacaaaa ctcacacatg cccaccgtgc ccagcacctg aactcctggg gggaccgtca     780
gtcttcctct ccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca aagccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga tgagctgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                           1404

<210> SEQ ID NO 8
<211> LENGTH: 467
<212> TYPE: PRT
<213> ORGANISM: Artificial sequence
<220> FEATURE:
<223> OTHER INFORMATION: Heavy chain protein sequence CH27.10

<400> SEQUENCE: 8

Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe

-continued

```
              35                    40                    45
His Tyr Tyr Met Tyr Trp Val Arg Gln Thr Pro Glu Lys Arg Leu Glu
    50                    55                    60

Trp Val Ala Tyr Ile Ser Asn Asp Gly Asp Asn Thr Tyr Tyr Pro Asp
65                    70                    75                    80

Thr Ile Arg Gly Arg Phe Thr Ile Ser Arg Asp Asn Ala Arg Asn Thr
                85                    90                    95

Leu Tyr Leu Gln Met Ser Arg Leu Lys Ser Glu Asp Thr Ala Met Tyr
            100                   105                   110

Tyr Cys Ala Arg Gly Lys Tyr Asp Gly Ala Trp Phe Ala Tyr Trp Gly
            115                   120                   125

Gln Gly Thr Leu Val Thr Val Ser Ser Ala Ser Thr Lys Gly Pro Ser
    130                   135                   140

Val Phe Pro Leu Ala Pro Ser Ser Lys Ser Thr Ser Gly Gly Thr Ala
145                   150                   155                   160

Ala Leu Gly Cys Leu Val Lys Asp Tyr Phe Pro Glu Pro Val Thr Val
                165                   170                   175

Ser Trp Asn Ser Gly Ala Leu Thr Ser Gly Val His Thr Phe Pro Ala
                180                   185                   190

Val Leu Gln Ser Ser Gly Leu Tyr Ser Leu Ser Ser Val Val Thr Val
            195                   200                   205

Pro Ser Ser Ser Leu Gly Thr Gln Thr Tyr Ile Cys Asn Val Asn His
    210                   215                   220

Lys Pro Ser Asn Thr Lys Val Asp Lys Lys Val Glu Pro Lys Ser Cys
225                   230                   235                   240

Asp Lys Thr His Thr Cys Pro Pro Cys Pro Ala Pro Glu Leu Leu Gly
                245                   250                   255

Gly Pro Ser Val Phe Leu Phe Pro Pro Lys Pro Lys Asp Thr Leu Met
                260                   265                   270

Ile Ser Arg Thr Pro Glu Val Thr Cys Val Val Val Asp Val Ser His
            275                   280                   285

Glu Asp Pro Glu Val Lys Phe Asn Trp Tyr Val Asp Gly Val Glu Val
    290                   295                   300

His Asn Ala Lys Thr Lys Pro Arg Glu Glu Gln Tyr Asn Ser Thr Tyr
305                   310                   315                   320

Arg Val Val Ser Val Leu Thr Val Leu His Gln Asp Trp Leu Asn Gly
                325                   330                   335

Lys Glu Tyr Lys Cys Lys Val Ser Asn Lys Ala Leu Pro Ala Pro Ile
            340                   345                   350

Glu Lys Thr Ile Ser Lys Ala Lys Gly Gln Pro Arg Glu Pro Gln Val
            355                   360                   365

Tyr Thr Leu Pro Pro Ser Arg Asp Glu Leu Thr Lys Asn Gln Val Ser
    370                   375                   380

Leu Thr Cys Leu Val Lys Gly Phe Tyr Pro Ser Asp Ile Ala Val Glu
385                   390                   395                   400

Trp Glu Ser Asn Gly Gln Pro Glu Asn Asn Tyr Lys Thr Thr Pro Pro
                405                   410                   415

Val Leu Asp Ser Asp Gly Ser Phe Phe Leu Tyr Ser Lys Leu Thr Val
                420                   425                   430

Asp Lys Ser Arg Trp Gln Gln Gly Asn Val Phe Ser Cys Ser Val Met
            435                   440                   445

His Glu Ala Leu His Asn His Tyr Thr Gln Lys Ser Leu Ser Leu Ser
    450                   455                   460
```

-continued

Pro Gly Lys
465

<210> SEQ ID NO 9
<211> LENGTH: 714
<212> TYPE: DNA
<213> ORGANISM: Artificial sequence
<220> FEATURE:
<223> OTHER INFORMATION: CH27.10 light chain DNA sequence

<400> SEQUENCE: 9
atgaagttgc ctgttaggct gttggtgctg atgttctgga ttcctgcttc catcagtgat      60
gttttgatga cccaaactcc actctccctg cctgtcagtc ttggagatca agcctccatc     120
tcttgcagat ctagtcagat cattgtacat actaatggaa acacctattt agaatggtac     180
ctgcagaaac caggccagtc tccaaacctc ctgatctaca agtttccaa ccgatttct      240 ggggtcccag acaggttcag tggcagtgga tcagggacag atttcacact caagatcagc     300
agagtggagg ctgaggatct gggagtttat tactgctttc aaggttcaca tgttccattc     360
acgttcggct cggggacaaa gttggaaata aaacgtacgg tagcggcccc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc     660 acccatcagg cctgagctc gcccgtcaca aagagcttca caggggagaa gtgt           714

<210> SEQ ID NO 10
<211> LENGTH: 238
<212> TYPE: PRT
<213> ORGANISM: Artificial sequence
<220> FEATURE:
<223> OTHER INFORMATION: CH27.10 light chain protein sequence

<400> SEQUENCE: 10

Met Lys Leu Pro Val Arg Leu Leu Val Leu Met Phe Trp Ile Pro Ala
1               5                  10                  15

Ser Ile Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ile Ile
        35                  40                  45

Val His Thr Asn Gly Asn Thr Tyr Leu Glu Trp Tyr Leu Gln Lys Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn

-continued

```
                    165              170              175
Ala Leu Gln Ser Gly Asn Ser Gln Glu Ser Val Thr Glu Gln Asp Ser
            180              185              190

Lys Asp Ser Thr Tyr Ser Leu Ser Ser Thr Leu Thr Leu Ser Lys Ala
            195              200              205

Asp Tyr Glu Lys His Lys Val Tyr Ala Cys Glu Val Thr His Gln Gly
            210              215              220

Leu Ser Ser Pro Val Thr Lys Ser Phe Asn Arg Gly Glu Cys
225              230              235
```

```
<210> SEQ ID NO 11
<211> LENGTH: 357
<212> TYPE: DNA
<213> ORGANISM: Artificial sequence
<220> FEATURE:
<223> OTHER INFORMATION: FG27 RHA

<400> SEQUENCE: 11
caggtccagc tggtcgaatc aggggggaggc gtcgtgcagc ccggaaggtc actgagactg      60
tcatgtgccg catcagggtt tactttctca cactactata tgtactgggt gcgacaggct     120
ccaggcaagg gactggagtg ggtcgcatat atcagcaacg acggcgataa tacttactat     180
cctgacacca tccggggggag attcacaatc tctagagata acagtaagaa cactctgtac     240
ctgcagatga actctctgag ggcagaagac accgccgtgt actattgcgc cgcgggaaa     300 tacgatggag cctggtttgc ttattgggga caggggcaccc tggtgacagt cagctcc     357
```

```
<210> SEQ ID NO 12
<211> LENGTH: 119
<212> TYPE: PRT
<213> ORGANISM: Artificial sequence
<220> FEATURE:
<223> OTHER INFORMATION: FG27 RHA

<400> SEQUENCE: 12

Gln Val Gln Leu Val Glu Ser Gly Gly Gly Val Val Gln Pro Gly Arg
1               5              10              15

Ser Leu Arg Leu Ser Cys Ala Ala Ser Gly Phe Thr Phe Ser His Tyr
            20              25              30

Tyr Met Tyr Trp Val Arg Gln Ala Pro Gly Lys Gly Leu Glu Trp Val
        35              40              45

Ala Tyr Ile Ser Asn Asp Gly Asp Asn Thr Tyr Tyr Pro Asp Thr Ile
    50              55              60

Arg Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Gly Lys Tyr Asp Gly Ala Trp Phe Ala Tyr Trp Gly Gln Gly
            100             105             110

Thr Leu Val Thr Val Ser Ser
        115
```

```
<210> SEQ ID NO 13
<211> LENGTH: 990
<212> TYPE: DNA
<213> ORGANISM: Artificial sequence
<220> FEATURE:
<223> OTHER INFORMATION: HuG1 DNA sequence

<400> SEQUENCE: 13
```

-continued

```
gcctccacca agggcccttc cgtgttccct ctggcccctt cctccaagtc cacctccggc      60
ggcaccgccg ctctgggctg cctggtgaag gactacttcc ctgagcctgt gaccgtgtcc     120
tggaactctg gcgccctgac cagcggcgtg cacaccttcc ctgccgtgct gcagtcctcc     180
ggcctgtact ccctgtcctc cgtggtgacc gtgccttcct cctccctggg cacccagacc     240
tacatctgca acgtgaacca caagccttcc aacaccaagg tggacaagaa ggtggagcct     300
aagtcctgcg acaagaccca cacgtgccct ccatgcccag ctcccgagct gctgggcgga     360
ccaagcgtgt tcctgttccc tcctaagcct aaggacaccc tgatgatctc ccggacccct     420
gaggtgacgt gcgtggtggt ggacgtgtcc cacgaggacc cagaggtgaa gttcaattgg     480
tacgtggacg gcgtggaggt gcacaacgcc aagaccaagc ctcgggagga acagtacaac     540
tccacctacc gggtggtgtc tgtgctgacc gtgctgcacc aggactggct gaacggcaag     600
gaatacaagt gcaaagtctc caacaaggcc ctgcctgccc ccatcgaaaa gaccatctcc     660
aaggccaagg gccagcctcg cgagcctcag gtgtacaccc tgcctccaag cagggaggaa     720
atgaccaaga accaggtgtc cctgacctgt ctggtgaagg gcttctaccc ttccgatatc     780
gccgtggagt gggagtccaa cggccagcct gagaacaact acaagaccac ccctcctgtg     840
ctggactccg acggctcctt cttcctgtac tccaagctga ccgtggacaa gtcccggtgg     900
cagcagggca acgtgttctc ctgctccgtg atgcacgagg ccctgcacaa ccactacacc     960
cagaagagcc tctccctgtc cccgggtaaa                                       990
```

```
<210> SEQ ID NO 14
<211> LENGTH: 330
<212> TYPE: PRT
<213> ORGANISM: Artificial sequence
<220> FEATURE:
<223> OTHER INFORMATION: HuG1 protein sequence

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

-continued

```
              180              185              190
His Gln Asp Trp Leu Asn Gly Lys Glu Tyr Lys Cys Lys Val Ser Asn
         195              200              205
Lys Ala Leu Pro Ala Pro Ile Glu Lys Thr Ile Ser Lys Ala Lys Gly
         210              215              220
Gln Pro Arg Glu Pro Gln Val Tyr Thr Leu Pro Pro Ser Arg Glu Glu
225              230              235              240
Met Thr Lys Asn Gln Val Ser Leu Thr Cys Leu Val Lys Gly Phe Tyr
              245              250              255
Pro Ser Asp Ile Ala Val Glu Trp Glu Ser Asn Gly Gln Pro Glu Asn
              260              265              270
Asn Tyr Lys Thr Thr Pro Pro Val Leu Asp Ser Asp Gly Ser Phe Phe
         275              280              285
Leu Tyr Ser Lys Leu Thr Val Asp Lys Ser Arg Trp Gln Gln Gly Asn
         290              295              300
Val Phe Ser Cys Ser Val Met His Glu Ala Leu His Asn His Tyr Thr
305              310              315              320
Gln Lys Ser Leu Ser Leu Ser Pro Gly Lys
              325              330
```

```
<210> SEQ ID NO 15
<211> LENGTH: 396
<212> TYPE: DNA
<213> ORGANISM: Artificial sequence
<220> FEATURE:
<223> OTHER INFORMATION: FG27 RKC DNA sequence

<400> SEQUENCE: 15
atggaagccc cagcgcagct tctcttcctc ctgctactct ggctccctga taccaccgga        60
gacgtcgtga tgacccagag cccactgagc ctgcctgtga cacccggcga gcccgcaagt       120
atttcctgta aagttccca gattatcgtc cacactaacg ggaataccta cctggagtgg       180
tatctgcaga agcccggcca gagtcctcag ctgctgatct acaaagtgag taaccggttc       240
tcaggagtcc cagaccggtt cagcggctcc gggtctggaa ccgatttcac actgaagatt       300
agcagggtgg aggccgaaga cgtgggagtc tactattgct ttcagggctc ccatgtcccc       360
ttcacatttg gccaggggac caagctggaa atcaaa                                 396
```

```
<210> SEQ ID NO 16
<211> LENGTH: 132
<212> TYPE: PRT
<213> ORGANISM: Artificial sequence
<220> FEATURE:
<223> OTHER INFORMATION: FG27 RKC protein sequence

<400> SEQUENCE: 16

Met Glu Ala Pro Ala Gln Leu Leu Phe Leu Leu Leu Leu Trp Leu Pro
1              5              10              15
Asp Thr Thr Gly Asp Val Val Met Thr Gln Ser Pro Leu Ser Leu Pro
              20              25              30
Val Thr Pro Gly Glu Pro Ala Ser Ile Ser Cys Arg Ser Ser Gln Ile
         35              40              45
Ile Val His Thr Asn Gly Asn Thr Tyr Leu Glu Trp Tyr Leu Gln Lys
         50              55              60
Pro Gly Gln Ser Pro Gln Leu Leu Ile Tyr Lys Val Ser Asn Arg Phe
65              70              75              80
Ser Gly Val Pro Asp Arg Phe Ser Gly Ser Gly Ser Gly Thr Asp Phe
```

```
                85                   90                   95
Thr Leu Lys Ile Ser Arg Val Glu Ala Glu Asp Val Gly Val Tyr Tyr
            100                 105                 110
Cys Phe Gln Gly Ser His Val Pro Phe Thr Phe Gly Gln Gly Thr Lys
        115                 120                 125
Leu Glu Ile Lys
    130

<210> SEQ ID NO 17
<211> LENGTH: 321
<212> TYPE: DNA
<213> ORGANISM: Artificial sequence
<220> FEATURE:
<223> OTHER INFORMATION: HuK DNA sequence

<400> SEQUENCE: 17
agaactgtgg cagcaccaag cgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 18
<211> LENGTH: 107
<212> TYPE: PRT
<213> ORGANISM: Artificial sequence
<220> FEATURE:
<223> OTHER INFORMATION: HuK protein sequence

<400> SEQUENCE: 18

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 19
<211> LENGTH: 714
<212> TYPE: DNA
<213> ORGANISM: Artificial sequence
<220> FEATURE:
<223> OTHER INFORMATION: 27 Light chain DNA sequence (variable region +
      Kappa constant)

<400> SEQUENCE: 19
atgaagttgc ctgttaggct gttggtgctg atgttctgga ttcctgcttc catcagtgat      60
gttttgatga cccaaactcc actctccctg cctgtcagtc ttggagatca agcctccatc     120
```

-continued

```
tcttgcagat ctagtcagat cattgtacat actaatggaa acacctattt agaatggtac       180
ctgcagaaac caggccagtc tccaaacctc ctgatctaca aagtttccaa ccgattttct       240
ggggtcccag acaggttcag tggcagtgga tcagggacag atttcacact caagatcagc       300
agagtggagg ctgaggatct gggagtttat tactgctttc aaggttcaca tgttccattc       360
acgttcggct cggggacaaa gttggaaata aaacgtacgg tagcggcccc atctgtcttc       420
atcttcccgc catctgatga gcagttgaaa tctggaactg cctctgttgt gtgcctgctg       480
aataacttct atcccagaga ggccaaagta cagtggaagg tggataacgc cctccaatcg       540
ggtaactccc aggagagtgt cacagagcag gacagcaagg acagcaccta cagcctcagc       600
agcaccctga cgctgagcaa agcagactac gagaaacaca aagtctacgc ctgcgaagtc       660
acccatcagg gcctgagctc gcccgtcaca aagagcttca acaggggaga gtgt            714
```

```
<210> SEQ ID NO 20
<211> LENGTH: 238
<212> TYPE: PRT
<213> ORGANISM: Artificial sequence
<220> FEATURE:
<223> OTHER INFORMATION: 27 Light chain protein sequence (variable
      region + Kappa constant)

<400> SEQUENCE: 20

Met Lys Leu Pro Val Arg Leu Leu Val Leu Met Phe Trp Ile Pro Ala
1               5                   10                  15

Ser Ile Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ile Ile
        35                  40                  45

Val His Thr Asn Gly Asn Thr Tyr Leu Glu Trp Tyr Leu Gln Lys Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys
225                 230                 235
```

```
<210> SEQ ID NO 21
<211> LENGTH: 1404
```

```
<212> TYPE: DNA
<213> ORGANISM: Artificial sequence
<220> FEATURE:
<223> OTHER INFORMATION: Heavy chain DNA sequence of i27v1 (variable +
      'improved' v1 constant region)

<400> SEQUENCE: 21
atgaacttct ggctcagctt gattttcctt gtccttgttt taaaaggtgt ccagtgtgaa      60
gtgaagctgg tggagtctgg gggaggctta gtgcagcctg gagggtccct gaaactctcc     120
tgtgcaacct ctggattcac tttcagtcac tattacatgt attgggttcg ccagactcca     180
gagaagaggc tggagtgggt cgcatacatt agtaatgatg gtgataacac ctattatcca     240
gacactataa ggggccgatt caccatctcc agagacaatg ccaggaacac cctgtacctg     300
caaatgagcc gtctgaagtc tgaggacaca gccatgtatt actgtgcaag agggaagtac     360 gacgggcct ggtttgctta ctggggccaa gggactctgg tcactgtctc tagcgcttcc     420
accaagggcc atcggtctt cccctggca ccctcctcca agagcacctc tgggggcaca     480
gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct tgggcaccca gacctacatc     660
tgcaacgtga atcacaagcc cagcaacacc aaggtggaca gaaagttga gcccaaatct     720 tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcatac agcctggaca gcccccgtg aagagcagta caacagtacc     960
taccgagtgg tcagtgtcct caccgtcctg caccaggact ggctgaatgg caaggagtac    1020
aagtgcaagg tctccaacaa agccctccca gccccatcg agaaaaccat ctccaaaccc    1080
aaaggaagag cccagacacc tcaagtatac accatacccc cacctcgtga caaatgtcc    1140 aagaagaagg ttagtctgac ctgcctggtc accaacttct tctctgaagc catcagtgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                          1404

<210> SEQ ID NO 22
<211> LENGTH: 468
<212> TYPE: PRT
<213> ORGANISM: Artificial sequence
<220> FEATURE:
<223> OTHER INFORMATION: Heavy chain Protein sequence of i27v1
      (variable + 'improved' v1 constant region)

<400> SEQUENCE: 22

Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser His Tyr Tyr Met Tyr Trp Val Arg Gln Thr Pro Glu Lys Arg Leu
    50                  55                  60
```

-continued

```
Glu Trp Val Ala Tyr Ile Ser Asn Asp Gly Asp Asn Thr Tyr Tyr Pro
65                  70                  75                  80

Asp Thr Ile Arg Gly Arg Phe Thr Ile Ser Arg Asp Asn Ala Arg Asn
                85                  90                  95

Thr Leu Tyr Leu Gln Met Ser Arg Leu Lys Ser Glu Asp Thr Ala Met
            100                 105                 110

Tyr Tyr Cys Ala Arg Gly Lys Tyr Asp Gly Ala Trp Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
    290                 295                 300

Val His Thr Ala Trp Thr Gln Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Pro Lys Gly Arg Ala Gln Thr Pro Gln
            355                 360                 365

Val Tyr Thr Ile Pro Pro Arg Glu Gln Met Ser Lys Lys Lys Val
    370                 375                 380

Ser Leu Thr Cys Leu Val Thr Asn Phe Phe Ser Glu Ala Ile Ser Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465
```

```
<210> SEQ ID NO 23
<211> LENGTH: 1404
<212> TYPE: DNA
<213> ORGANISM: Artificial Sequence
<220> FEATURE:
<223> OTHER INFORMATION: Heavy chain DNA sequence of FG27.10

<400> SEQUENCE: 23
atgaacttct ggctcagctt gattttcctt gtccttgttt taaaaggtgt ccagtgtgaa      60
gtgaagctgg tggagtctgg gggaggctta gtgcagcctg aggggtccct gaaactctcc     120
tgtgcaacct ctggattcac tttcagtcac tattacatgt attgggttcg ccagactcca     180
gagaagaggc tggagtgggt cgcatacatt agtaatgatg gtgataacac ctattatcca     240
gacactataa ggggccgatt caccatctcc agagacaatg ccaggaacac cctgtacctg     300
caaatgagcc gtctgaagtc tgaggacaca gccatgtatt actgtgcaag agggaagtac     360
gacggggcct ggtttgctta ctggggccaa gggactctgg tcactgtctc tgcagctaca     420
acaacagccc catctgtcta tcccttggtc cctggctgca gtgacacatc tggatcctcg     480
gtgacactgg gatgccttgt caaaggctac ttccctgagc cggtaactgt aaaatggaac     540
tatggagccc gtccagcggg tgtgcgcaca gtctcatctg tcctgcagtc tgggttctat     600
tccctcagca gcttggtgac tgtaccctcc agcacctggc ccagccagac tgtcatctgc     660
aacgtagccc acccagccag caagactgag ttgatcaaga aatcgagcc tagaataccc     720 aagcccagta cccccccagg ttcttcatgc ccacctggta acatcttggg tggaccatcc     780
gtcttcatct tccccccaaa gcccaaggat gcactcatga tctccctaac ccccaaggtt     840
acgtgtgtgg tggtggatgt gagcgaggat gacccagatg tccatgtcag ctggtttgtg     900
gacaacaaag aagtacacac agcctggaca cagccccgtg aagctcagta caacagtacc     960
ttccgagtgg tcagtgccct ccccatccag caccaggact ggatgagggg caaggagttc    1020
aaatgcaagg tcaacaacaa agccctccca gcccccatcg agagaaccat ctcaaaaccc    1080
aaaggaagag cccagacacc tcaagtatac accataccc cacctcgtga acaaatgtcc     1140
aagaagaagg ttagtctgac ctgcctggtc accaacttct tctctgaagc catcagtgtg    1200
gagtgggaaa ggaacggaga actggagcag gattacaaga cactccacc catcctggac     1260 tcagatggga cctacttcct ctacagcaag ctcactgtgg atacagacag ttggttgcaa    1320
ggagaaattt ttacctgctc cgtggtgcat gaggctctcc ataaccacca cacacagaag    1380
aacctgtctc gctcccctgg taaa                                            1404

<210> SEQ ID NO 24
<211> LENGTH: 468
<212> TYPE: PRT
<213> ORGANISM: Artificial Sequence
<220> FEATURE:
<223> OTHER INFORMATION: Heavy chain protein sequence of FG27.10

<400> SEQUENCE: 24

Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser His Tyr Tyr Met Tyr Trp Val Arg Gln Thr Pro Glu Lys Arg Leu
    50                  55                  60
```

-continued

```
Glu Trp Val Ala Tyr Ile Ser Asn Asp Gly Asp Asn Thr Tyr Tyr Pro
65                  70                  75                  80

Asp Thr Ile Arg Gly Arg Phe Thr Ile Ser Arg Asp Asn Ala Arg Asn
                85                  90                  95

Thr Leu Tyr Leu Gln Met Ser Arg Leu Lys Ser Glu Asp Thr Ala Met
            100                 105                 110

Tyr Tyr Cys Ala Arg Gly Lys Tyr Asp Gly Ala Trp Phe Ala Tyr Trp
        115                 120                 125

Gly Gln Gly Thr Leu Val Thr Val Ser Ala Ala Thr Thr Thr Ala Pro
    130                 135                 140

Ser Val Tyr Pro Leu Val Pro Gly Cys Ser Asp Thr Ser Gly Ser Ser
145                 150                 155                 160

Val Thr Leu Gly Cys Leu Val Lys Gly Tyr Phe Pro Glu Pro Val Thr
                165                 170                 175

Val Lys Trp Asn Tyr Gly Ala Leu Ser Ser Gly Val Arg Thr Val Ser
            180                 185                 190

Ser Val Leu Gln Ser Gly Phe Tyr Ser Leu Ser Ser Leu Val Thr Val
            195                 200                 205

Pro Ser Ser Thr Trp Pro Ser Gln Thr Val Ile Cys Asn Val Ala His
    210                 215                 220

Pro Ala Ser Lys Thr Glu Leu Ile Lys Arg Ile Glu Pro Arg Ile Pro
225                 230                 235                 240

Lys Pro Ser Thr Pro Pro Gly Ser Ser Cys Pro Pro Gly Asn Ile Leu
                245                 250                 255

Gly Gly Pro Ser Val Phe Ile Phe Pro Pro Lys Pro Lys Asp Ala Leu
            260                 265                 270

Met Ile Ser Leu Thr Pro Lys Val Thr Cys Val Val Val Asp Val Ser
        275                 280                 285

Glu Asp Asp Pro Asp Val His Val Ser Trp Phe Val Asp Asn Lys Glu
    290                 295                 300

Val His Thr Ala Trp Thr Gln Pro Arg Glu Ala Gln Tyr Asn Ser Thr
305                 310                 315                 320

Phe Arg Val Val Ser Ala Leu Pro Ile Gln His Gln Asp Trp Met Arg
                325                 330                 335

Gly Lys Glu Phe Lys Cys Lys Val Asn Asn Lys Ala Leu Pro Ala Pro
            340                 345                 350

Ile Glu Arg Thr Ile Ser Lys Pro Lys Gly Arg Ala Gln Thr Pro Gln
        355                 360                 365

Val Tyr Thr Ile Pro Pro Pro Arg Glu Gln Met Ser Lys Lys Lys Val
    370                 375                 380

Ser Leu Thr Cys Leu Val Thr Asn Phe Phe Ser Glu Ala Ile Ser Val
385                 390                 395                 400

Glu Trp Glu Arg Asn Gly Glu Leu Glu Gln Asp Tyr Lys Asn Thr Pro
                405                 410                 415

Pro Ile Leu Asp Ser Asp Gly Thr Tyr Phe Leu Tyr Ser Lys Leu Thr
            420                 425                 430

Val Asp Thr Asp Ser Trp Leu Gln Gly Glu Ile Phe Thr Cys Ser Val
            435                 440                 445

Val His Glu Ala Leu His Asn His His Thr Gln Lys Asn Leu Ser Arg
    450                 455                 460

Ser Pro Gly Lys
465
```

```
<210> SEQ ID NO 25
<211> LENGTH: 462
<212> TYPE: PRT
<213> ORGANISM: Artificial Sequence
<220> FEATURE:
<223> OTHER INFORMATION: Heavy chain protein sequence of FG27.18

<400> SEQUENCE: 25

Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser His Tyr Tyr Met Tyr Trp Val Arg Gln Thr Pro Glu Lys Arg Leu
    50                  55                  60

Glu Trp Val Ala Tyr Ile Ser Asn Asp Gly Asp Asn Thr Tyr Tyr Pro
65                  70                  75                  80

Asp Thr Ile Arg Gly Arg Phe Thr Ile Ser Arg Asp Asn Ala Arg Asn
                85                  90                  95

Thr Leu Tyr Leu Gln Met Ser Arg Leu Lys Ser Glu Asp Thr Ala Met
            100                 105                 110

Tyr Tyr Cys Ala Arg Gly Lys Tyr Asp Gly Ala Trp Phe Ala Tyr Trp
        115                 120                 125

Gly Gln Gly Thr Leu Val Thr Val Ser Ala Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Glu Ser Asp Leu Tyr Thr Leu Ser Ser Ser Val Thr Val
            195                 200                 205

Pro Ser Ser Pro Arg Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
    290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
                340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
```

-continued

```
          370              375              380

Thr Asp Phe Phe Pro Glu Asp Ile Thr Val Glu Trp Gln Trp Asn Gly
385              390              395              400

Gln Pro Ala Glu Asn Tyr Lys Asn Thr Gln Pro Ile Met Asn Thr Asn
              405              410              415

Gly Ser Tyr Phe Val Tyr Ser Lys Leu Asn Val Gln Lys Ser Asn Trp
              420              425              430

Glu Ala Gly Asn Thr Phe Thr Cys Ser Val Leu His Glu Gly Leu His
              435              440              445

Asn His His Thr Glu Lys Ser Leu Ser His Ser Pro Gly Lys
    450              455              460

<210> SEQ ID NO 26
<211> LENGTH: 468
<212> TYPE: PRT
<213> ORGANISM: Artificial Sequence
<220> FEATURE:
<223> OTHER INFORMATION: Heavy chain protein sequence of Ch27.10

<400> SEQUENCE: 26

Met Asn Phe Trp Leu Ser Leu Ile Phe Leu Val Leu Val Leu Lys Gly
1              5               10               15

Val Gln Cys Glu Val Lys Leu Val Glu Ser Gly Gly Gly Leu Val Gln
              20               25               30

Pro Gly Gly Ser Leu Lys Leu Ser Cys Ala Thr Ser Gly Phe Thr Phe
              35               40               45

Ser His Tyr Tyr Met Tyr Trp Val Arg Gln Thr Pro Glu Lys Arg Leu
    50               55               60

Glu Trp Val Ala Tyr Ile Ser Asn Asp Gly Asp Asn Thr Tyr Tyr Pro
65               70               75               80

Asp Thr Ile Arg Gly Arg Phe Thr Ile Ser Arg Asp Asn Ala Arg Asn
              85               90               95

Thr Leu Tyr Leu Gln Met Ser Arg Leu Lys Ser Glu Asp Thr Ala Met
              100              105              110

Tyr Tyr Cys Ala Arg Gly Lys Tyr Asp Gly Ala Trp Phe Ala Tyr Trp
              115              120              125

Gly Gln Gly Thr Leu Val Thr Val Ser Ser Ala Ser Thr Lys Gly Pro
    130              135              140

Ser Val Phe Pro Leu Ala Pro Ser Ser Lys Ser Thr Ser Gly Gly Thr
145              150              155              160

Ala Ala Leu Gly Cys Leu Val Lys Asp Tyr Phe Pro Glu Pro Val Thr
              165              170              175

Val Ser Trp Asn Ser Gly Ala Leu Thr Ser Gly Val His Thr Phe Pro
              180              185              190

Ala Val Leu Gln Ser Ser Gly Leu Tyr Ser Leu Ser Ser Val Val Thr
              195              200              205

Val Pro Ser Ser Ser Leu Gly Thr Gln Thr Tyr Ile Cys Asn Val Asn
    210              215              220

His Lys Pro Ser Asn Thr Lys Val Asp Lys Lys Val Glu Pro Lys Ser
225              230              235              240

Cys Asp Lys Thr His Thr Cys Pro Pro Cys Pro Ala Pro Glu Leu Leu
              245              250              255

Gly Gly Pro Ser Val Phe Leu Phe Pro Pro Lys Pro Lys Asp Thr Leu
              260              265              270

Met Ile Ser Arg Thr Pro Glu Val Thr Cys Val Val Val Asp Val Ser
```

```
                275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
                340                 345                 350

Ile Glu Lys Thr Ile Ser Lys Ala Lys Gly Gln Pro Arg Glu Pro Gln
                355                 360                 365

Val Tyr Thr Leu Pro Pro Ser Arg Asp Glu Leu Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
    450                 455                 460

Ser Pro Gly Lys
465

<210> SEQ ID NO 27
<211> LENGTH: 119
<212> TYPE: PRT
<213> ORGANISM: Artificial Sequence
<220> FEATURE:
<223> OTHER INFORMATION: Heavy chain variable protein sequence of
      FG27.10

<400> SEQUENCE: 27

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser His Tyr
            20                  25                  30

Tyr Met Tyr Trp Val Arg Gln Thr Pro Glu Lys Arg Leu Glu Trp Val
            35                  40                  45

Ala Tyr Ile Ser Asn Asp Gly Asp Asn Thr Tyr Tyr Pro Asp Thr Ile
    50                  55                  60

Arg Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ala
        115

<210> SEQ ID NO 28
<211> LENGTH: 357
<212> TYPE: DNA
<213> ORGANISM: Artificial Sequence
<220> FEATURE:
```

<223> OTHER INFORMATION: Heavy chain variable DNA sequence of FG27.10

<400> SEQUENCE: 28

```
gaagtgaagc tggtggagtc tggggggaggc ttagtgcagc ctggagggtc cctgaaactc      60
tcctgtgcaa cctctggatt cactttcagt cactattaca tgtattgggt tcgccagact     120
ccagagaaga ggctggagtg ggtcgcatac attagtaatg atggtgataa cacctattat     180
ccagacacta taaggggccg attcaccatc tccagagaca tgccaggaa caccctgtac      240 ctgcaaatga gccgtctgaa gtctgaggac acagccatgt attactgtgc aagagggaag     300
tacgacgggg cctggtttgc ttactgggc caagggactc tggtcactgt ctctgca        357
```

<210> SEQ ID NO 29
<211> LENGTH: 119
<212> TYPE: PRT
<213> ORGANISM: Artificial Sequence
<220> FEATURE:
<223> OTHER INFORMATION: Heavy chain variable protein sequence of BR96

<400> SEQUENCE: 29

```
Glu Val Asn Leu Val Glu Ser Gly Gly Gly Leu Val Gln Pro Gly Gly
1               5                   10                  15

Ser Leu Lys Val Ser Cys Val Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Gln Gly Gly Asp Ile Thr Asp Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Leu Ala Asp Gly Ala Trp Phe Ala Tyr Trp Gly Gln Gly
            100                 105                 110

Thr Leu Val Thr Val Ser Val
        115
```

<210> SEQ ID NO 30
<211> LENGTH: 357
<212> TYPE: DNA
<213> ORGANISM: Artificial Sequence
<220> FEATURE:
<223> OTHER INFORMATION: Heavy chain variable DNA sequence of BR96

<400> SEQUENCE: 30

```
gaagtgaatc tggtggagtc tggggggaggc ttagtgcagc ctggagggtc cctgaaagtc      60
tcctgtgtaa cctctggatt cactttcagt gactattaca tgtattgggt tcgccagact     120
ccagagaaga ggctggagtg ggtcgcatac attagtcaag gtggtgatat aaccgactat     180
ccagacactg taaagggtcg attcaccatc tccagagaca tgccaagaa caccctgtac      240 ctgcaaatga gccgtctgaa gtctgaggac acagccatgt attactgtgc aagaggcctg     300
gccgacgggg cctggtttgc ttactgggc caagggactc tggtcacggt ctctgta        357
```

<210> SEQ ID NO 31
<211> LENGTH: 119
<212> TYPE: PRT
<213> ORGANISM: Artificial Sequence
<220> FEATURE:
<223> OTHER INFORMATION: Heavy chain variable protein sequence of H18A

<400> SEQUENCE: 31

| Glu | Val | Lys | Leu | Val | Glu | Ser | Gly | Gly | Gly | Leu | Val | Gln | Pro | Gly | Gly |
| 1 | | | | 5 | | | | | 10 | | | | | 15 | |

| Ser | Leu | Lys | Leu | Ser | Cys | Ala | Thr | Ser | Gly | Phe | Thr | Phe | Ser | Asp | Tyr |
| | | | 20 | | | | | 25 | | | | | 30 | | |

| Tyr | Met | Tyr | Trp | Val | Arg | Gln | Thr | Pro | Glu | Lys | Arg | Pro | Glu | Trp | Val |
| | | 35 | | | | | 40 | | | | | 45 | | | |

| Ala | Tyr | Ile | Ser | Asn | Gly | Gly | Asp | Ile | Pro | Tyr | Tyr | Leu | Asp | Thr | Val |
| | 50 | | | | | 55 | | | | | 60 | | | | |

| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |

| Leu | Gln | Met | Ser | Arg | Leu | Lys | Ser | Glu | Asp | Thr | Ala | Met | Tyr | Tyr | Cys |
| | | | | 85 | | | | | 90 | | | | | 95 | |

| Ala | Arg | Gly | Lys | Tyr | Asp | Gly | Ala | Trp | Phe | Ala | Tyr | Trp | Gly | Gln | Gly |
| | | | 100 | | | | | 105 | | | | | 110 | | |

| Thr | Leu | Val | Thr | Val | Ser | Ala |
| | | | 115 | | | |

<210> SEQ ID NO 32
<211> LENGTH: 357
<212> TYPE: DNA
<213> ORGANISM: Artificial Sequence
<220> FEATURE:
<223> OTHER INFORMATION: Heavy chain variable DNA sequence of H18A

<400> SEQUENCE: 32

```
gaagtgaaac tggtggagtc tggggggaggc ttagtgcagc ctggagggtc cctgaaactc      60
tcctgtgcaa cctctggatt cactttcagt gactattata tgtattgggt tcgccagact     120
ccagagaaga ggccggagtg ggtcgcatac attagtaatg gtggtgatat ccctattat      180 ctagacactg taaagggccg attcaccatc tccagagaca atgccaagaa caccctgtac     240
ctgcaaatga gccgtctgaa gtctgaggac acagccatgt attactgtgc aagagggaag     300
tacgacgggg cctggtttgc ttactggggc caagggactc tggtcactgt ctctgca       357
```

<210> SEQ ID NO 33
<211> LENGTH: 119
<212> TYPE: PRT
<213> ORGANISM: Artificial Sequence
<220> FEATURE:
<223> OTHER INFORMATION: Heavy chain variable protein sequence of
      Hu3S193

<400> SEQUENCE: 33

| Glu | Val | Gln | Leu | Val | Glu | Ser | Gly | Gly | Gly | Val | Val | Gln | Pro | Gly | Arg |
| 1 | | | | 5 | | | | | 10 | | | | | 15 | |

| Ser | Leu | Arg | Leu | Ser | Cys | Ser | Thr | Ser | Gly | Phe | Thr | Phe | Ser | Asp | Tyr |
| | | | 20 | | | | | 25 | | | | | 30 | | |

| Tyr | Met | Tyr | Trp | Val | Arg | Gln | Ala | Pro | Gly | Lys | Gly | Leu | Glu | Trp | Val |
| | | 35 | | | | | 40 | | | | | 45 | | | |

| Ala | Tyr | Met | Ser | Asn | Val | Gly | Ala | Ile | Thr | Asp | Tyr | Pro | Asp | Thr | Val |
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Phe |
| 65 | | | | | 70 | | | | | 75 | | | | | 80 |

| Leu | Gln | Met | Asp | Ser | Leu | Arg | Pro | Glu | Asp | Thr | Gly | Val | Tyr | Phe | Cys |
| | | | | 85 | | | | | 90 | | | | | 95 | |

| Ala | Arg | Gly | Thr | Arg | Asp | Gly | Ser | Trp | Phe | Ala | Tyr | Trp | Gly | Gln | Gly |

```
                100              105              110
Thr Pro Val Thr Val Ser Ser
        115

<210> SEQ ID NO 34
<211> LENGTH: 117
<212> TYPE: PRT
<213> ORGANISM: Artificial Sequence
<220> FEATURE:
<223> OTHER INFORMATION: Heavy chain variable protein sequence of SC101

<400> SEQUENCE: 34

Gln Val Gln Leu Gln Gln Pro Gly Ala Glu Leu Val Lys Pro Gly Ala
1               5                   10                  15

Ser Val Ser Leu Ser Cys Lys Ala Ser Gly Tyr Thr Phe Thr Ser His
            20                  25                  30

Ser Met Tyr Trp Val Lys Gln Arg Pro Gly Gln Gly Leu Glu Trp Ile
        35                  40                  45

Gly Gly Ile Ile Pro Gly Asn Gly Asp Thr Asn Phe Asn Glu Lys Phe
    50                  55                  60

Lys Lys Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Ser Leu Ala Trp Leu His Tyr Phe Asp Tyr Trp Gly Gln Gly Thr Thr
            100                 105                 110

Leu Thr Val Ser Ser
        115

<210> SEQ ID NO 35
<211> LENGTH: 351
<212> TYPE: DNA
<213> ORGANISM: Artificial Sequence
<220> FEATURE:
<223> OTHER INFORMATION: Heavy chain variable DNA sequence of SC101

<400> SEQUENCE: 35
caggtccaac tgcagcagcc tgggggctgaa ctggtgaagc ctgggggcttc agtgagcttg      60 tcctgcaagg cttctggcta caccttcacc agccactcta tgtactgggt gaagcagagg     120
cctggacaag gccttgagtg gattgggggg attattcctg gcaatggtga tactaacttc     180
aatgaaaagt tcaagaaaaa ggccacactg actgtagaca atcctccag cacagcctac       240 atacaactca gcagcctgac atctgaggac tctgcggtct attattgttc attggcctgg     300
ctccactact ttgactactg gggccaaggc accactctca gtctccag c                351

<210> SEQ ID NO 36
<211> LENGTH: 113
<212> TYPE: PRT
<213> ORGANISM: Artificial Sequence
<220> FEATURE:
<223> OTHER INFORMATION: Light chain variable protein sequence of
      FG27.10

<400> SEQUENCE: 36

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ile Ile Val His Thr
            20                  25                  30

Asn Gly Asn Thr Tyr Leu Glu Trp Tyr Leu Gln Lys Pro Gly Gln Ser
```

-continued

```
          35              40              45
Pro Asn Leu Leu Ile Tyr Lys Val Ser Asn Arg Phe Ser Gly Val Pro
     50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Tyr Cys Phe Gln Gly
             85              90              95

Ser His Val Pro Phe Thr Phe Gly Ser Gly Thr Lys Leu Glu Ile Lys
             100             105             110

Arg
```

```
<210> SEQ ID NO 37
<211> LENGTH: 339
<212> TYPE: DNA
<213> ORGANISM: Artificial Sequence
<220> FEATURE:
<223> OTHER INFORMATION: Light chain variable DNA sequence of FG27.10

<400> SEQUENCE: 37
gatgttttga tgacccaaac tccactctcc ctgcctgtca gtcttggaga tcaagcctcc      60
atctcttgca gatctagtca gatcattgta catactaatg aaacaccta tttagaatgg     120 tacctgcaga aaccaggcca gtctccaaac ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcca     300
ttcacgttcg gctcggggac aaagttggaa ataaaacgg                             339
```

```
<210> SEQ ID NO 38
<211> LENGTH: 113
<212> TYPE: PRT
<213> ORGANISM: Artificial Sequence
<220> FEATURE:
<223> OTHER INFORMATION: Light chain variable protein sequence of BR96

<400> SEQUENCE: 38

Asp Val Leu Met Thr Gln Ile Pro Val Ser Leu Pro Val Ser Leu Gly
1               5               10              15

Asp Gln Ala Ser Ile Ser Cys Arg Ser Ser Gln Ile Ile Val His Asn
             20              25              30

Asn Gly Asn Thr Tyr Leu Glu Trp Tyr Leu Gln Lys Pro Gly Gln Ser
             35              40              45

Pro Gln Leu Leu Ile Tyr Lys Val Ser Asn Arg Phe Ser Gly Val Pro
     50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Val Tyr Tyr Cys Phe Gln Gly
             85              90              95

Ser His Val Pro Phe Thr Phe Gly Ser Gly Thr Lys Leu Glu Ile Lys
             100             105             110

Arg
```

```
<210> SEQ ID NO 39
<211> LENGTH: 339
<212> TYPE: DNA
<213> ORGANISM: Artificial Sequence
<220> FEATURE:
<223> OTHER INFORMATION: Light chain variable DNA sequence of BR96
```

```
<400> SEQUENCE: 39
gatgttttga tgacccaaat tccagtctcc ctgcctgtca gtcttggaga tcaagcgtcc      60
atctcttgca gatctagtca gatcattgta cataataatg gcaacaccta tttagaatgg     120
tacctgcaga aaccaggcca gtctccacag ctcctgatct acaaagtttc caaccgattt     180
tctggggtcc cagacaggtt cagcggcagt ggatcaggga cagatttcac actcaagatc     240
agcagagtgg aggctgagga tctgggagtt tattactgct ttcaaggttc acatgttcca     300
ttcacgttcg gctcggggac aaagttggaa ataaaacgg                            339

<210> SEQ ID NO 40
<211> LENGTH: 113
<212> TYPE: PRT
<213> ORGANISM: Artificial Sequence
<220> FEATURE:
<223> OTHER INFORMATION: Light chain variable protein sequence of sc101

<400> SEQUENCE: 40

Asp Val Leu Met Thr Gln Thr Pro Leu Ser Leu Pro Val Ser Leu Gly
1               5                   10                  15

Asp Gln Ala Ser Ile Ser Cys Arg Ser Gly Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 41
<211> LENGTH: 339
<212> TYPE: DNA
<213> ORGANISM: Artificial Sequence
<220> FEATURE:
<223> OTHER INFORMATION: Light chain variable DNA sequence of sc101

<400> SEQUENCE: 41
gatgttttga tgacccaaac tccactctcc ctgcctgtca gtcttggaga tcaagcctcc      60
atctcttgca gatctggtca gagcattgta catagtaatg aaacaccta tttagaatgg      120 tacctgcaga aaccaggcca gtctccaaag ctcctgatct acgaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttccg     300
tacacgttcg gaggggggac caagctggaa ataaaacgg                            339

<210> SEQ ID NO 42
<211> LENGTH: 113
<212> TYPE: PRT
<213> ORGANISM: Artificial Sequence
<220> FEATURE:
<223> OTHER INFORMATION: Light chain variable protein sequence of H18A

<400> SEQUENCE: 42
```

```
Asp Val Leu Met Thr Gln Thr Pro Leu Ser Leu Pro Val Ser Leu Gly
1               5                   10                  15

Asp Gln Ala Ser Ile Ser Cys Gly Ser Ser Gln Ser Ile Ile His Thr
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg

<210> SEQ ID NO 43
<211> LENGTH: 339
<212> TYPE: DNA
<213> ORGANISM: Artificial Sequence
<220> FEATURE:
<223> OTHER INFORMATION: Light chain DNA sequence of H18A

<400> SEQUENCE: 43
gatgttttga tgacccaaac tccactctcc ctgcctgtca gtcttggaga tcaagcctcc       60
atctcttgcg gatctagtca gagcattata catactaatg gaaacaccta tttagaatgg      120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ttcaaggttc acatgttcca      300
ttcacgttcg gctcggggac aaagttggaa ataaaacgt                             339

<210> SEQ ID NO 44
<211> LENGTH: 113
<212> TYPE: PRT
<213> ORGANISM: Artificial Sequence
<220> FEATURE:
<223> OTHER INFORMATION: Light chain variable protein sequence of
      Hu3S193

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Arg Ile Val His Ser
            20                  25                  30

Asn Gly Asn Thr Tyr Leu Glu Trp Tyr Gln Gln Thr Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Phe Thr Ile
65                  70                  75                  80

Ser Ser Leu Gln Pro Glu Asp Ile Ala Thr Tyr Tyr Cys Phe Gln Gly
                85                  90                  95

Ser His Val Pro Phe Thr Phe Gly Gln Gly Thr Lys Leu Gln Ile Thr
            100                 105                 110

Arg
```

```
<210> SEQ ID NO 45
<211> LENGTH: 119
<212> TYPE: PRT
<213> ORGANISM: Artificial Sequence
<220> FEATURE:
<223> OTHER INFORMATION: Heavy chain protein sequence of mFG27.18VH

<400> SEQUENCE: 45

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser His Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Gly Asp Asn Thr Tyr Tyr Pro Asp Thr Ile
    50                  55                  60

Arg Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ala
        115

<210> SEQ ID NO 46
<211> LENGTH: 26
<212> TYPE: PRT
<213> ORGANISM: Artificial Sequence
<220> FEATURE:
<223> OTHER INFORMATION: Heavy chain 4? Proximity Residues of FG27

<400> SEQUENCE: 46

Val Leu Thr Phe Thr Phe Ser Trp Val Arg Glu Trp Val Ala Arg Phe
1               5                   10                  15

Thr Ile Ser Arg Asn Leu Cys Ala Arg Trp
            20                  25

<210> SEQ ID NO 47
<211> LENGTH: 98
<212> TYPE: PRT
<213> ORGANISM: Artificial Sequence
<220> FEATURE:
<223> OTHER INFORMATION: Heavy chain protein sequence of AJ579110

<400> SEQUENCE: 47

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

```
<210> SEQ ID NO 48
<211> LENGTH: 119
<212> TYPE: PRT
<213> ORGANISM: Artificial Sequence
<220> FEATURE:
<223> OTHER INFORMATION: Heavy chain protein sequence of mFG27.18VH

<400> SEQUENCE: 48

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser His Tyr
            20                  25                  30

Tyr Met Tyr Trp Val Arg Gln Thr Pro Glu Lys Arg Leu Glu Trp Val
        35                  40                  45

Ala Tyr Ile Ser Asn Asp Gly Asp Asn Thr Tyr Tyr Pro Asp Thr Ile
    50                  55                  60

Arg Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ala
        115

<210> SEQ ID NO 49
<211> LENGTH: 119
<212> TYPE: PRT
<213> ORGANISM: Artificial Sequence
<220> FEATURE:
<223> OTHER INFORMATION: Heavy chain protein sequence of AJ579110

<400> SEQUENCE: 49

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Heavy chain protein sequence of FG27.18 RHA

<400> SEQUENCE: 50
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
            20                  25                  30

Tyr Met Tyr Trp Val Arg Gln Ala Pro Gly Lys Gly Leu Glu Trp Val
            35                  40                  45

Ala Tyr Ile Ser Asn Asp Gly Asp Asn Thr Tyr Tyr Pro Asp Thr Ile
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ser
            115
```

```
<210> SEQ ID NO 51
<211> LENGTH: 119
<212> TYPE: PRT
<213> ORGANISM: Artificial Sequence
<220> FEATURE:
<223> OTHER INFORMATION: Heavy chain protein sequence of FG27.18 RHB

<400> SEQUENCE: 51
```

```
Gln Val Gln Leu Val Glu Ser Gly Gly Gly Val Val Gln Pro Gly Arg
1               5                   10                  15

Ser Leu Arg Leu Ser Cys Ala Thr Ser Gly Phe Thr Phe Ser His Tyr
            20                  25                  30

Tyr Met Tyr Trp Val Arg Gln Ala Pro Gly Lys Gly Leu Glu Trp Val
            35                  40                  45

Ala Tyr Ile Ser Asn Asp Gly Asp Asn Thr Tyr Tyr Pro Asp Thr Ile
        50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ser
            115
```

```
<210> SEQ ID NO 52
<211> LENGTH: 112
<212> TYPE: PRT
<213> ORGANISM: Artificial Sequence
<220> FEATURE:
<223> OTHER INFORMATION: Light chain protein sequence of mFG27.18VK

<400> SEQUENCE: 52
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ile Ile Val His Thr
            20                  25                  30

Asn Gly Asn Thr Tyr Leu Glu Trp Tyr Leu Gln Lys Pro Gly Gln Ser
            35                  40                  45

Pro Asn Leu Leu Ile Tyr Lys Val Ser Asn Arg Phe Ser Gly Val Pro
        50                  55                  60
```

```
Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110
```

<210> SEQ ID NO 53
<211> LENGTH: 28
<212> TYPE: PRT
<213> ORGANISM: Artificial Sequence
<220> FEATURE:
<223> OTHER INFORMATION: Light chain 4? Proximity Residues of FG27

<400> SEQUENCE: 53

```
Asp Val Leu Met Thr Cys Trp Tyr Leu Leu Ile Tyr Gly Val Pro Asp
1               5                   10                  15

Phe Ser Gly Ser Gly Gly Thr Asp Phe Tyr Cys Phe
            20                  25
```

<210> SEQ ID NO 54
<211> LENGTH: 101
<212> TYPE: PRT
<213> ORGANISM: Artificial Sequence
<220> FEATURE:
<223> OTHER INFORMATION: Light chain protein sequence of X63397

<400> SEQUENCE: 54

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Ala
                85                  90                  95

Leu Gln Thr Pro Pro
            100
```

<210> SEQ ID NO 55
<211> LENGTH: 112
<212> TYPE: PRT
<213> ORGANISM: Artificial Sequence
<220> FEATURE:
<223> OTHER INFORMATION: Light chain protein sequence of mFG27.18 VK

<400> SEQUENCE: 55

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ile Ile Val His Thr
            20                  25                  30

Asn Gly Asn Thr Tyr Leu Glu Trp Tyr Leu Gln Lys Pro Gly Gln Ser
            35                  40                  45

Pro Asn Leu Leu Ile Tyr Lys Val Ser Asn Arg Phe Ser Gly Val Pro
        50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110

<210> SEQ ID NO 56
<211> LENGTH: 100
<212> TYPE: PRT
<213> ORGANISM: Artificial Sequence
<220> FEATURE:
<223> OTHER INFORMATION: Light chain protein sequence of Z46620

<400> SEQUENCE: 56

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro
            100

<210> SEQ ID NO 57
<211> LENGTH: 112
<212> TYPE: PRT
<213> ORGANISM: Artificial Sequence
<220> FEATURE:
<223> OTHER INFORMATION: Light chain protein sequence of FG27.18 RKA

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ile Ile Val His Thr
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
                100                 105                 110

<210> SEQ ID NO 58
<211> LENGTH: 112
<212> TYPE: PRT
<213> ORGANISM: Artificial Sequence
<220> FEATURE:
<223> OTHER INFORMATION: Light chain protein sequence of FG27.18 RKB
```

<400> SEQUENCE: 58

Asp Val Leu Met Thr Gln Ser Pro Leu Ser Leu Pro Val Thr Pro Gly
1               5                   10                  15

Glu Pro Ala Ser Ile Ser Cys Arg Ser Ser Gln Ile Ile Val His Thr
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 59
<211> LENGTH: 112
<212> TYPE: PRT
<213> ORGANISM: Artificial Sequence
<220> FEATURE:
<223> OTHER INFORMATION: Light chain protein sequence of FG27.18 RKC

<400> SEQUENCE: 59

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ile Ile Val His Thr
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 60
<211> LENGTH: 112
<212> TYPE: PRT
<213> ORGANISM: Artificial Sequence
<220> FEATURE:
<223> OTHER INFORMATION: Light chain protein sequence of FG27.18 RKD

<400> SEQUENCE: 60

Asp Ile Leu Met Thr Gln Ser Pro Leu Ser Leu Pro Val Thr Pro Gly
1               5                   10                  15

Glu Pro Ala Ser Ile Ser Cys Arg Ser Ser Gln Ile Ile Val His Thr
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

```
Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 61
<211> LENGTH: 19
<212> TYPE: DNA
<213> ORGANISM: Artificial Sequence
<220> FEATURE:
<223> OTHER INFORMATION: PCR primer 1

<400> SEQUENCE: 61
ttagcacccc tggccaagg                                                 19

<210> SEQ ID NO 62
<211> LENGTH: 21
<212> TYPE: DNA
<213> ORGANISM: Artificial Sequence
<220> FEATURE:
<223> OTHER INFORMATION: PCR primer 2

<400> SEQUENCE: 62
cttactccct tggaggccat g                                              21

<210> SEQ ID NO 63
<211> LENGTH: 8
<212> TYPE: PRT
<213> ORGANISM: Artificial Sequence
<220> FEATURE:
<223> OTHER INFORMATION: CDRH1

<400> SEQUENCE: 63

Gly Phe Thr Phe Ser His Tyr Tyr
1               5

<210> SEQ ID NO 64
<211> LENGTH: 8
<212> TYPE: PRT
<213> ORGANISM: Artificial Sequence
<220> FEATURE:
<223> OTHER INFORMATION: CDRH2

<400> SEQUENCE: 64

Ile Ser Asn Asp Gly Asp Asn Thr
1               5

<210> SEQ ID NO 65
<211> LENGTH: 12
<212> TYPE: PRT
<213> ORGANISM: Artificial Sequence
<220> FEATURE:
<223> OTHER INFORMATION: CDRH3

<400> SEQUENCE: 65

Ala Arg Gly Lys Tyr Asp Gly Ala Trp Phe Ala Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: CDRL1

<400> SEQUENCE: 66
```

```
Gln Ile Ile Val His Thr Asn Gly Asn Thr Tyr
1               5                   10
```

<210> SEQ ID NO 67
<211> LENGTH: 3
<212> TYPE: PRT
<213> ORGANISM: Artificial Sequence
<220> FEATURE:
<223> OTHER INFORMATION: CDRL2

<400> SEQUENCE: 67

```
Lys Val Ser
1
```

<210> SEQ ID NO 68
<211> LENGTH: 9
<212> TYPE: PRT
<213> ORGANISM: Artificial Sequence
<220> FEATURE:
<223> OTHER INFORMATION: CDRL3

<400> SEQUENCE: 68

```
Phe Gln Gly Ser His Val Pro Phe Thr
1               5
```

<210> SEQ ID NO 69
<211> LENGTH: 119
<212> TYPE: PRT
<213> ORGANISM: Homo sapiens

<400> SEQUENCE: 69

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His His Asp Ser Ser Gly Leu Pro Tyr Trp Gly Gln Gly
            100                 105                 110

Thr Leu Val Thr Val Ser Ser
        115
```

<210> SEQ ID NO 70
<211> LENGTH: 119
<212> TYPE: PRT
<213> ORGANISM: Homo sapiens

<400> SEQUENCE: 70

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
```

```
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Ser Ser Ser Phe Asp Tyr Trp Gly Gln Gly
                100                 105                 110

Thr Leu Val Thr Val Ser Ser
        115

<210> SEQ ID NO 71
<211> LENGTH: 119
<212> TYPE: PRT
<213> ORGANISM: Homo sapiens

<400> SEQUENCE: 71

Leu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
        35                  40                  45

Ala Val Ile Trp Tyr Asp Gly Ser Asn Glu Asn Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Gly Ser Ser Ser Trp Tyr Ala Tyr Trp Gly Gln Gly
                100                 105                 110

Thr Leu Val Thr Val Ser Ser
        115

<210> SEQ ID NO 72
<211> LENGTH: 119
<212> TYPE: PRT
<213> ORGANISM: Homo sapiens

<400> SEQUENCE: 72

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Pro Glu Val Asp Phe Asp Tyr Trp Gly Gln Gly
                100                 105                 110

Thr Leu Val Thr Val Ser Ser
        115
```

<210> SEQ ID NO 73
<211> LENGTH: 119
<212> TYPE: PRT
<213> ORGANISM: Homo sapiens

<400> SEQUENCE: 73

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Trp Phe Ser Asp Ala Phe Asp Ile Trp Gly Gln Gly
                100                 105                 110

Thr Met Val Thr Val Ser Ser
        115

<210> SEQ ID NO 74
<211> LENGTH: 120
<212> TYPE: PRT
<213> ORGANISM: Homo sapiens

<400> SEQUENCE: 74

Cys Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser Ser
            20                  25                  30

Tyr Trp Met Ser Trp Val Arg Gln Leu Pro Gly Lys Gly Leu Glu Trp
        35                  40                  45

Val Ala Asn Ile Lys Gln Asp Gly Ser Glu Lys Tyr Tyr Val Asp Ser
        50                  55                  60

Val Lys Gly Arg Phe Thr Ile Ser Arg Asp Asn Ala Lys Asn Ser Leu
65                  70                  75                  80

Tyr Leu Gln Met Asn Ser Leu Arg Ala Glu Asp Thr Ala Val Tyr Tyr
                85                  90                  95

Cys Ala Arg Lys Arg Ala Gly Lys Ala Ala Phe Asn Ile Trp Gly Gln
                100                 105                 110

Gly Thr Met Val Thr Val Ser Ser
        115                 120

<210> SEQ ID NO 75
<211> LENGTH: 26
<212> TYPE: PRT
<213> ORGANISM: Homo sapiens

<400> SEQUENCE: 75

Val Leu Ala Phe Thr Phe Ser Trp Val Arg Glu Trp Val Ala Arg Phe
1               5                   10                  15

Thr Ile Ser Arg Asn Leu Cys Ala Arg Trp
            20                  25

<210> SEQ ID NO 76

<211> LENGTH: 113
<212> TYPE: PRT
<213> ORGANISM: Homo sapiens

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Leu Met Cys Ser Phe Gly Gln Gly Thr Lys Leu Glu Ile
            100                 105                 110

Lys

<210> SEQ ID NO 77
<211> LENGTH: 108
<212> TYPE: PRT
<213> ORGANISM: Homo sapiens

<400> SEQUENCE: 77

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ile Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys
            100                 105

<210> SEQ ID NO 78
<211> LENGTH: 113
<212> TYPE: PRT
<213> ORGANISM: Homo sapiens

<400> SEQUENCE: 78

Ala Asp Val Val Met Thr Gln Ser Pro Leu Ser Leu Pro Val Thr Pro
1               5                   10                  15

Gly Glu Pro Ala Ser Ile Ser Cys Arg Ser Ser Gln Ser Leu Leu His
            20                  25                  30

Ser Asn Gly Tyr Asn Tyr Leu Asp Trp Tyr Leu Gln Lys Pro Gly Gln
        35                  40                  45

Ser Pro Gln Leu Leu Ile Tyr Leu Gly Ser Asn Arg Ala Ser Gly Val
    50                  55                  60

Pro Asp Arg Phe Ser Gly Ser Gly Ser Gly Thr Asp Phe Thr Leu Lys

```
65                    70                    75                    80

Ile Ser Arg Val Glu Ala Glu Asp Val Gly Val Tyr Tyr Cys Met Gln
                 85                    90                    95

Ala Leu Gln Thr Pro Tyr Thr Phe Gly Gln Gly Thr Lys Leu Glu Ile
                 100                   105                   110

Lys
```

<210> SEQ ID NO 79
<211> LENGTH: 113
<212> TYPE: PRT
<213> ORGANISM: Homo sapiens

<400> SEQUENCE: 79

```
Ser Asp Val Val Met Thr Gln Ser Pro Leu Ser Leu Pro Val Thr Pro
1                5                    10                   15

Gly Glu Pro Ala Ser Ile Ser Cys Arg Ser Ser Gln Ser Ile Val His
                 20                   25                   30

Ser Asn Gly Asn Thr Tyr Leu Gln Trp Tyr Leu Gln Lys Pro Gly Gln
            35                   40                   45

Ser Pro Gln Leu Leu Ile Tyr Lys Val Ser Asn Arg Leu Tyr Gly Val
        50                   55                   60

Pro Asp Arg Phe Ser Gly Ser Gly Ser Gly Thr Asp Phe Thr Leu Lys
65                   70                   75                   80

Ile Ser Arg Val Glu Ala Glu Asp Val Gly Val Tyr Tyr Cys Phe Gln
                 85                    90                    95

Gly Ser His Val Pro Trp Thr Phe Gly Gln Gly Thr Lys Val Glu Ile
                 100                   105                   110

Lys
```

<210> SEQ ID NO 80
<211> LENGTH: 112
<212> TYPE: PRT
<213> ORGANISM: Homo sapiens

<400> SEQUENCE: 80

```
Asp Val Val Met Thr Gln Ser Pro Leu Ser Leu Pro Val Thr Pro Gly
1                5                    10                   15

Glu Pro Ala Ser Ile Ser Cys Arg Ser Ser Gln Ser Leu Leu His Ser
                 20                   25                   30

Asn Gly Tyr Asn Tyr Leu Asp Trp Tyr Leu Gln Lys Pro Gly Gln Ser
            35                   40                   45

Pro Gln Leu Leu Ile Tyr Leu Gly Ser Asn Arg Ala Ser Gly Val Pro
        50                   55                   60

Asp Arg Phe Ser Gly Ser Gly Ser Gly Thr Asp Phe Thr Leu Lys Ile
65                   70                   75                   80

Ser Arg Val Glu Ala Glu Asp Val Gly Val Tyr Tyr Cys Met Gln Ala
                 85                    90                    95

Leu Gln Thr Pro Leu Thr Phe Gly Gly Gly Thr Lys Val Glu Ile Lys
                 100                   105                   110
```

<210> SEQ ID NO 81
<211> LENGTH: 112
<212> TYPE: PRT
<213> ORGANISM: Homo sapiens

<400> SEQUENCE: 81

```
Asp Val Val Met Thr Gln Ser Pro Leu Ser Leu Ala Val Thr Pro Gly
```

-continued

```
1               5                    10                   15

Glu Pro Ala Ser Ile Ser Cys Arg Ser Ser Gln Ser Val Val Phe Thr
                20                   25                   30

Asn Gly Lys Asn Tyr Leu Asp Trp Tyr Leu Gln Lys Pro Gly Gln Ser
            35                   40                   45

Pro Gln Leu Leu Ile Tyr Leu Gly Ser Asn Arg Ala Ser Gly Val Pro
    50                   55                   60

Asp Arg Phe Ser Gly Ser Gly Ser Gly Thr Asp Phe Thr Leu Lys Ile
65                   70                   75                   80

Ser Arg Val Glu Ala Asp Asp Val Gly Val Tyr Tyr Cys Met His Ala
                85                   90                   95

Val Gln Ala Pro Trp Thr Phe Gly Gln Gly Thr Lys Val Glu Ile Lys
                100                  105                  110
```

```
<210> SEQ ID NO 82
<211> LENGTH: 111
<212> TYPE: PRT
<213> ORGANISM: Homo sapiens

<400> SEQUENCE: 82

Asp Val Leu Met Thr Gln Thr Pro Asp Ser Leu Pro Val Ser Leu Gly
1               5                    10                   15

Asp Arg Ala Ser Ile Ser Cys Arg Ser Ser Gln Ile Ile Val His Ser
                20                   25                   30

Asp Gly Asn Thr Tyr Leu Glu Trp Phe Leu Gln Lys Pro Gly Gln Ser
            35                   40                   45

Pro Lys Leu Leu Ile Tyr Lys Val Ser Asn Arg Phe Ser Gly Val Pro
    50                   55                   60

Asp Arg Phe Ser Gly Ser Gly Ser Gly Thr Asp Phe Thr Leu Met Ile
65                   70                   75                   80

Ser Arg Val Glu Ala Glu Asp Leu Gly Val Tyr Tyr Cys Phe Gln Gly
                85                   90                   95

Ser His Val Pro His Thr Phe Gly Gly Gly Thr Lys Leu Glu Ile
                100                  105                  110
```

```
<210> SEQ ID NO 83
<211> LENGTH: 112
<212> TYPE: PRT
<213> ORGANISM: Homo sapiens

<400> SEQUENCE: 83

Ala Asp Ile Val Met Thr Gln Thr Pro Leu Ser Leu Ser Val Thr Pro
1               5                    10                   15

Gly Gln Pro Ala Ser Ile Ser Cys Lys Ser Ser Gln Ser Leu Leu His
                20                   25                   30

Asp Asp Gly Lys Thr Tyr Leu Tyr Trp Tyr Leu Gln Lys Pro Gly Gln
            35                   40                   45

Ser Pro Gln Leu Leu Ile Tyr Glu Val Ser Asn Arg Phe Ser Gly Val
    50                   55                   60

Pro Asp Arg Phe Ser Gly Ser Gly Ser Gly Thr Asp Phe Thr Leu Lys
65                   70                   75                   80

Ile Ser Arg Val Glu Ala Glu Asp Val Gly Val Tyr Tyr Cys Met Arg
                85                   90                   95

Ser Ile Gln Phe Ala Thr Phe Gly Gln Gly Thr Lys Leu Glu Ile Lys
                100                  105                  110
```

-continued

```
<210> SEQ ID NO 84
<211> LENGTH: 28
<212> TYPE: PRT
<213> ORGANISM: Homo sapiens

<400> SEQUENCE: 84

Asp Ile Val Met Thr Cys Trp Tyr Leu Leu Ile Tyr Gly Val Pro Asp
1               5                   10                  15

Phe Ser Gly Ser Gly Gly Thr Asp Phe Tyr Cys Phe
            20                  25

<210> SEQ ID NO 85
<211> LENGTH: 28
<212> TYPE: PRT
<213> ORGANISM: Homo sapiens

<400> SEQUENCE: 85

Asp Val Val Met Thr Cys Trp Tyr Leu Leu Ile Tyr Gly Val Pro Asp
1               5                   10                  15

Phe Ser Gly Ser Gly Gly Thr Asp Phe Tyr Cys Phe
            20                  25

<210> SEQ ID NO 86
<211> LENGTH: 28
<212> TYPE: PRT
<213> ORGANISM: Homo sapiens

<400> SEQUENCE: 86

Asp Val Leu Met Thr Cys Trp Phe Leu Leu Ile Tyr Gly Val Pro Asp
1               5                   10                  15

Phe Ser Gly Ser Gly Gly Thr Asp Phe Tyr Cys Phe
            20                  25

<210> SEQ ID NO 87
<211> LENGTH: 449
<212> TYPE: PRT
<213> ORGANISM: Artificial sequence
<220> FEATURE:
<223> OTHER INFORMATION: Amino acid sequence of Ch27.10 heavy chain
      variable region (excluding leader sequence)

<400> SEQUENCE: 87

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser His Tyr
            20                  25                  30

Tyr Met Tyr Trp Val Arg Gln Thr Pro Glu Lys Arg Leu Glu Trp Val
            35                  40                  45

Ala Tyr Ile Ser Asn Asp Gly Asp Asn Thr Tyr Tyr Pro Asp Thr Ile
    50                  55                  60

Arg Gly Arg Phe Thr Ile Ser Arg Asp Asn Ala Arg Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Lys Tyr Asp Gly Ala Trp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys
```

```
<210> SEQ ID NO 88
<211> LENGTH: 219
<212> TYPE: PRT
<213> ORGANISM: Artificial sequence
<220> FEATURE:
<223> OTHER INFORMATION: Amino acid sequence of Ch27.10 light chain
      variable region (excluding leader sequence)

<400> SEQUENCE: 88
```

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ile Ile Val His Thr
                20                  25                  30

Asn Gly Asn Thr Tyr Leu Glu Trp Tyr Leu Gln Lys Pro Gly Gln Ser
        35                  40                  45
```

-continued

```
Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215
```

```
<210> SEQ ID NO 89
<211> LENGTH: 449
<212> TYPE: PRT
<213> ORGANISM: Artificial sequence
<220> FEATURE:
<223> OTHER INFORMATION: Amino acid sequence of the humanised FG27 heavy
      chain variable region

<400> SEQUENCE: 89
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser His Tyr
                20                  25                  30

Tyr Met Tyr Trp Val Arg Gln Ala Pro Gly Lys Gly Leu Glu Trp Val
                35                  40                  45

Ala Tyr Ile Ser Asn Asp Gly Asp Asn Thr Tyr Tyr Pro Asp Thr Ile
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Tyr Asp Gly Ala Trp Phe Ala Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys
```

```
<210> SEQ ID NO 90
<211> LENGTH: 239
<212> TYPE: PRT
<213> ORGANISM: Artificial sequence
<220> FEATURE:
<223> OTHER INFORMATION: Amino acid sequence of humanised FG27 kappa
      chain variable region

<400> SEQUENCE: 90
```

```
Met Glu Ala Pro Ala Gln Leu Leu Phe Leu Leu Leu Leu Trp Leu Pro
1               5                   10                  15

Asp Thr Thr Gly Asp Val Val Met Thr Gln Ser Pro Leu Ser Leu Pro
                20                  25                  30

Val Thr Pro Gly Glu Pro Ala Ser Ile Ser Cys Arg Ser Ser Gln Ile
        35                  40                  45

Ile Val His Thr Asn Gly Asn Thr Tyr Leu Glu Trp Tyr Leu Gln Lys
    50                  55                  60

Pro Gly Gln Ser Pro Gln Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95
```

-continued

```
Thr Leu Lys Ile Ser Arg Val Glu Ala Glu Asp Val Gly Val Tyr Tyr
            100             105             110

Cys Phe Gln Gly Ser His Val Pro Phe Thr Phe Gly Gln Gly Thr Lys
        115             120             125

Leu Glu Ile Lys Arg Thr Val Ala Ala Pro Ser Val Phe Ile Phe Pro
    130             135             140

Pro Ser Asp Glu Gln Leu Lys Ser Gly Thr Ala Ser Val Val Cys Leu
145             150             155             160

Leu Asn Asn Phe Tyr Pro Arg Glu Ala Lys Val Gln Trp Lys Val Asp
            165             170             175

Asn Ala Leu Gln Ser Gly Asn Ser Gln Glu Ser Val Thr Glu Gln Asp
        180             185             190

Ser Lys Asp Ser Thr Tyr Ser Leu Ser Ser Thr Leu Thr Leu Ser Lys
        195             200             205

Ala Asp Tyr Glu Lys His Lys Val Tyr Ala Cys Glu Val Thr His Gln
    210             215             220

Gly Leu Ser Ser Pro Val Thr Lys Ser Phe Asn Arg Gly Glu Cys
225             230             235
```

BINDING MEMBERS

The present invention relates to specific binding members, such as antibodies and fragments thereof, that are capable of specifically binding a Lewis Y (Le$^y$) carbohydrate. It also relates to the use of such binding members in medicine and to nucleic acids encoding such binding members.

Glycan structures are present on both protein and glycolipid backbones and can be massively over-expressed in cancer due to altered expression of glycosyltransferases. Glycolipids consist of a lipid tail with a carbohydrate head and constitute about 5% of lipid molecules in the outer monolayer. There are three main series of glycolipids, globo, neolacto and ganglio lipids. Glycolipids are postulated to be very good targets due to their high surface density, mobility, and association with membrane microdomains; all of which contribute to strong cellular interactions. However, generating anti-glycolipid antibodies is a challenging task as there is no T cell help and the monoclonal antibodies (mAbs) are usually of low affinity and of the IgM subclass (Durrant, Noble et al. 2012, Rabu, McIntosh et al. 2012). Although mAbs to glycans expressed on proteins overcome this problem, they present new challenges as the mAbs rarely see just the small glycan but usually recognise the glycan on the specific protein, giving a very restrictive expression.

Only a limited number of antibodies recognising glycans have been described. Several anti-Lewis (Le) carbohydrate antigen mAbs have been generated to date but they often have cross reactivity with a range of glycans expressed on normal tissues. Lewis carbohydrate antigens are formed by the sequential addition of fucose onto oligosaccharide precursor chains on glycoproteins or glycolipids through the action of a set of glycosyltransferases (Yuriev, Farrugia et al. 2005). They can be divided into 2 groups, type I (Le$^a$ and Le$^b$) and type II (Le$^x$ and Le$^y$). Le$^a$ and Le$^b$ antigens are regarded as blood group antigens whereas Le$^x$ and Le$^y$ are reported to be expressed only in certain epithelial cells (Scott, Geleick et al. 2000), viewed as tumour associated markers (Soejima and Koda 2005) and represent attractive targets for cancer treatment, including antibody based immunotherapy (Scott, Geleick et al. 2000). Most normal tissues do not express Lewis Y, with the exception of epithelial cells in the gastrointestinal tract, but at very low densities (Schuster, Umana et al. 2005). However, Lewis Y (Fuca1-2Galb1-4(Fuca1-3)GlcNAc) is reported to be expressed at high densities on nearly 70% of human epithelial carcinomas and thus is an attractive candidate target for cancer immunotherapy. The recognition of Lewis Y as a good therapeutic target has led to the production of a number of anti-Le$^y$ antibodies. Some of these anti-Le$^y$ mAbs cross-react with other Lewis antigens, for example the mAb 692/29 which recognises Le$^{b/y}$, have demonstrated anti-tumour responses against colonic tumours in xenograft models (Noble, Spendlove et al. 2013).

Several other mAbs that bind Le$^y$ are known in the art, but they cross react with other related Lewis antigens. For example, EP-B-0285059 discloses an antibody, BR-55, which reacts with both Lewis$^y$ and B-7-2. B-7-2 has also been shown to be associated with tumour cells (EP-B-0285059). U.S. Pat. No. 5,869,045 discloses an antibody, BR-96, which binds to both Lewis$^y$ and Lewis$^x$ haptens. Antibodies which bind to both Lewis$^y$ and Lewis$^b$ antigens are known. Studies have demonstrated that C14 monoclonal antibody recognises and binds to both Lewis$^y$ and Lewis$^b$ (extended and non-extended forms) antigens (Durrant at al., Hybridoma, 12, 647-660 (1996)). WO02/092126 discloses mAbs that bind to both Lewis$^y$ and Lewis$^b$ haptens.

A number of clinical trials utilising murine or chimeric anti-Le$^y$ antibodies have been conducted (Scott, Geleick et al. 2000). Unfortunately, often, anti-Le$^y$ mAbs cross-react with Lewis X and H type II structures that are more commonly expressed on normal tissues (Furukawa, Welt et al. 1990, Yin, Finstad et al. 1996). A range of Le$^y$ antibodies has also been identified but a consistent problem with these antibodies has been the degree of cross reactivity with Le$^x$, and H type 2 structures causing red blood cell agglutination and gastrointestinal toxicity (Kitamura, Stockert et al. 1994, Pai, Wittes et al. 1996, Tolcher, Sugarman et al. 1999). Thus, fine specificity of the anti-Le$^y$ antibodies is important for successful clinical treatment.

In a first aspect, the present invention provides an isolated specific binding member capable of binding specifically to Fuca1-2Galb1-4(Fuca1-3)GlcNAc (Le$^y$).

The inventors have provided specific binding members which demonstrate potent in vivo anti-tumour activity. The specific binding members of the invention display potent immune-mediated cytotoxic activity against human colon cancer cells in vitro via antibody-dependent cell-mediated cytotoxicity (ADCC) and complement dependent cytotoxicity (CDC). They also have the ability to directly induce cell death without the need for immune effector cells. By immunising with tumour glycolipid rather than glycoproteins or whole cells, the inventors have produced ultra-specific anti-Le$^y$ mAbs, which do not cross react with any other glycan. Examples of these mAbs are an IgG3k murine mAb known herein as "FG27.10" and an IgG1k murine mAb known herein as "FG27.18", a hIgG1 chimeric (known as "CH27") and hIgG1 humanised (known as "Hu27").

Figure 13A:
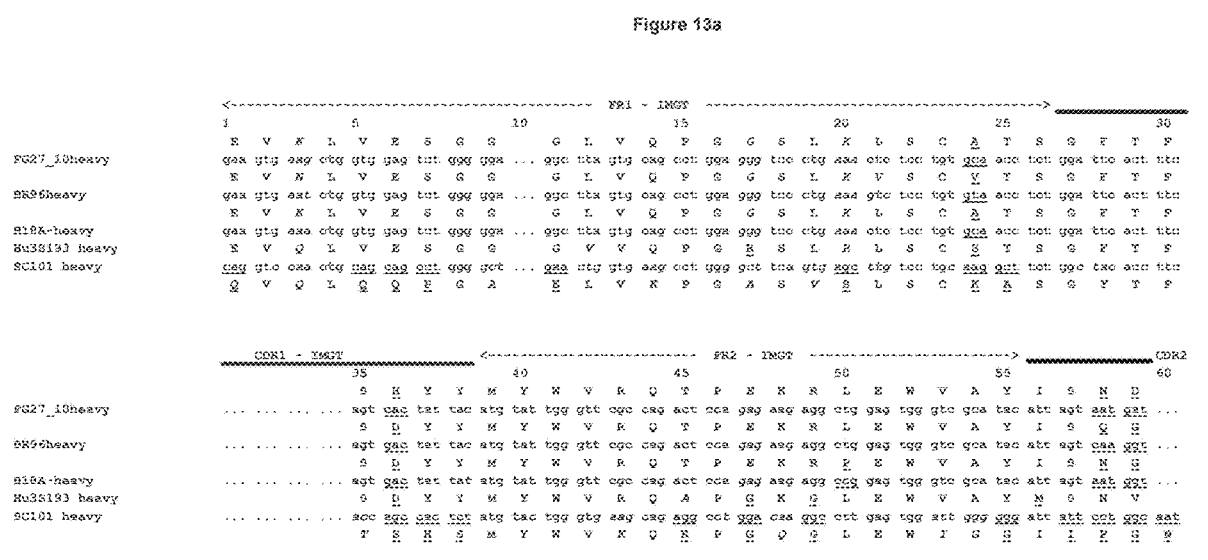

In contrast to previous studies with anti-Le$^y$ mAbs that cross react with other glycans, the specific binding members of the present invention have a very restrictive normal distribution and only bound to subpopulations of cells within normal stomach, lung, tonsil, pancreas and duodenum. Further, they failed to stain colon, jejunum, breast, kidney or the ileum. They bind strongly to a wide range of tumours including 80% of gastric, 100% of colorectal, 95% of ovarian and 85% of breast tumours. Specific binding members of the invention, such as FG27.10/18, have monospecificity for just Le$^y$. The inventors have shown that specific binding members in accordance with failed to bind to the cell line Colo21. By contrast, a Le$^{y/x}$ mAb bound strongly and a Le$^{y/b}$ mAb bound moderately. This shows that Colo201 expresses Le$^x$ and Le$^b$, but not Le$^y$ and confirms the specificity of the specific binding members of the present invention. This specificity is reflected in the similar but distinct sequence of the FG27 variable heavy and light chain regions (FIG. 13a,b). FG27 shows 16-68% differences in the amino acid sequences CDRs within the heavy chain, 4.3-16% differences in amino acid differences in the CDR sequence in the light chain, 8.6-49.5% differences in amino acid sequence in the variable region of the heavy chain, 2-24% differences in amino acid sequence in the variable region of the light chain from the other cross reactive Le$^y$ mabs (see Table 4 herein). The most variation is within CDRH2 with 3-5 of the 8 amino acids varying between the different mAbs.

Specific binding members of the present invention may be attached to a lipid or protein backbone. The protein backbone may have a molecular weight of about 50-150 kDa, as determined by SDS-PAGE.

The specific binding member of the present invention preferably comprise one or more binding domains selected from the binding domains having the amino acid sequence substantially as set out as residues 27 to 38 (CDRH1), 54 to 65 (CDRH2) or 105 to 116 (CDRH3) of FIG. 1*a* or 1*b*. The specific binding member may comprise a binding domain which comprises an amino acid sequence substantially as set out as residues 105 to 116 (CDRH3) of the amino acid sequence of FIG. 1*a* or 1*b*. Such a specific binding member may additionally comprise one or both, preferably both, of the binding domains having an amino acid sequence substantially as set out as residues 27 to 38 (CDRH1) and residues 56 to 65 (CDRH2) of the amino acid sequence shown in FIGS. 1*a* and 1*b*.

The binding member may comprise an amino acid sequence substantially as set out as 1-127 (VH) of FIG. 1*a* or 1*b*.

The specific binding member may comprise one or more binding domains selected from binding domains having the amino acid sequence of residues 27 to 38 (CDRL1), 56 to 65 (CDRL2) or 105 to 113 (CDRL3) of FIG. 1*c*. The binding member may comprise a binding domain having an amino acid sequence substantially as set out as residues 105 to 113 (CDRL3) of the amino acid sequence of FIG. 1*c*. Such a specific binding member may additionally comprise one or both, preferably both, of the binding domains having an amino acid sequence substantially as set out as residues 27 to 38 (CDRL1) and residues 56 to 65 (CDRL2) of the amino acid sequence shown in FIG. 1*c*.

Specific binding members which comprise a plurality of binding domains of the same or different sequence, or combinations thereof, are included within the present invention. The or each binding domain may be carried by a human antibody framework. For example, one or more binding domains may be substituted for the complementary determining regions (CDRs) of a whole human antibody or of the variable region thereof.

One isolated specific binding member of the invention comprises the amino acid sequence substantially as set out as residues 1 to 124 (VL) of the amino acid sequence shown in FIG. 1*c*.

The isolated specific binding member of the invention may comprise one or more, preferably all, of the binding domains having an amino acid sequence substantially as set out as residues 27 to 38 (CDRH1), 54 to 65 (CDRH2) or 105 to 116 (CDRH3) of FIG. 1*a* or 1*b* in combination with one or more, preferably all, of the binding domains having an amino acid sequence substantially as set out as residues 27 to 38 (CDRL1), 56 to 65 (CDRL2) or 105 to 113 (CDRL3) of FIG. 1*c*.

The binding member may comprise an amino acid sequence substantially as set out as residues 1 to 127 (VH) of the amino acid sequence of FIG. 1*a* or 1*b*, and an amino acid sequence substantially as set out as residues 1 to 124 (VL) of the amino acid sequence of FIG. 1*c*.

Once a single, archetypal mAb, for example an FG27 mAb, has been isolated that has the desired properties described herein, it is straightforward to generate other mAbs with similar properties, by using art-known methods. For example, the method of Jespers et al., 1994 (Jespers, Roberts et al. 1994), may be used to guide the selection of mAbs having the same epitope and therefore similar properties to the archetypal mAb. Using phage display, first the heavy chain of the archetypal antibody is paired with a repertoire of (preferably human) light chains to select a glycan-binding mAb, and then the new light chain is paired with a repertoire of (preferably human) heavy chains to select a (preferably human) glycan-binding mAb having the same epitope as the archetypal mAb.

The specific binding member may be an antibody or an antibody fragment, Fab, (Fab')2, scFv, Fv, dAb, Fd or a diabody. The antibody may be a polyclonal antibody. The antibody may be a monoclonal antibody (mAb). Antibodies of the invention may be humanised, chimeric or veneered antibodies, or may be non-human antibodies of any species.

Murine or chimeric antibodies carry an increased risk of adverse anti-murine antibody (HAMA) reactions in patients (Schroff et al. 1985; Azinovic et al. 2006; Miotti et al. 1999; D'Arcy and Mannik 2001). Accordingly, most approved therapeutic mAbs are either humanised or fully human IgG antibodies The specific binding member of the invention may comprise a heavy chain having an amino acid sequence substantially as set out in FIG. 2*a* and a light chain having an amino acid sequence substantially as set out in FIG. 2*b*.

The specific binding member of the invention may comprise a heavy chain having an amino acid sequence substantially as set out in FIG. 3*a* and a light chain having an amino acid sequence substantially as set out in FIG. 3*b*.

The specific binding member of the invention may comprise a heavy chain having an amino acid sequence substantially as set out in FIG. 33 and/or a light chain having an amino acid sequence substantially as set out in FIG. 33.

The invention further provides a binding member which competes for binding to Le$^y$ containing glycans with an antibody comprising a VH chain having the amino acid sequence of residues 1 to 127 of FIG. 1*a* or 1*b* and a VL chain having the amino acid sequence of residues 1 to 124 of FIG. 1*c*.

Specific binding members that are capable of binding specifically to Le$^y$ and are at least 90%, at least 95% or at least 99% identical in the VH and/or VL domain to the VH or VL domains of FIG. 1, 2 or 3 are included in the invention. Specific binding members that are capable of binding specifically to Le$^y$ and are at least 90%, at least 95% or at least 99% identical to the heavy chain and/or light chain of FIG. 33 are included in the invention. Preferably such antibodies differ from the sequences of FIG. 1, 2 or 3 by a small number of functionally inconsequential amino acid substitutions (e.g., conservative substitutions), deletions, or insertions.

Specific binding members of the invention may carry a detectable or functional label.

In further aspects, the invention provides an isolated nucleic acid encoding a specific binding member of the invention, and methods of preparing specific binding members of the invention which comprise expressing said nucleic acids under conditions to bring about expression of said binding member, and recovering the binding member. Isolated nucleic acids encoding specific binding members that are capable of binding specifically to Le$^y$ and are at least 90%, at least 95% or at least 99% identical to the sequences provided herein are included in the invention.

Specific binding members of the invention may be used in a method of treatment or diagnosis of the human or animal body, such as a method of treatment of a tumour in a patient (preferably human) which comprises administering to said patient an effective amount of a specific binding member of the invention. The invention also provides a specific binding member of the present invention for use in medicine, preferably for use in treating a tumour, as well as the use of a specific binding member of the present invention in the manufacture of a medicament for the diagnosis or treatment of a tumour. The tumour may be a gastric, colorectal, pancreatic, lung, ovarian or breast tumour.

Disclosed herein is the antigen to which the specific binding members of the present invention bind. A Le$^y$ which is capable of being bound, preferably specifically, by a specific binding member of the present invention may be provided. The Le$^y$ may be provided in isolated form, and may be used in a screen to develop further specific binding members therefor. For example, a library of compounds may be screened for members of the library which bind specifically to the Le$^y$. The Le$^y$ may on a lipid or protein backbone. When on a protein backbone, it may have a molecular weight of about 50-150 kDa, as determined by SDS-PAGE.

In a further aspect the invention provides an isolated specific binding member capable of binding Le$^y$ containing glycans, preferably of the first aspect of the invention, for use in the diagnosis or prognosis of gastric, colorectal, pancreatic, lung, ovarian and breast tumours.

The invention further provides a method for diagnosis of cancer comprising using a specific binding member of the invention to detect Le$^y$ containing glycans in a sample from an individual. In the diagnostic method, the pattern of glycans detected by the binding member may be used to stratify therapy options for the individual.

These and other aspects of the invention are described in further detail below.

As used herein, a "specific binding member" is a member of a pair of molecules which have binding specificity for one another. The members of a specific binding pair may be naturally derived or wholly or partially synthetically produced. One member of the pair of molecules has an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of specific binding pairs are antigen-antibody, biotin-avidin, hormone-hormone receptor, 5 receptor-ligand, enzyme-substrate. The present invention is generally concerned with antigen-antibody type reactions, although it also concerns small molecules which bind to the antigen defined herein.

As used herein, "treatment" includes any regime that can benefit a human or non-human animal, preferably mammal. The treatment may be in respect of an existing condition or may be prophylactic (preventative treatment).

As used herein, a "tumour" is an abnormal growth of tissue. It may be localised (benign) or invade nearby tissues (malignant) or distant tissues (metastatic). Tumours include neoplastic growths which cause cancer and include oesophageal, colorectal, gastric, breast, ovarian and endometrial tumours, as well as cancerous tissues or cell lines including, but not limited to, leukaemic cells. As used herein, "tumour" also includes within its scope endometriosis.

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies of the invention are the immunoglobulin isotypes (e.g., IgG, IgE, IgM, IgD and IgA) and their isotypic subclasses; fragments which comprises an antigen binding domain such as Fab, scFv, Fv, dAb, Fd; and diabodies. Antibodies may be polyclonal or monoclonal. A monoclonal antibody may be referred to as a "mAb".

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, humanised antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023. A humanised antibody may be a modified antibody having the variable regions of a non-human, e.g., murine, antibody and the constant region of a human antibody. Methods for making humanised antibodies are described in, for example, U.S. Pat. No. 5,225,539.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, Gussow et al. 1989) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen binding site (Bird, Hardman et al. 1988, Huston, Levinson et al. 1988); (viii) bispecific single chain Fv dimers (PCT/US92/09965) and; (ix) "diabodies", multivalent or multispecific fragments constructed by gene fusion (WO94/13804; (Holliger, Prospero et al. 1993)).

Diabodies are multimers of polypeptides, each polypeptide comprising a first domain comprising a binding region of an immunoglobulin light chain and a second domain comprising a binding region of an immunoglobulin heavy chain, the two domains being linked (e.g., by a peptide linker) but unable to associated with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger and Winter 1993), e.g., prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction.

Other forms of bispecific antibodies include the single chain "Janusins" described in (Traunecker, Lanzavecchia et al. 1991).

Bispecific diabodies, as opposed to bispecific whole antibodies, may also be useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

A "binding domain" is the part of a specific binding member which comprises the area which specifically binds to and is complementary to part or all of an antigen. Where the binding member is an antibody or antigen-binding fragment thereof, the binding domain may be a CDR. Where an antigen is large, an antibody may only bind to a particular part of the antigen, which part is termed an epitope. An antigen binding domain may be provided by one or more antibody variable domains. An antigen binding domain may comprise an antibody light chain variable region (VL) and an antibody heavy chain variable region (VH).

"Specific" is generally used to refer to the situation in which one member of a specific binding pair will not show any significant binding to molecules other than its specific binding partner(s), and, e.g., has less than about 30%, preferably 20%, 10%, or 1% cross reactivity with any other molecule. The term is also applicable where e.g., an antigen binding domain is specific for a particular epitope which is carried by a number of antigens, in which case, the specific binding member carrying the antigen binding domain will be able to bind to the various antigens carrying the epitope. Specific binding members of the invention may be capable of binding specifically to Le$^y$ in the sense that there is no detectable binding to any other antigen (such as any other glycan) when binding is tested according to the protocol set out in "Glycome Analysis" in the Examples herein.

"Isolated" refers to the state in which specific binding members of the invention or nucleic acid encoding such binding members will preferably be, in accordance with the present invention. Members and nucleic acid will generally be free or substantially free of material with which they are naturally associated such as other polypeptides or nucleic acids with which they are found in their natural environment, or the environment in which they are prepared (e.g., cell culture) when such preparation is by recombinant DNA technology practised in vitro or in vivo. Specific binding members and nucleic acid may be formulated with diluents or adjuvants and still for practical purposes be isolated—for example, the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

By "substantially as set out" it is meant that the amino acid sequence(s) of the invention will be either identical or highly homologous to the amino acid sequence(s) referred to. By "highly homologous" it is contemplated that there may be from 1 to 5, from 1 to 4, from 1 to 3, 2 or 1 substitutions may be made in the sequence.

The invention also includes within its scope polypeptides having the amino acid sequence as set out in FIG. 1, 2 or 3, polynucleotides having the nucleic acid sequences as set out in FIG. 1 or 2 and sequences having substantial identity thereto, for example at least 70%, at least 80%, at least 85%, at least 90%, at least 95% or at least 99% identity thereto. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul, 1990 (Karlin and Altschul 1990), modified as in Karlin and Altschul, 1993 (Karlin and Altschul 1993). The NBLAST and XBLAST programs of Altschul et al., 1990 (Altschul, Gish et al. 1990) have incorporated such an algorithm. BLAST nucleotide searches can be performed with the NBLAST program, score=100, word length=12 to obtain nucleotide sequences homologous to a nucleic acid molecules of the invention. BLAST protein searches can be performed with the XBLAST program, score=50, word length=3 to obtain amino acid sequences homologous to a protein molecules of the invention. To obtain gapped alignments for comparison purposes, Gapped BLAST can be utilised as described in Altschul et al., 1997 (Altschul, Madden et al. 1997). Alternatively, PSI-Blast can be used to perform an iterated search that detects distant relationships between molecules (Id.). When utilizing BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, 1989 (Myers and Miller 1989). The ALIGN program (version 2.0) which is part of the GCG sequence alignment software package has incorporated such an algorithm. Other algorithms for sequence analysis known in the art include ADVANCE and ADAM as described in Torellis and Robotti, 1994 (Torelli and Robotti 1994); and FASTA described in Pearson and Lipman, 1988 (Pearson and Lipman 1988). Within FASTA, ktup is a control option that sets the sensitivity and speed of the search.

Isolated specific binding members of the present invention are capable of binding to a Le$^y$ carbohydrate, which may be a Le$^y$ ceramide or may be on a protein moiety. The binding domains, comprising the amino acid sequences substantially as set out as residues 105 to 116 (CDRH3) of FIGS. 1a and 1b and 105 to 113 of FIG. 1c, may be carried in a structure which allows the binding of these regions to a Le$^y$ carbohydrate.

The structure for carrying the binding domains of the invention will generally be of an antibody heavy or light chain sequence or substantial portion thereof in which the binding domains are located at locations corresponding to the CDR3 region of naturally-occurring VH and VL antibody variable domains encoded by rearranged immunoglobulin genes. The structures and locations of immunoglobulin variable domains may be determined by reference to http://www.imgt.org/. The amino acid sequence substantially as set out as residues 105 to 116 of FIGS. 1*a* and 1*b* may be carried as the CDR3 in a human heavy chain variable domain or a substantial portion thereof, and the amino acid sequence substantially as set out as residues and 105 to 113 of FIG. 1*c* may be carried as the CDR3 in a human light chain variable domain or a substantial portion thereof.

The variable domains may be derived from any germline or rearranged human variable domain, or may be a synthetic variable domain based on consensus sequences of known human variable domains. The CDR3-derived sequences of the invention may be introduced into a repertoire of variable domains lacking CDR3 regions, using recombinant DNA technology. For example, Marks et al., 1992 (Marks, Griffiths et al. 1992) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al., 1992 (Marks, Griffiths et al. 1992) further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer, 1994 (Stemmer 1994) who describes the technique in relation to a beta-lactamase gene but observes that the approach may be used for the generation of antibodies. A further alternative is to generate novel VH or VL regions carrying the CDR3-derived sequences of the invention using random mutagenesis of, for example, the FG27VH or VL genes to generate mutations within the entire variable domain. Such a technique is described by Gram et al., 1992 (Gram, Marconi et al. 1992), who used error-prone PCR.

Another method which may be used is to direct mutagenesis to CDR regions of VH or VL genes. Such techniques are disclosed by Barbas et al., 1994 (Barbas, Hu et al. 1994) and Schier et al., 1996 (Schier, McCall et al. 1996). A substantial portion of an immunoglobulin variable domain will generally comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps, including the introduction of linkers to join variable domains of the invention to further protein sequences including immunoglobulin heavy chains, other variable domains (for example in the production of diabodies) or protein labels as discussed in more detail below.

The invention provides specific binding members comprising a pair of binding domains based on the amino acid sequences for the VL and VH regions substantially as set out in FIG. 1, i.e., amino acids 1 to 127 (VH) of FIG. 1*a* or 1*b* and amino acids 1 to 124 (VL) of FIG. 1*c*. Single binding domains based on either of these sequences form further aspects of the invention. In the case of the binding domains based on the amino acid sequence for the VH region substantially set out in FIGS. 1*a* and 1*b*, such binding domains may be used as targeting agents since it is known that immunoglobulin VH domains are capable of binding target antigens in a specific manner. In the case of either of the single chain specific binding domains, these domains may be used to screen for complementary domains capable of forming a two-domain specific binding member which has in vivo properties as good as or equal to the FG27 antibodies disclosed herein.

This may be achieved by phage display screening methods using the so-called hierarchical dual combinatorial approach as disclosed in WO92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al., 1992 (Marks, Griffiths et al. 1992).

Specific binding members of the present invention may further comprise antibody constant regions or parts thereof. For example, specific binding members based on the VL region shown in FIG. 1*c* may be attached at their C-terminal end to antibody light chain constant domains Similarly, specific binding members based on VH region shown in FIGS. 1*a* and 1*b* may be attached at their C-terminal end to all or part of an immunoglobulin heavy chain derived from any antibody isotype, e.g., IgG, IgA, IgE and IgM and any of the isotype sub-classes, particularly IgG1, IgG2 and IgG4.

Specific binding members of the present invention can be used in methods of diagnosis and treatment of tumours in human or animal subjects.

When used in diagnosis, specific binding members of the invention may be labelled with a detectable label, for example a radiolabel such as $^{131}$I or $^{99}$Tc, which may be attached to specific binding members of the invention using conventional chemistry known in the art of antibody imaging. Labels also include enzyme labels such as horseradish peroxidase. Labels further include chemical moieties such as biotin which may be detected via binding to a specific cognate detectable moiety, e.g., labelled avidin.

Although specific binding members of the invention have in themselves been shown to be effective in killing cancer cells, they may additionally be labelled with a functional label. Functional labels include substances which are designed to be targeted to the site of cancer to cause destruction thereof. Such functional labels include toxins such as ricin and enzymes such as bacterial carboxypeptidase or nitroreductase, which are capable of converting prodrugs into active drugs. In addition, the specific binding members may be attached or otherwise associated with chemotherapeutic or cytotoxic agents, such as maytansines (DM1 and DM4), onides, auristatins, calicheamicin, duocamycin, doxorubicin or radiolabels, such as $^{90}$Y or $^{131}$I.

Furthermore, the specific binding members of the present invention may be administered alone or in combination with other treatments, either simultaneously or sequentially, dependent upon the condition to be treated. Thus, the present invention further provides products containing a specific binding member of the present invention and an active agent as a combined preparation for simultaneous, separate or sequential use in the treatment of a tumour. Active agents may include chemotherapeutic or cytotoxic agents including, 5-Fluorouracil, cisplatin, Mitomycin C, oxaliplatin and tamoxifen, which may operate synergistically with the binding members of the present invention. Other active agents may include suitable doses of pain relief drugs such as non-steroidal anti-inflammatory drugs (e.g., aspirin, paracetamol, ibuprofen or ketoprofen) or opitates such as morphine, or anti-emetics.

Whilst not wishing to be bound by theory, the ability of the binding members of the invention to synergise with an active agent to enhance tumour killing may not be due to immune effector mechanisms but rather may be a direct consequence of the binding member binding to cell surface bound Le$^y$ glycans. Cancer immunotherapy, involving antibodies to immune checkpoint molecules, have shown effectiveness to various malignances and in combinations with different immune-oncology treatment modalities.

Specific binding members of the present invention will usually be administered in the form of a pharmaceutical composition, which may comprise at least one component in addition to the specific binding member. The pharmaceutical composition may comprise, in addition to active ingredient, a pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g., intravenous. It is envisaged that injections will be the primary route for therapeutic administration of the compositions although delivery through a catheter or other surgical tubing is also used. Some suitable routes of administration include intravenous, subcutaneous, intraperitoneal and intramuscular administration. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Implantable or microcapsular sustained release matrices include polylactides (US Patent No. 3, 773, 919; EP-A-0058481) copolymers of L-glutamic acid and gamma ethyl-L-glutamate (Sidman, Steber et al. 1983), poly (2-hydroxy-ethyl-methacrylate). Liposomes containing the polypeptides are prepared by well-known methods: DE 3,218, 121A; (Eppstein, Marsh et al. 1985); (Hwang, Luk et al. 1980); EP-A-0052522; EP-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage. The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences, 16th edition, Oslo, A. (ed), 1980 (Remington 1980).

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately 0.1 nM is normally sufficient. For example, a dose of 100 mg/m$^2$. of antibody provides a serum concentration of approximately 20 nM for approximately eight days.

As a rough guideline, doses of antibodies may be given weekly in amounts of 10-300 mg/m$^2$. Equivalent doses of antibody fragments should be used at more frequent intervals in order to maintain a serum level in excess of the concentration that permits saturation of the Le$^y$ carbohydrate. The dose of the composition will be dependent upon the properties of the binding member, e.g., its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 300 μg of antibody per patient per administration are preferred, although dosages may range from about 10 μg to 6 mg per dose. Different dosages are utilised during a series of sequential inoculations; the practitioner may administer an initial inoculation and then boost with relatively smaller doses of antibody.

This invention is also directed to optimise immunisation schedules for enhancing a protective immune response against cancer.

The binding members of the present invention may be generated wholly or partly by chemical synthesis. The binding members can be readily prepared according to well-established, standard liquid or, preferably, solid-phase peptide synthesis methods, general descriptions of which are broadly available (see, for example, in J. M. Stewart and J. D. Young, 1984 (Stewart and Young 1984), in M. Bodanzsky and A. Bodanzsky, 1984 (Bodanzsky and Bodanzsky 1984) or they may be prepared in solution, by the liquid phase method or by any combination of solid-phase, liquid phase and solution chemistry, e.g., by first completing the respective peptide portion and then, if desired and appropriate, after removal of any protecting groups being present, by introduction of the residue X by reaction of the respective carbonic or sulfonic acid or a reactive derivative thereof.

Another convenient way of producing a binding member according to the present invention is to express the nucleic acid encoding it, by use of nucleic acid in an expression system.

The present invention further provides an isolated nucleic acid encoding a specific binding member of the present invention. Nucleic acid includes DNA and RNA. In a preferred aspect, the present invention provides a nucleic acid which codes for a specific binding member of the invention as defined above. Examples of such nucleic acid are shown in FIGS. 1 and 2. The skilled person will be able to determine substitutions, deletions and/or additions to such nucleic acids which will still provide a specific binding member of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a specific binding member of the invention forms an aspect of the present invention, as does a method of production of the specific binding member which method comprises expression from encoding nucleic acid. Expression may conveniently be achieved by culturing under appropriate conditions recombinant host cells containing the nucleic acid. Following production by expression, a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, Hela cells, baby hamster kidney cells, NSO mouse melanoma cells and many others. A common, preferred bacterial host is *E. coli*. The expression of antibodies and antibody fragments in prokaryotic cells such as *E. coli* is well established in the art. For a review, see for example Plückthun, 1991 (Pluckthun 1991). Expression in eukaryotic cells in culture is also available to those skilled in the art as an option for production of a specific binding member, see for recent review, for example Reff, 1993 (Reff 1993); Trill et al., 1995 (Trill, Shatzman et al. 1995).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., 'phage, or phagemid, as appropriate. For further details see, for example, Sambrook et al., 1989 (Sambrook 1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al., 1992 (Ausubel 1992).

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene.

The nucleic acid of the invention may be integrated into the genome (e.g., chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

Preferred features of each aspect of the invention are as for each of the other aspects mutatis mutandis. The prior art documents mentioned herein are incorporated to the fullest extent permitted by law.

The inventors have unexpectedly found that a family of mAbs FG27 recognise Le$^y$ containing glycans induced non-apoptotic direct cell death without immune effector cells. In one aspect, of the present invention it provides drugs which bind to Le$^y$ containing glycan and induce non-apoptotic cell death.

FG27 mAbs induced membrane damage to cells resulting in cell clumping, loss of microvilli, uptake of small molecular weight dyes and pore formation. Over time cells developed larger pores and lysed in a mechanism similar to oncosis. This is similar to a number of mAbs recognising other glycans (Hellstrom, Garrigues et al. 1990, Chou, Takematsu et al. 1998, Zhong, Manzi et al. 2001, Alvarez-Rueda, Leprieur et al. 2007, Loo, Pryer et al. 2007, Zhang, Zhang et al. 2010). The FG27 mAbs also exhibited potent in vitro cytotoxic activity through ADCC and CDC. The administration of FG27 (0.1 mg intravenous (i.v.) twice a week for 9 weeks) to mice with established metastases in the liver and peritoneal cavity resulted in complete tumour eradication and cure of ~30% of the mice. The potential of FG27 mAbs in eradicating well-established tumours without concomitant chemotherapy indicates their potential as monotherapeutic agents for the treatment of Le$^y$ expressing human solid tumours.

The invention will now be described further in the following non-limiting examples and accompanying drawings, in which:

FIG. 1*a*: Complete amino acid and nucleotide sequence of the mouse FG27.10 IgG3 heavy chain. Numbers refer to the standardised IMGT system for the numbering of antibody sequences (Lefranc, Giudicelli et al. 2009). FIG. 1*b*: Complete amino acid and nucleotide sequence of mouse FG27.18 IgG1 heavy chain. Numbers refer to the standardised IMGT system for the numbering of antibody sequences (Lefranc, Giudicelli et al. 2009). FIG. 1*c*: Complete amino acid and nucleotide sequence of mouse FG27.10 and FG27.18 kappa chain. Numbers refer to the standardised IMGT system for the numbering of antibody sequences (Lefranc, Giudicelli et al. 2009).

Figure 2B:
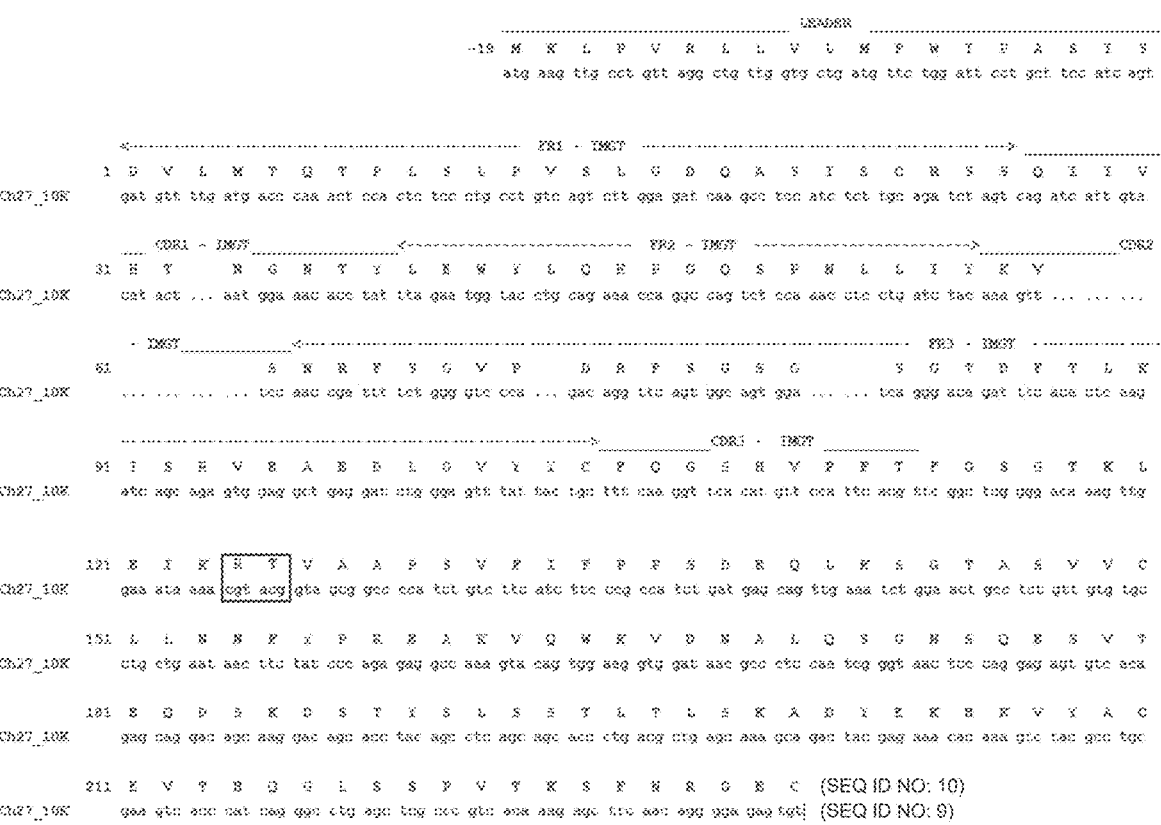

FIG. 2a: Complete amino acid and nucleotide sequence of mouse FG27 heavy chain variable region chimerised to human IgG1 heavy chain constant region. Numbers refer to the standardised IMGT system for the numbering of antibody sequences (Lefranc, Giudicelli et al. 2009). FIG. 2b: Complete amino acid and nucleotide sequence of mouse FG27 kappa chain variable region chimerised to human kappa chain constant region. Numbers refer to the standardised IMGT system for the numbering of antibody sequences (Lefranc, Giudicelli et al. 2009).

FIG. 3a: Complete amino acid and nucleotide sequence of the humanised FG27 heavy chain variable region. Numbers refer to the standardised IMGT system for the numbering of antibody sequences (Lefranc, Giudicelli et al. 2009). FIG. 3b: Complete amino acid and nucleotide sequence of humanised FG27 kappa chain variable region. Numbers refer to the standardised IMGT system for the numbering of antibody sequences (Lefranc, Giudicelli et al. 2009).

Figure 4:
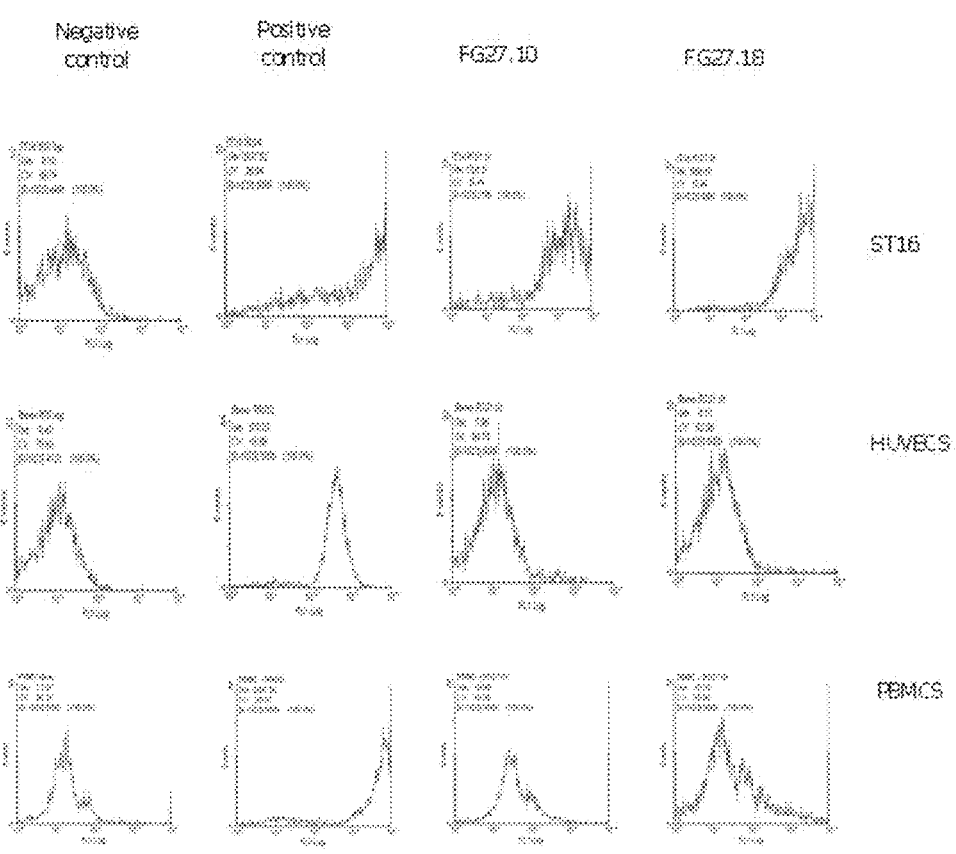

FIG. 4: Binding of FG27.10 and FG27.18 to ST16, HUVEC and PBMCs. The negative control for this assay was NSO supernatant for ST16 and HUVEC, or cell alone for the PBMCs and the positive control was either the anti-sialyl-di Le$^a$ mAb, 505/4, or W6/32 which recognises HLA.

Figure 5:
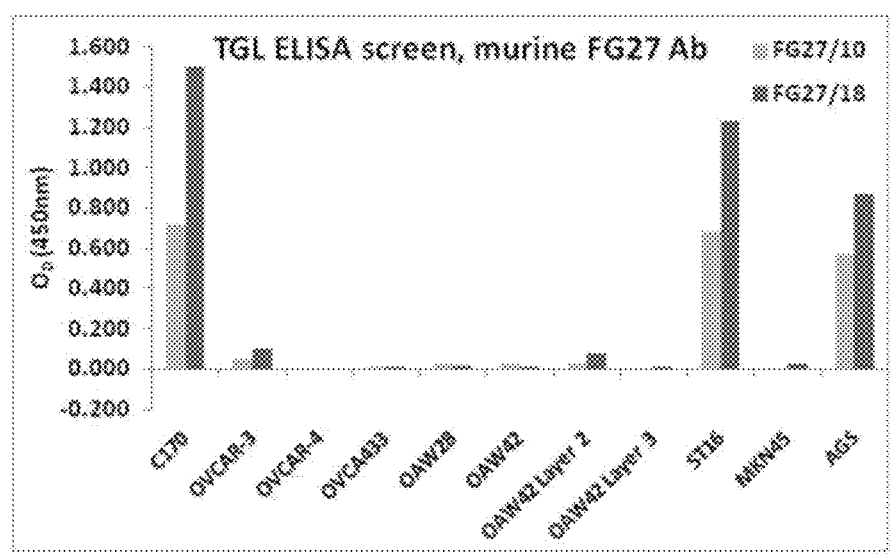

FIG. 5: Binding of FG27.10 and FG27.18 to glycolipid extracts from colorectal (C170), ovarian (OVCAR-3, OVCAR-4, OVCA433, OAW28, OAW42) and gastric cell lines (ST16, MKN45, AGS). Glycolipid extracted from a range of cancer cell lines was plated on ELISA plates. Cells and glycolipid were then incubated with FG27.10 or FG27.18 supernatant. Binding to glycolipid was probed with anti-IgG-HRP/TMB.

Figure 6:
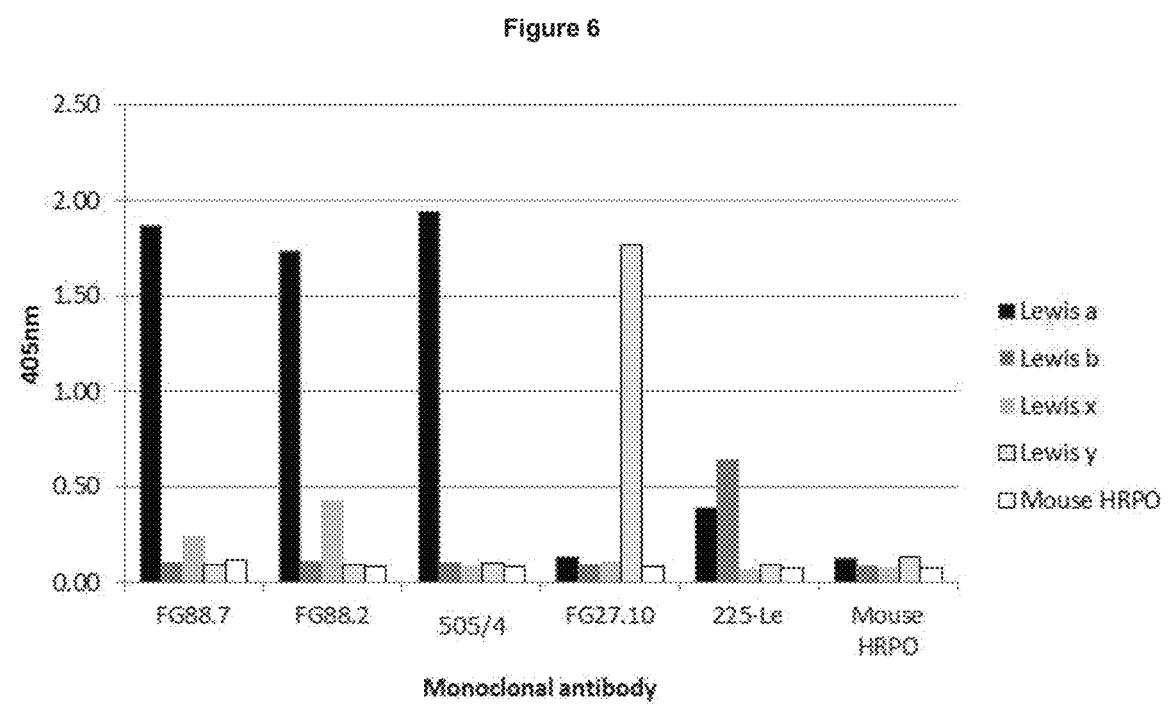

FIG. 6: Binding of FG27.10 to HSA coupled Lewis antigens (a, b, x and y) as assessed by ELISA. 505/4 (anti-sialyl-di-Le$^a$), FG88.2 (Le$^{a-x}$), FG88.7 (Le$^{a-x}$) and 225-Le (Le$^b$) were included as positive controls and mouse HRPO as the negative. Antibody activity was measured by absorbance at 405 nm.

FIG. 7: Binding of FG27.10 and FG27.18 were screened against The Consortium for Functional Glycomics glycan array which is composed of 610 mammalian glycan targets. The fine specificity between a) FG27.10, b) FG27.18, c) 692 (Le$^{y/b}$), and d) BR96 (Le$^{y/x}$) are compared; where a=Le$^a$, b=Le$^b$, y=Le$^y$, x=Le$^x$, D-=Di, T-=Tri, S-=sialyl, Ex-=extended, q denotes a mannose containing glycan, and y-x=Le$^y$-Le$^x$. Note due to the mAbs being screened on different versions of the glycan array, the glycan numbers may not be the same for each mAb.

Figure 8:

FIG. 8: Binding of FG27 to Le$^y$ attached to total proteins or lipids extracted from a panel of tumour cell lines. Western blot detection of FG27 binding to Le$^y$ associated with total glycoproteins or glycolipids extracted from the tumour cell lines, AGS, HCT15, OVCAR3, MCF7 and H322 cell lysates ($1 \times 10^5$ cells equivalent).

FIG. 9: Comparison of anti-Le$^y$ and Le$^b$ mAbs on a range of cell lines. SC101 (692/29) and BR96 were titrated across a range of cell lines (ST16, HT29, C170, LoVo, Colo201, OVCAR-3, AGS) at 0.1-30 µg/ml, with FG27 supernatant being diluted from neat to 1:30. Binding was probed with anti-IgG-FITC and analysed by flow cytometry.

Figure 10:
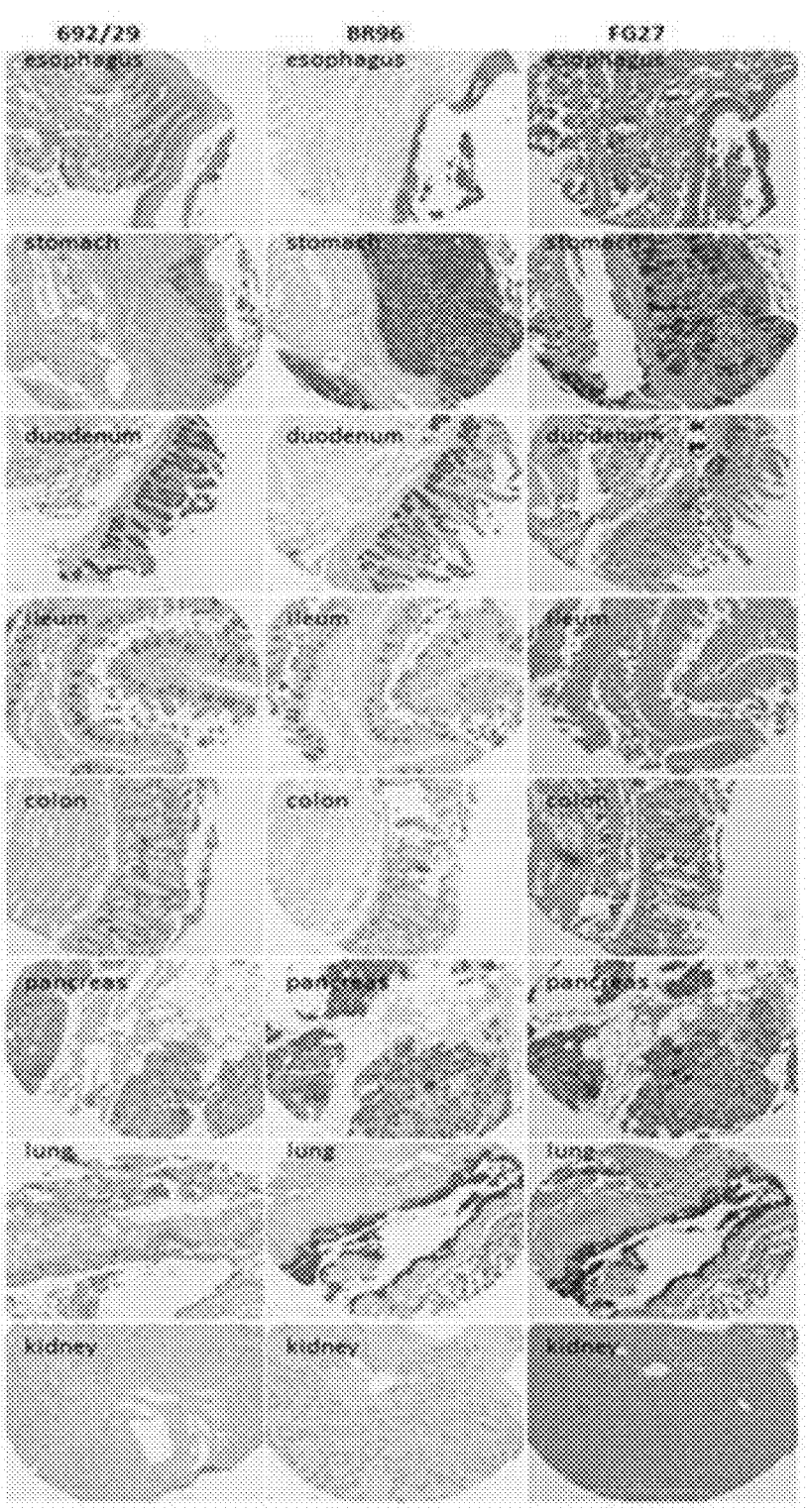

FIG. 10: Representative IHC images of normal oesophagus, stomach, duodenum, ileum, colon, pancreas, lung and kidney stained with 692/29 (Le$^{y/b}$), BR96 (Le$^{y/x}$) and FG27 (Le$^y$).

Figure 11A:
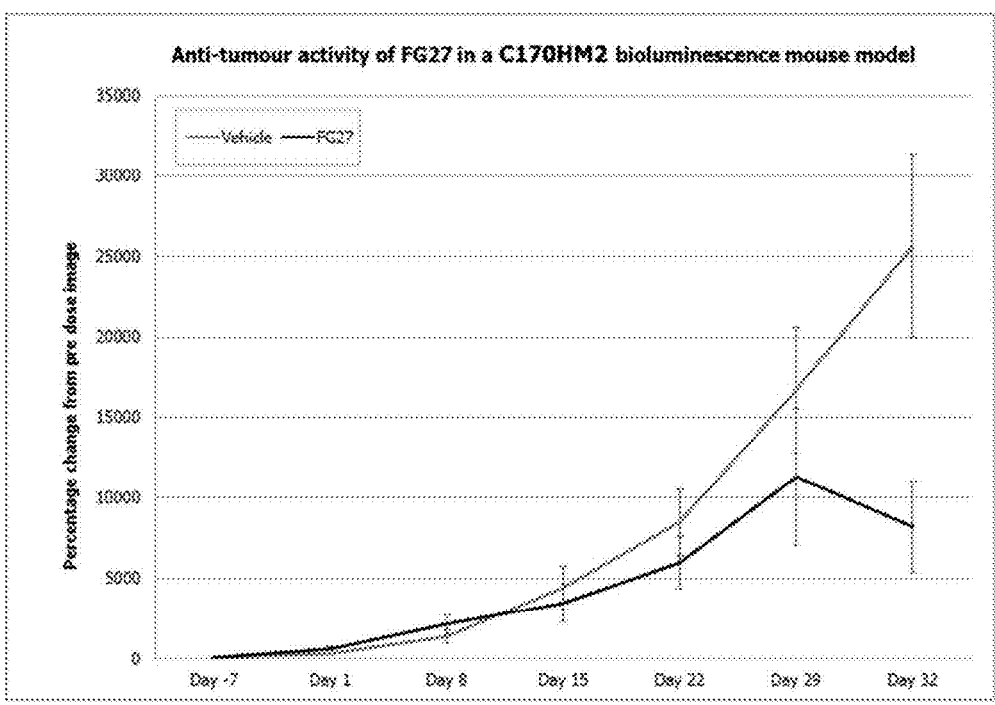
Figure 11B:
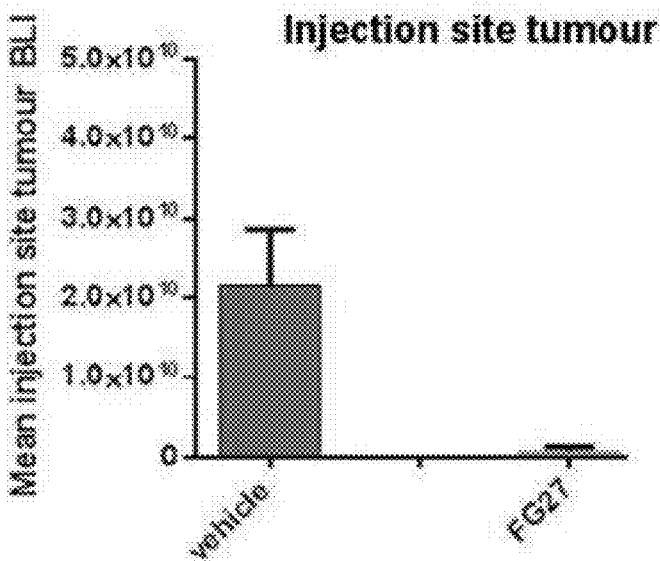

FIG. 11a: In vivo anti-tumour activity of FG27. Percentage tumour growth over the duration of the study is shown with the C170HM2 bioluminescence mouse tumour model used to assess the anti-tumour activity of the murine FG27 mAb compared to the vehicle only control (PBS). In this model bioluminescence represents viability. Group n≥9; the study was terminated on day 32. Treatment with FG27 resulted in a significant reduction in bioluminescent tumour burden by the last day of the study compared to the vehicle control (p=0.014). FIG. 11b: Injection site tumour burden as assessed by BLI, showing a significant reduction in injection site tumour growth with FG27 treatment (p=0.05).

Figure 12A:
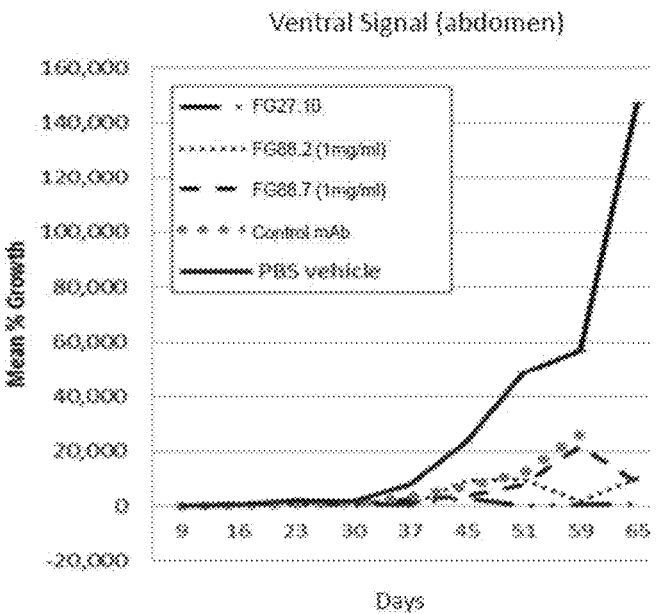
Figure 12B:
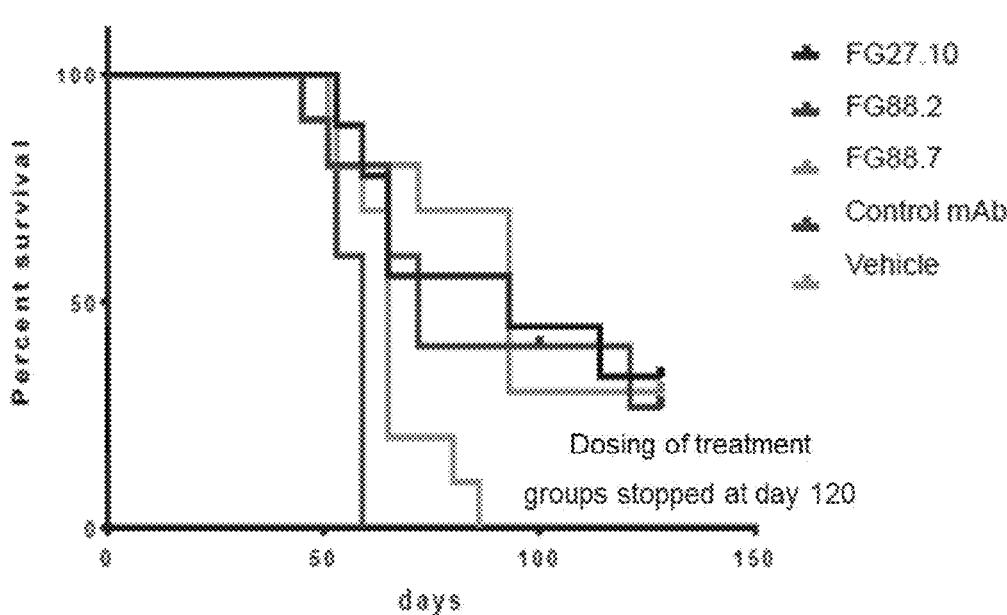

FIG. 12: In vivo anti-tumour activity of FG27; Percentage tumour growth is shown with the C170HM2 bioluminescence mouse tumour model used to assess the anti-tumour activity of FG27 compared to the positive control mAbs and vehicle only control (PBS). Bioluminescence represents tumour cell viability in this model. Group n≥8; the treatment with FG27 produced a significant reduction in percentage tumour growth by day 51 (p=0.009) compared to the treatment control. FIG. 12b: Analysis by Log Rank Mantel-Cox test demonstrates significant survival in the FG27 (p=0.035) treatment group compared to the vehicle only control. Treatment was stopped at day 120.

Figure 13B:
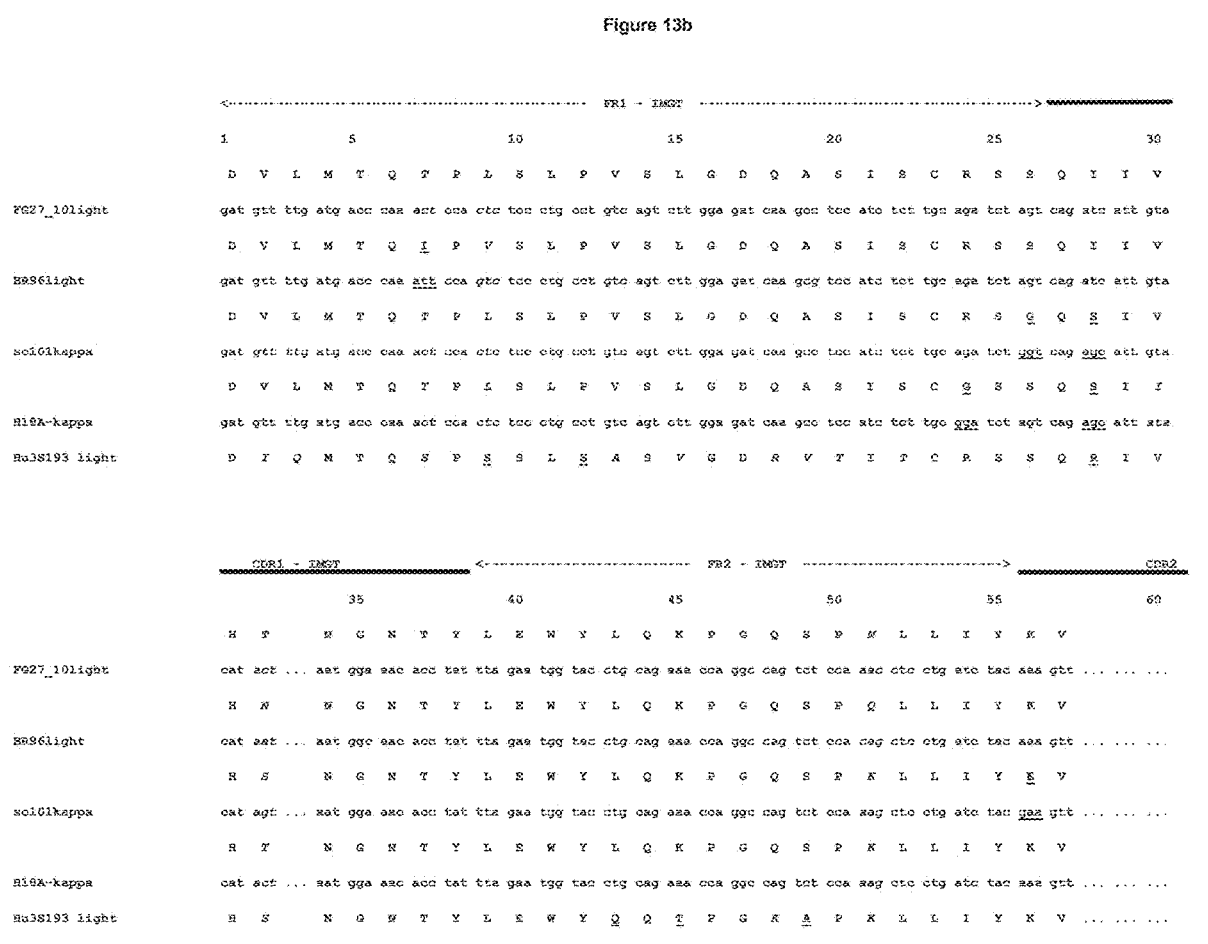
Figure 13B:
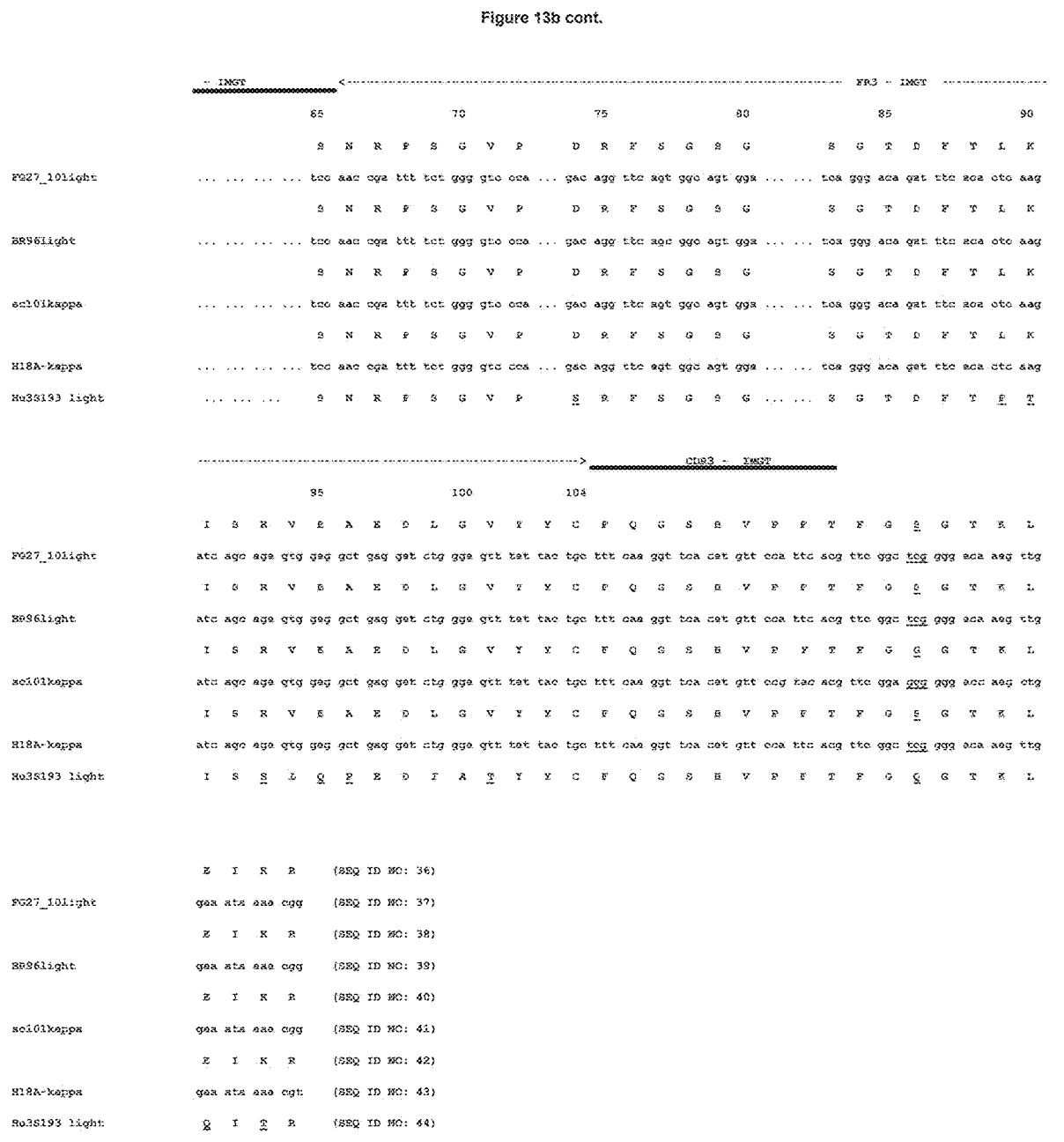

FIG. 13a: Amino acid and nucleotide sequence of mouse FG27 heavy chain variable region compared to BR96, H18A, Hu3S193 and SC101 using the standardised IMGT system for the numbering of antibody sequences (Lefranc, Giudicelli et al. 2009). FIG. 13b: Amino acid and nucleotide sequence of mouse FG27 kappa chain variable region compared to BR96, SC101, H18A, Hu3S193 using the standardised IMGT system for the numbering of antibody sequences (Lefranc, Giudicelli et al. 2009).

Figure 14:
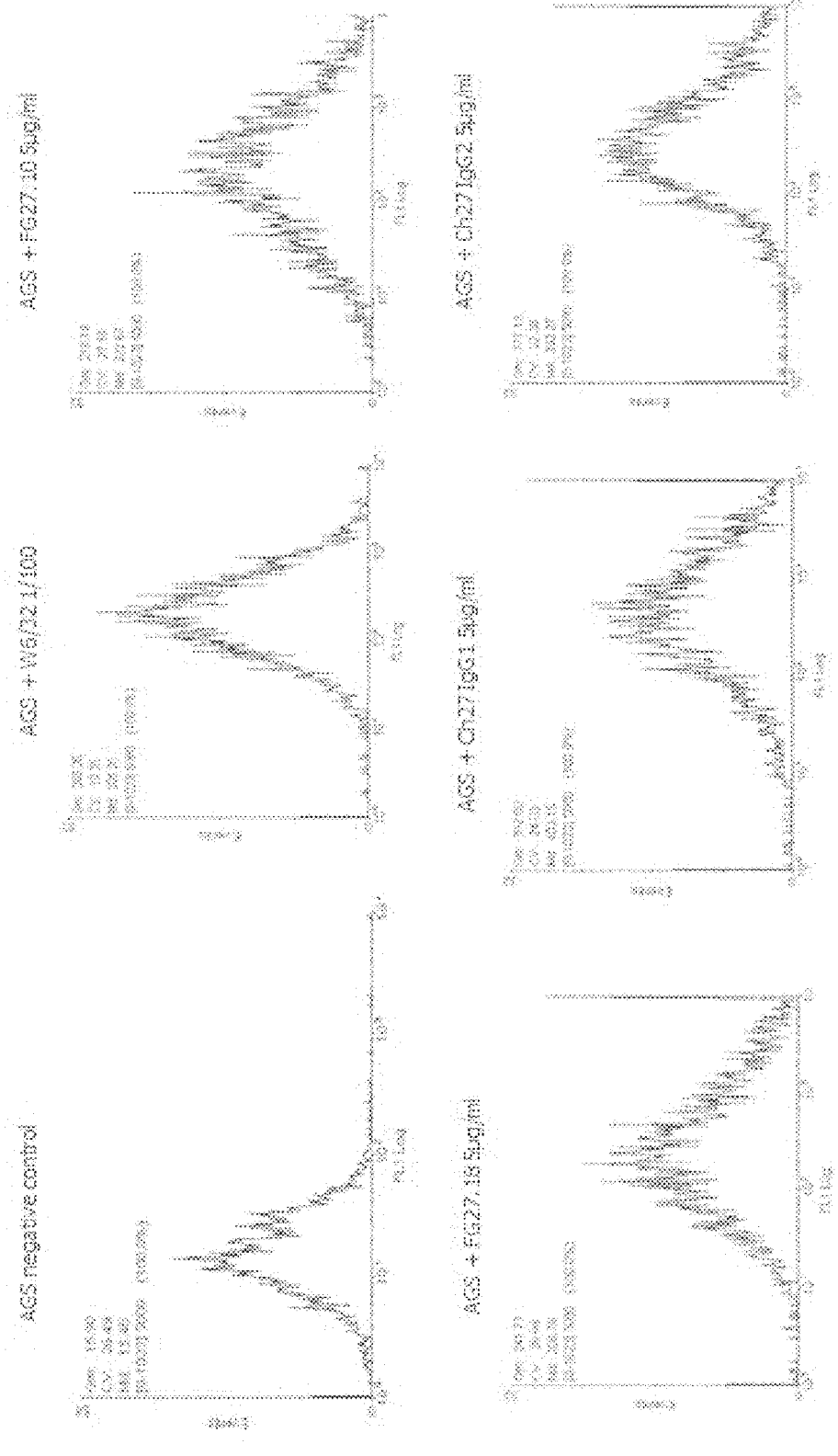

FIG. 14: Binding, as assessed by indirect immunofluorescence and flow cytometric analysis, of chimeric IgG1 (5 µg/ml) and IgG2 (5 µg/ml) mAbs to the Le$^y$ expressing tumour cell line, AGS are compared to the FG27.10 (5 µg/ml) and FG27.18 (5 µg/ml) murine versions of the antibody. The anti-HLA mAb, W6/32 (1/100) was included as a positive control.

Figure 15A:
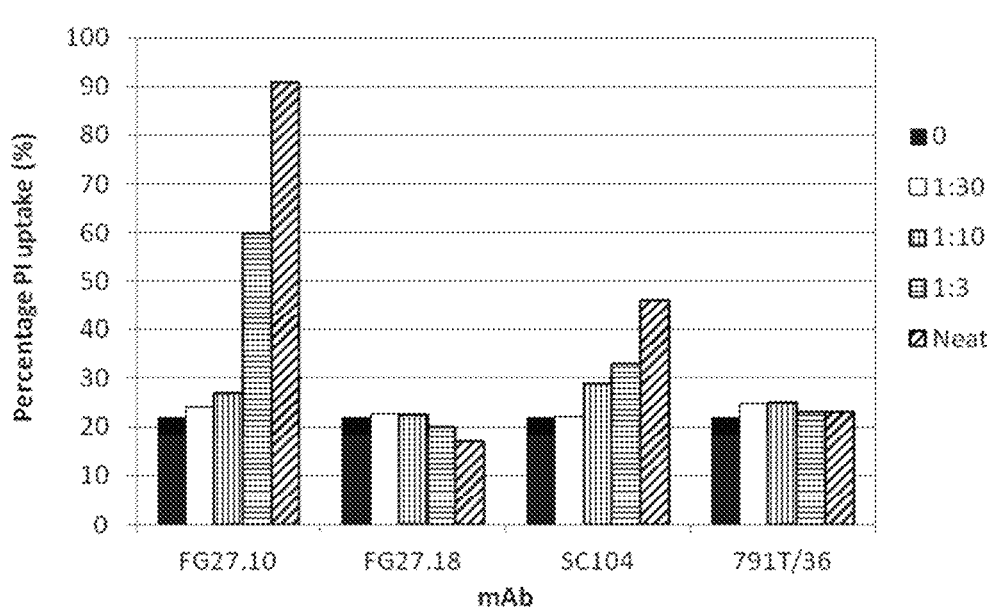
Figure 15B:
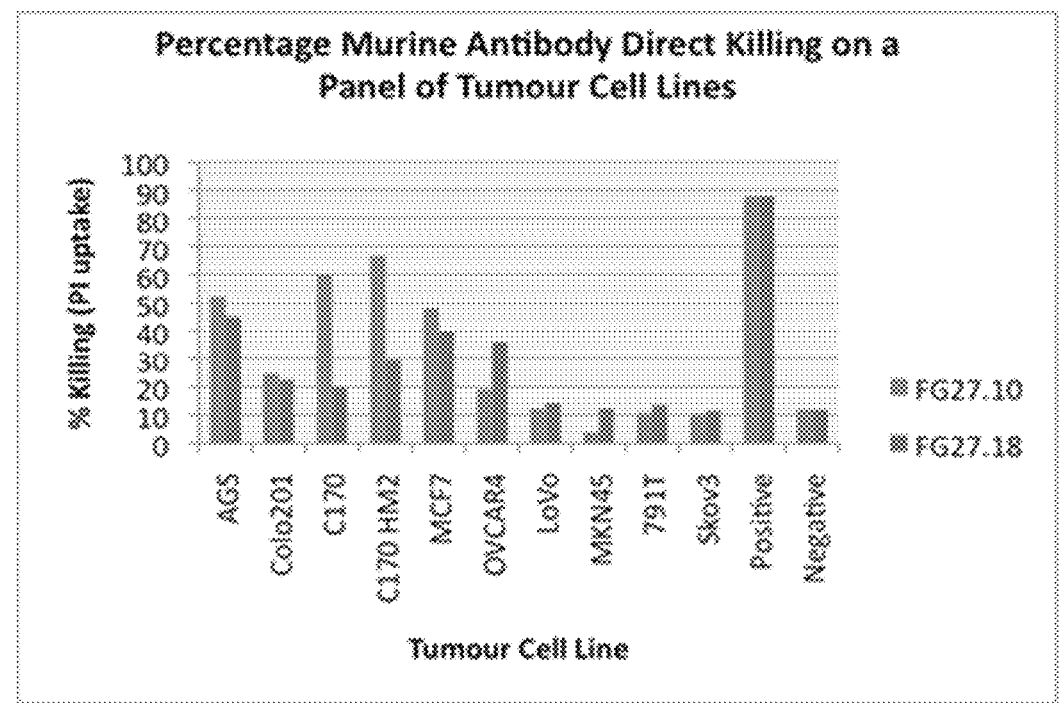
Figure 15C:
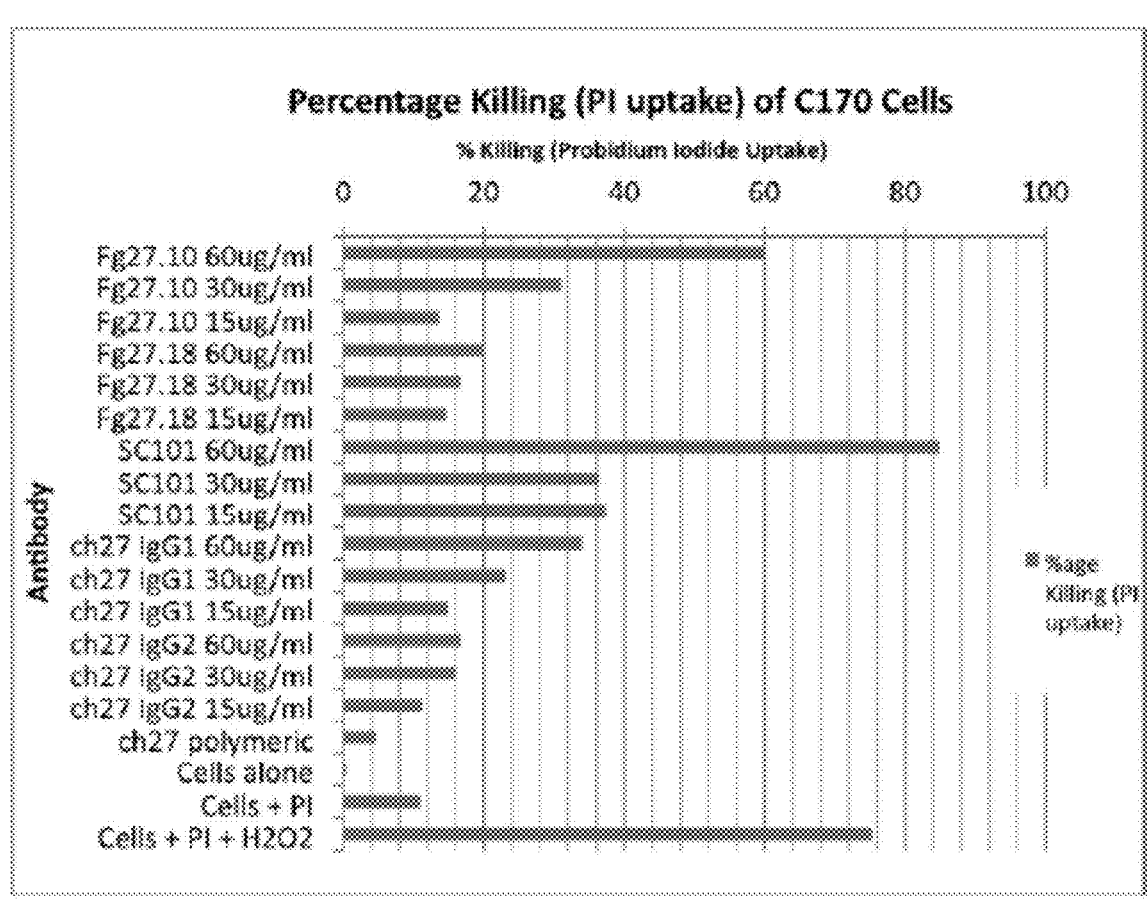

FIG. 15a: PI uptake of ST16 cells mediated by the mouse IgG3 mAb FG27.10 induced potent uptake of PI even at 4° C. but the IgG1 variant FG27.18 did not. FIG. 15b: PI uptake mediated by FG27.10 and FG27.18 on a panel of tumour cell lines (AGS, Colo201, C170, C170HM2, MCF7, OVCA4, LoVo, MKN45, 791T and Skov3). FIG. 15c: PI uptake mediated by FG27.10, FG27.18, CH27 IgG2, CH27 IgG1 on C170 cells.

Figure 16:
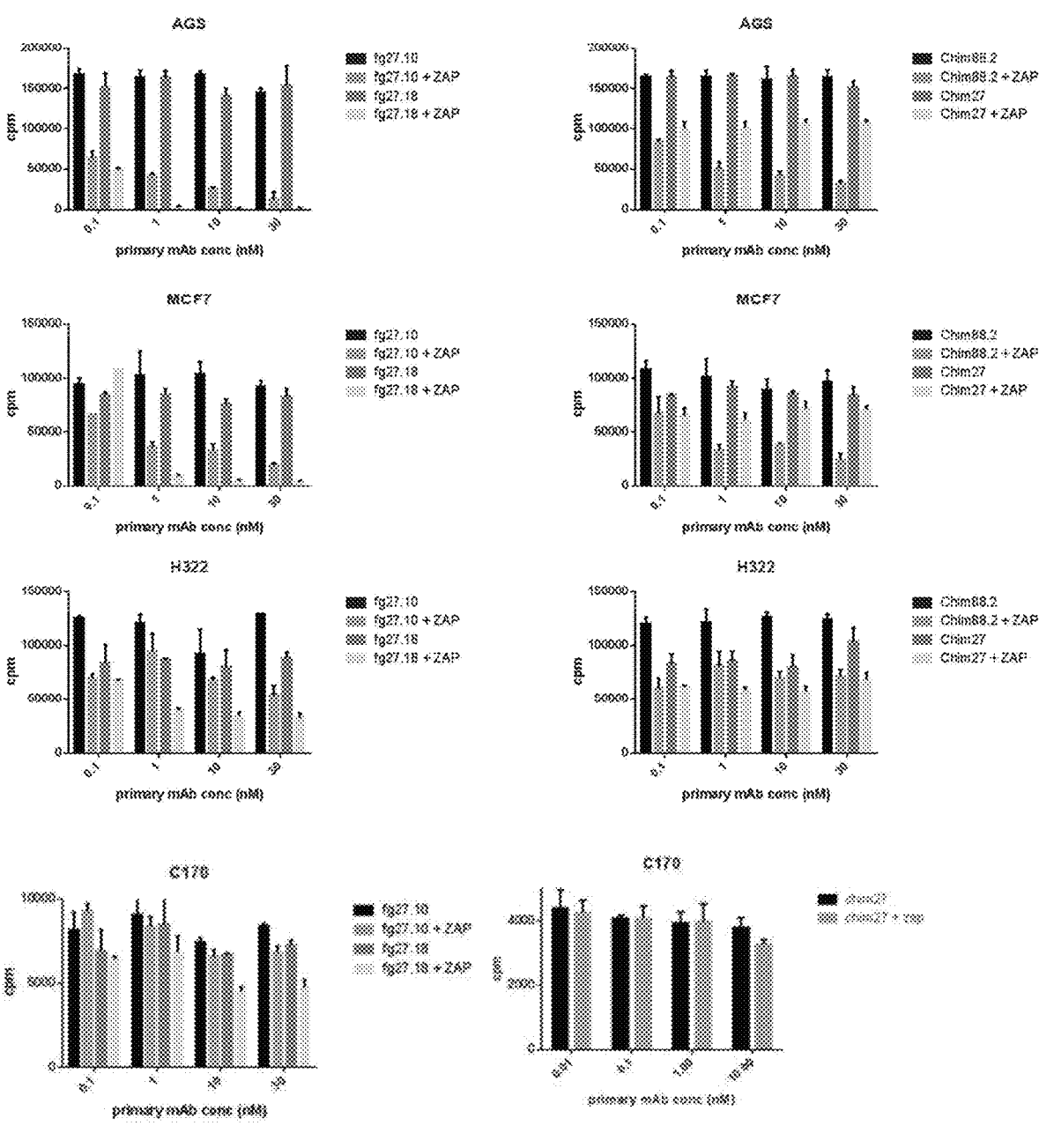

FIG. 16: FG27.10, FG27.18 and CH27 internalisation data over a range of concentrations (0.01 nM to 30 nM) on a panel of cancer cell lines, AGS, MCF7, H322 and C170. Cellular internalisation of the mAbs was observed using 75 ng/well saporin-conjugated goat antibody (F'ab fragment) to mouse (ATSbio, IT #48) or human IgG (ZAP) and assessed by inhibition of thymidine uptake (added for the last 24 hrs of the incubation). Control wells consisted of cells incubated with culture medium only, with the irrelevant positive control IgG3 mAb FG88 and with secondary conjugate only.

Figure 17B:
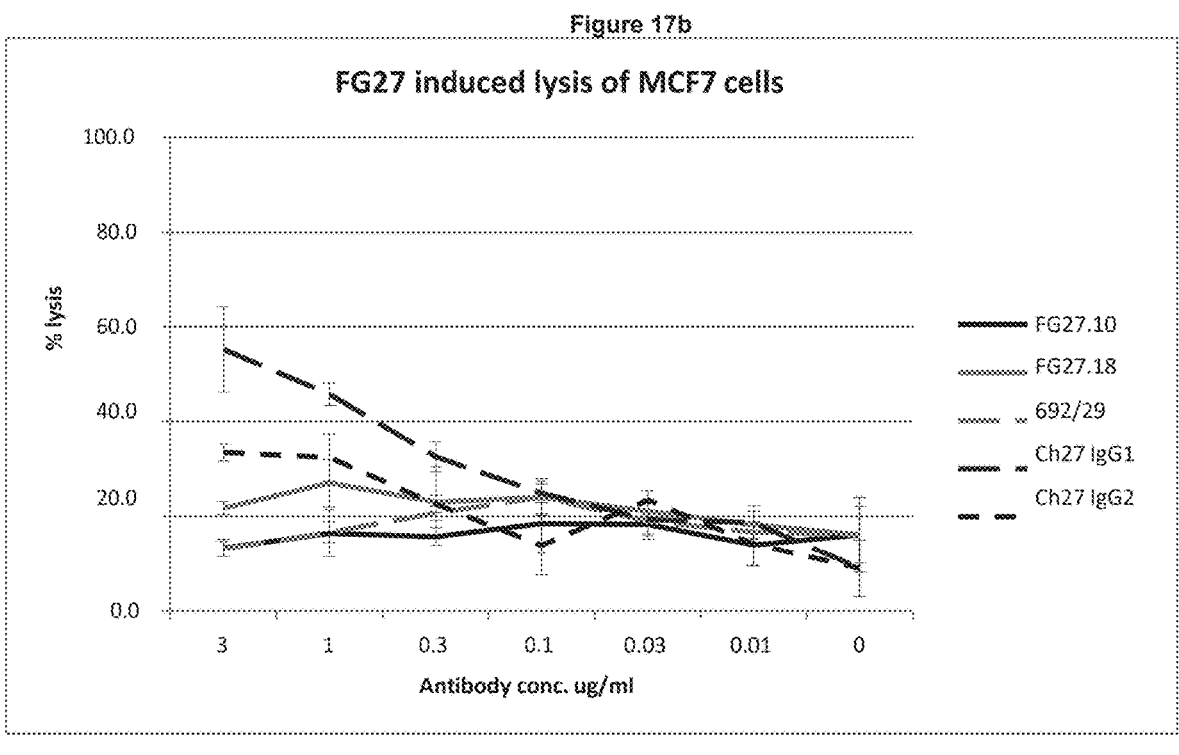
Figure 17C:
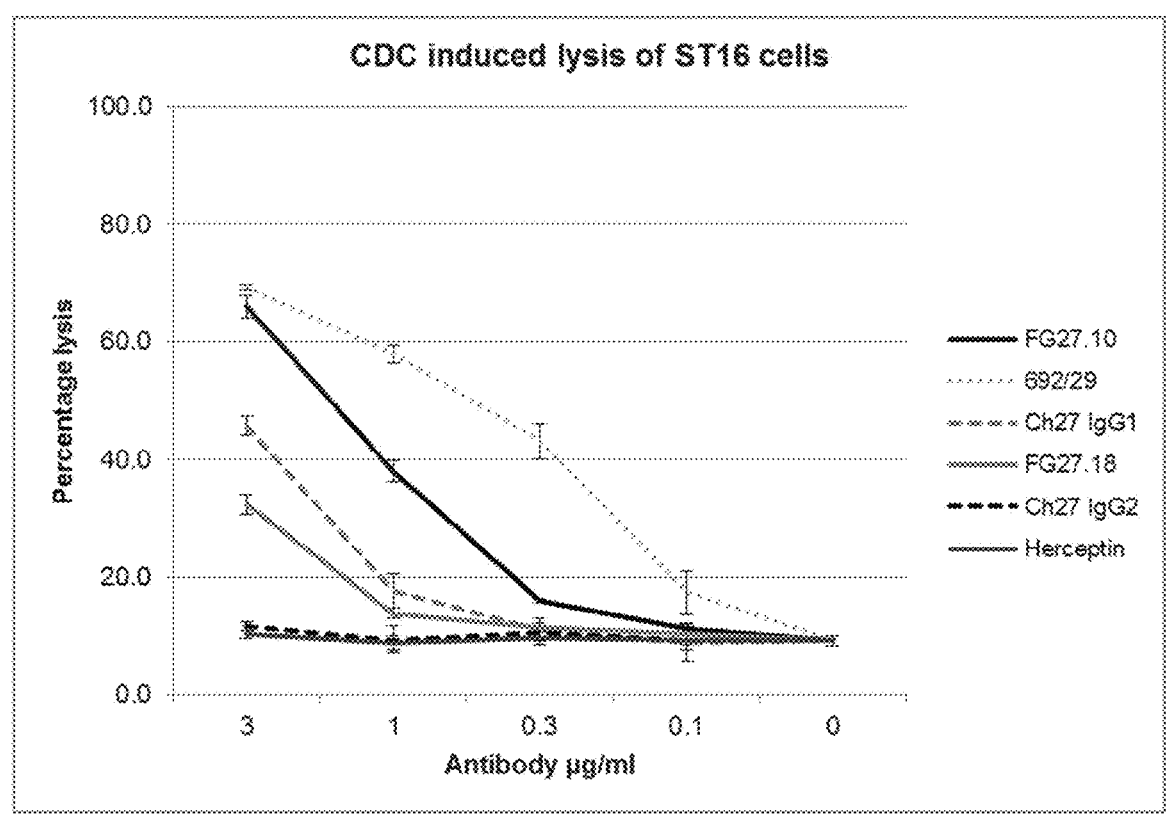
Figure 17D:
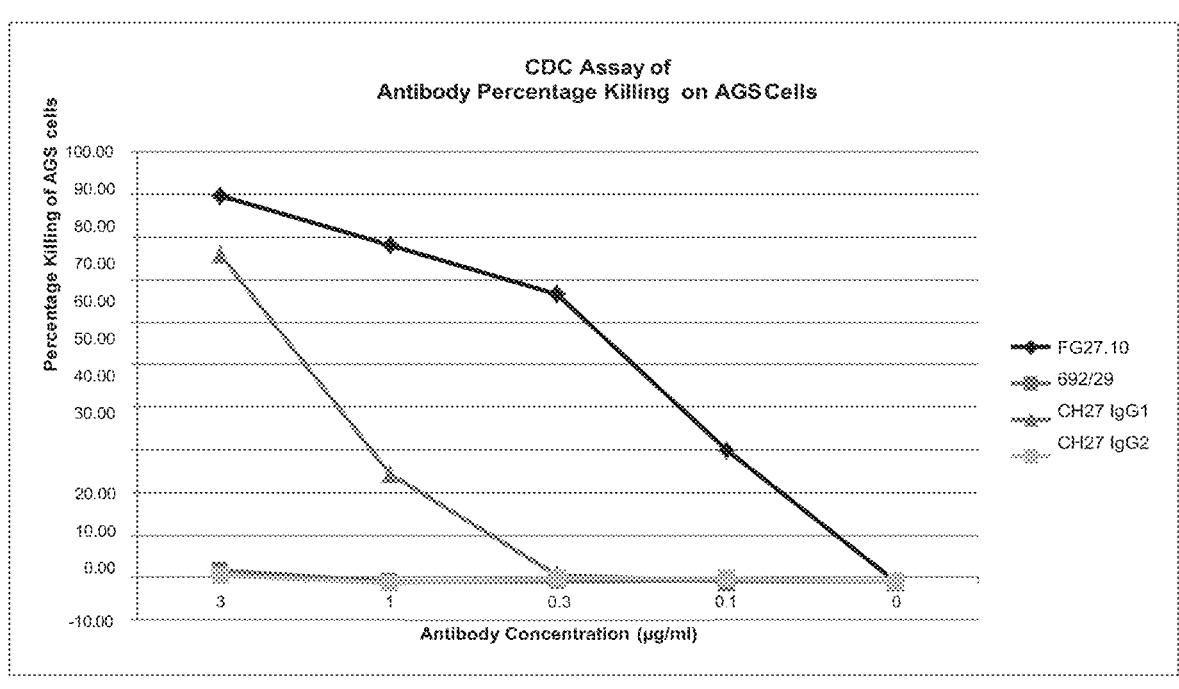

FIG. 17a: Example of FG27.10 mIgG3 mediating ADCC/CDC. Target cells were incubated with PBMCs isolated from human blood (ADCC), or complement (CDC) with either FG27.10 supernatant or irrelevant IgG. Error bars representing standard deviation of triplicate wells are present but may be obscured by data points. FIG. 17b: ADCC of MCF7 tumour cell line on incubation with FG27.10, FG27.18, 692/29, CH27 IgG1 and CH27 IgG2. These are the results from one experiment but are representative of 2 repeats. FIG. 17c: Mean percentage killing by CDC of the ST16 tumour cell line following incubation with FG27.10, FG27.18, 692/29, CH27 IgG1 and CH27 IgG2 with human serum after 4 hrs. Herceptin was included as a control. The assay was performed at serial dilutions 3, 1, 0.3 and 0.1 µg/ml and each dilution was incubated in triplicate. FIG. 17d: Mean percentage killing by CDC of AGS cells following incubation with FG27.10, 692/29, CH27 IgG1 and CH27 IgG2 with human serum after 4 hrs. The assay was performed at serial dilutions 3, 1, 0.3 and 0.1 µg/ml and each dilution was incubated in triplicate.

FIG. 18: FG27 Heavy Chain Gibbs Analysis I: Sequence Identities. Structurally important residues are highlighted: Proline residues are in boxes, Cysteine residues have black dots beneath them, and Asparagine residues are underlined.

FIG. 19: FG27 Heavy Chain Gibbs Analysis II: Identity and Similarity Scores, 4 Å Proximity Residues and CDR Loop Lengths. Cysteine residues are highlighted with a black dot underneath.

Figure 20:
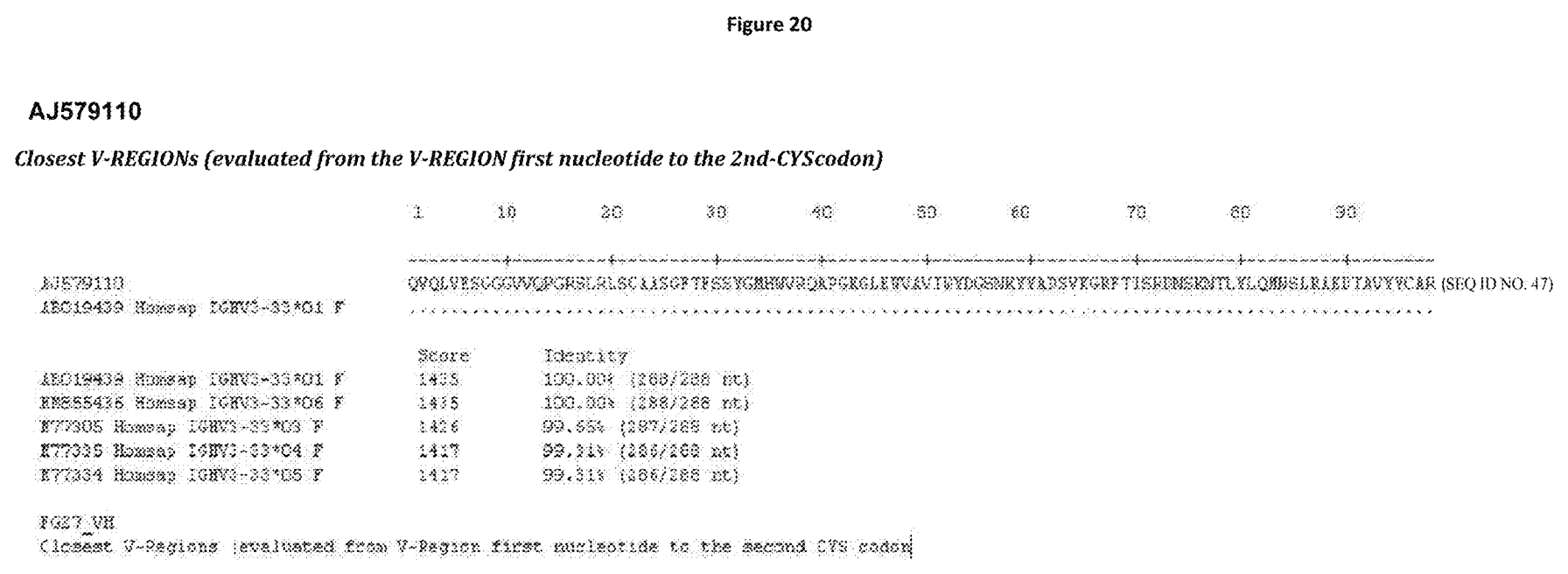

FIG. 20: Human Heavy Chain Donor Sequence Germ Line Analysis.

FIG. 21: FG27 Heavy Chain Humanisation Strategy Structurally important residues are highlighted: Proline residues are outlined in boxes, Cysteine residues have black dots beneath them, and Asparagine residues are underlined with regions in Italics. Residues outlined in bold indicate a back-translation to the mouse residue.

FIG. 22 FG27 Kappa Light Chain Gibbs Analysis I: Sequence Identities. Structurally important residues are highlighted: Proline residues are in boxes, Cysteine residues have black dots beneath them, and Asparagine residues are outlined.

FIG. 23: FG27 Kappa Light Chain Gibbs Analysis II: Identity and Similarity Scores, 4 Å Proximity Residues and CDR Loop Lengths.

FIG. 24: Human Kappa Light Chain Donor Sequence Germ Line Analysis.

FIG. 25 FG27 Kappa Light Chain Humanisation Strategy. Structurally important residues are highlighted: Proline residues are in boxes, and Cysteine residues have black dots beneath them. Residues in Bold indicate back-translations to the mouse residue.

FIG. 26: Comparison of antibody binding to LewisY-HSA antigen for combinations of antibody expressed as LewRHA with LewRKA, LewRKB, LewRKC or LewRKD and LewRHB with LewRKA, LewRKB, LewRKC or LewRKD, including cFG27 positive control antibody and c1210 negative control antibody.

FIG. 27. The thermal stability of LewRHA with LewRKA, LewRKB, LewRKC or LewRKD and LewRHB with LewRKA, LewRKB, LewRKC or LewRKD, including cFG27 positive control antibody.

Figure 28:
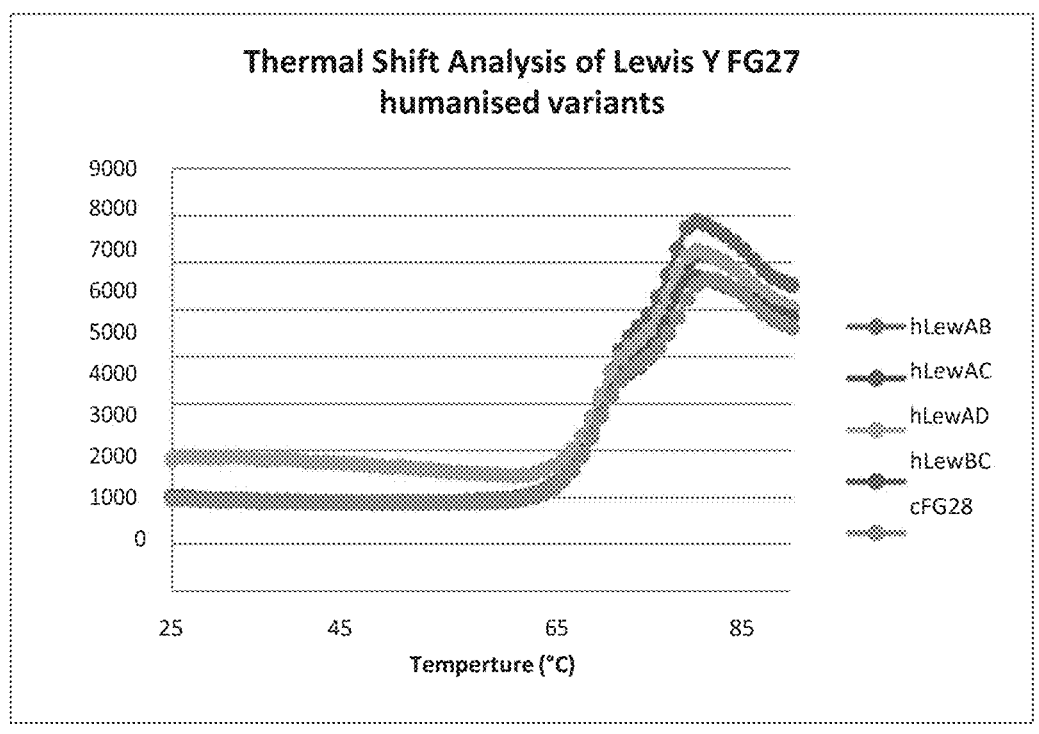

FIG. 28. The thermal shift analysis of Lewis$^y$ FG27 humanised variant hLewAB, hLewAC, hLewAD, hLewBC and control mouse FG27.

Figure 29:
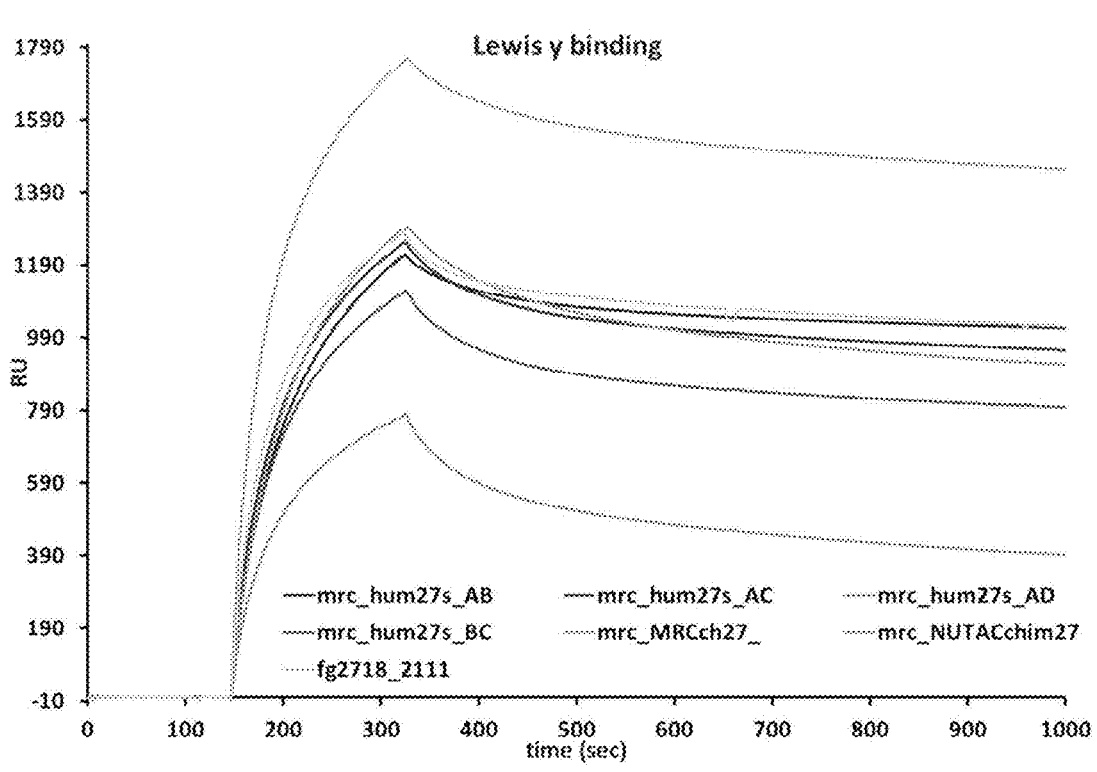

FIG. 29. BiaCore analysis of antibody affinity of FG27 humanised variant hLewAB, hLewAC, hLewAD, hLewBC and control mouse FG27.

Figure 30:
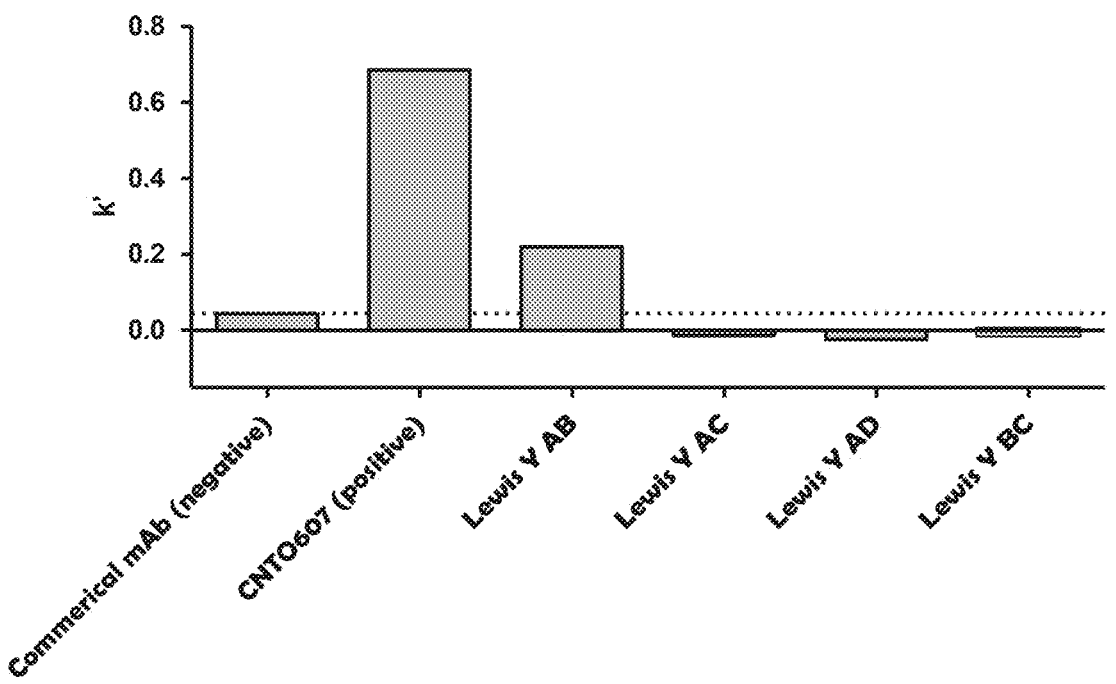

FIG. 30. Non-specific Protein-Protein Interactions (CIC) as measured by Cross-Interaction Chromatography on FG27 humanised variant hLewAB, hLewAC, hLewAD, hLewBC and control mouse FG27.

Figure 31:
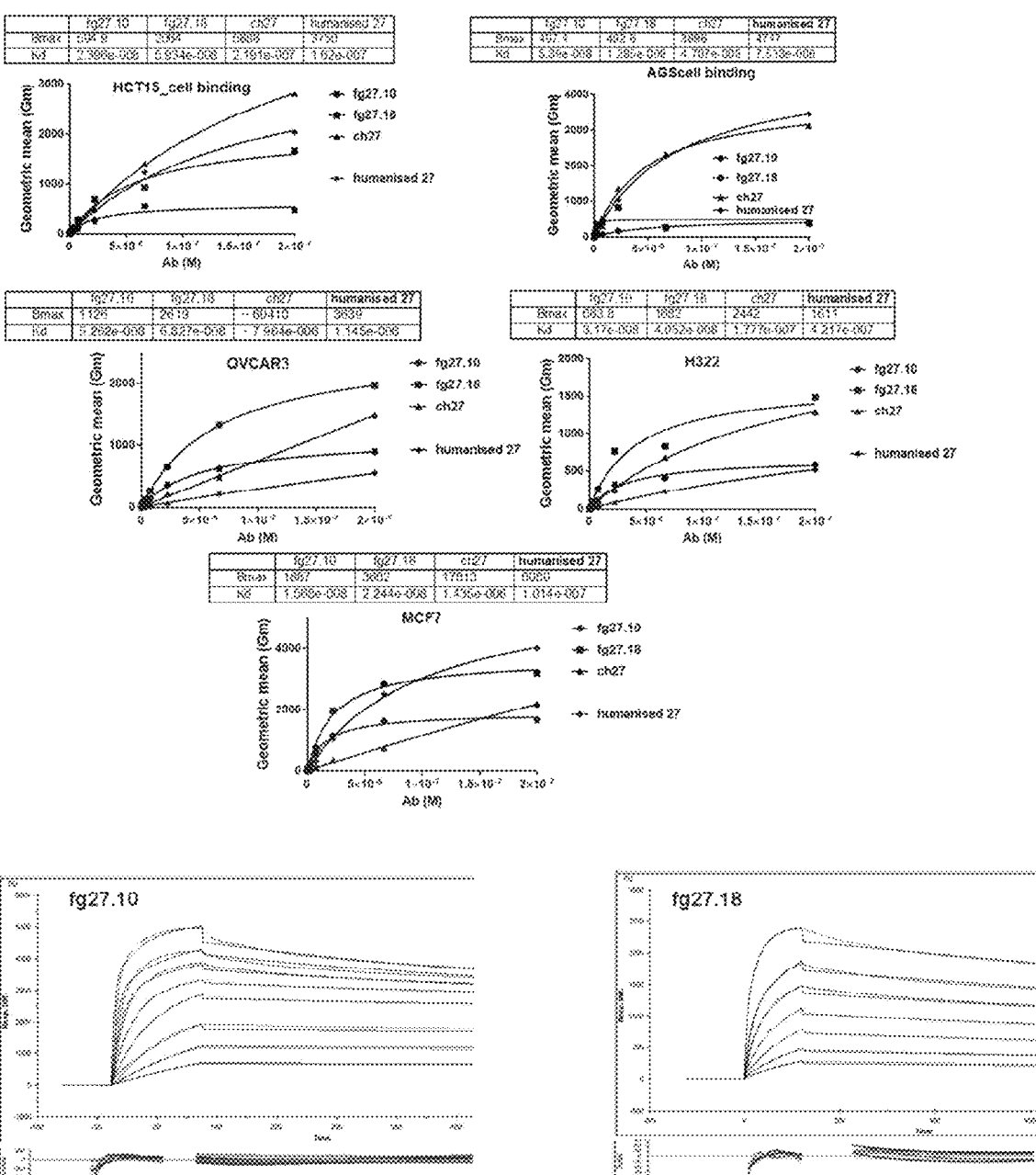

FIG. 31. Binding of FG27.10, FG27.18, ch27IgG1 and humanised variant hLewAC to a panel of cell lines.

Figure 32:
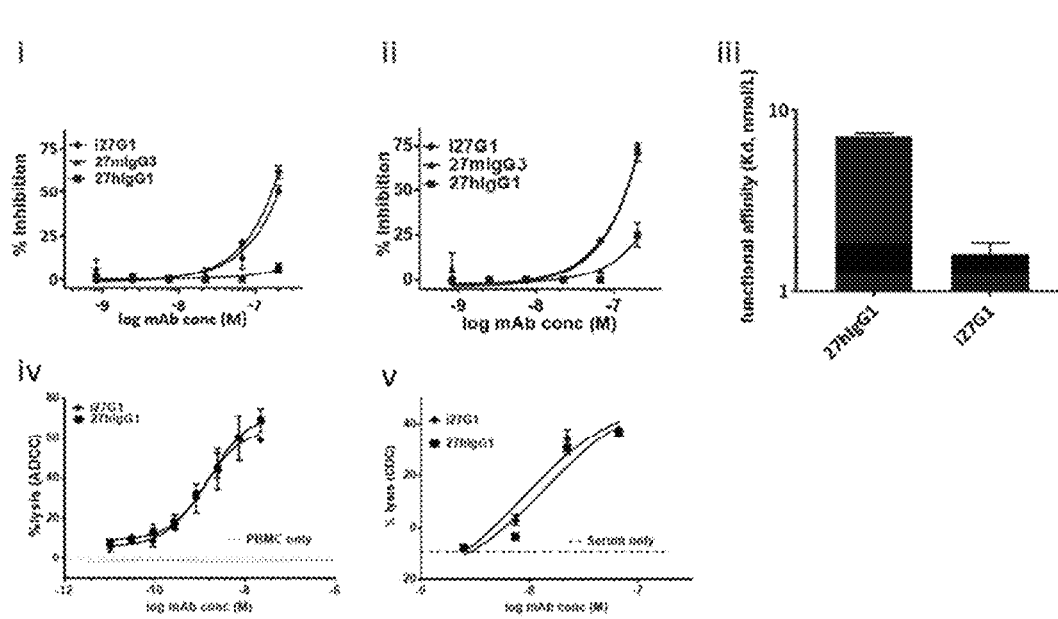

FIG. 32: Significantly increased proliferation inhibition on MCF7 (Panel i) and AGS (Panel ii) by i27G1 compared to 27hIgG1. Significantly increased functional affinity (SPR)

by i27G1 compared to 27hIgG1 (Panel iii). i27G1 maintains equivalent ADCC (Panel iv) as well as CDC activity (panel v) on MCF7. Significance versus parental constructs was deduced from two-way ANOVA (direct cytotoxicity) or one-way ANOVA (functional affinity) with Dunnett's corrections for multiple comparisons.

FIG. 33: Amino acid and nucleic acid sequences of the respective light and heavy chains of the 'i27G1' antibody.

EXAMPLES

Methods

Binding to Tumour Cell Lines:

$1\times10^5$ cancer cells were incubated with 50 µl of primary antibodies at 4° C. for 1 hr. Cells were washed with 200 µl of RPMI 10% new born calf serum (NBCS: Sigma, Poole, UK) and spun at 1,000 rpm for 5 mins. Supernatant was discarded and 50 µl of FITC conjugated anti-mouse IgG Fc specific mAb (Sigma; 1/100 in RPMI 10% NBCS) was used as secondary antibody. Cells were incubated at 4° C. in dark for 1 hr then washed with 200 µl RPMI 10% NBCS and spun at 1,000 rpm for 5 mins. After discarding supernatant, 0.4% formaldehyde was used to fix the cells. Samples were analysed on a Beckman coulter FC-500 flow cytometer (Beckman Coulter, High Wycombe, UK). To analyse and plot raw data, WinMDI 2.9 software was used.

Binding to Blood:

50 µl of healthy donor blood was incubated with 50 µl primary antibody at 4° C. for 1 hr. The blood was washed with 150 µl of RPMI 10% NBCS and spun at 1,000 rpm for 5 mins. Supernatant was discarded and 50 µl FITC conjugated anti-mouse IgG Fc specific mAb (1/100 in RPMI 10% NBCS) was used as the secondary antibody. Cells were incubated at 4° C. in the dark for 1 hr then washed with 150 µl RPMI 10% NBCS and spun at 1,000 rpm for 5 mins. After discarding the supernatant, 50 µl/well Cal-Lyse (Invitrogen, Paisley, UK) was used followed by 500 µl/well distilled water to lyse red blood cells. The blood was subsequently spun at 1,000 rpm for 5 mins. Supernatant was discarded and 0.4% formaldehyde was used to fix the cells. Samples were analysed on a FC-500 flow cytometer (Beckman Coulter). To analyse and plot raw data, WinMDI 2.9 software was used.

Plasma Membrane Glycolipid Extraction:

A cell pellets ($5\times10^7$ cells) were resuspended in 500 µl of Mannitol/HEPES buffer (50 mM Mannitol, 5 mM HEPES, pH7.2, both Sigma) and passed through 3 needles (23G, 25G, 27G) each with 30 pulses. 5 µl of 1M $CaCl_2$) was added to the cells and passed through 3 needles each with 30 pulses as above. Sheared cells were incubated on ice for 20 mins then spun at 3,000g for 15 mins at room temperature (RT). Supernatant was collected and spun at 48,000g for 30 mins at 4° C. and the supernatant was discarded. The pellet was resuspended in 1 ml methanol followed by 1 ml chloroform and incubated with rolling for 30 mins at RT. The sample was then spun at 1,200g for 10 mins to remove precipitated protein. The supernatant, containing plasma membrane glycolipids, was collected and stored at −20° C.

Glycome analysis: To clarify the fine specificities of the FG27 mAbs, the antibodies were FITC labelled and sent to the Consortium for Functional Glycomics functionalglycomics.org/static/consortium/resources/resourcecoreh8.shtml) where they were screened against ≥600 natural and synthetic glycans. Briefly, synthetic and mammalian glycans with amino linkers were printed onto N-hydroxysuccinimide (NHS)-activated glass microscope slides, forming amide linkages. This work was done by Core H of the CFG at Emory University. FG27 was tested at 1 µg/ml in PBS at room temperature. Briefly, antibody samples were applied to the printed surface of the microarray and incubated in a humidified chamber for 1 h. The slide was then rinsed 4 times with PBS, followed by addition of fluorescently labeled (Alexa Fluor 488) anti-rabbit IgG, and was incubated for 1 h. The slide was then rinsed 4 times in PBS, and fluorescence was measured with a PERKIN-ELMER® microarray XL4000 scanner and analyzed using Imagene software (BioDiscovery).

Further details of the protocol used is set out below.

Glycan Binding Assay with Unlabelled Monoclonal Antibody

1. Introduction:
   1.1. Core H primary objective is to determine the binding specificity of Glycan Binding Proteins (GBPs) and various organisms submitted by investigators using the printed glycan microarray.
2. Reference:
   2.1. www.functionalglycomics.org
3. Materials needed:
   3.1. Glycan printed slides (Core D), printed on the side of the slide with the white etched bar code and black marks—DO NOT TOUCH THIS AREA
   3.2. Cover slips (Fisher scientific, 12-545F)
   3.3. Humidified Slide processing chambers (Fisher scientific, NC9091416), or homemade system using Petri Dish, with wet paper towels in the bottom of the chamber
   3.4. 100 ml Coplin jars for washing slides
   3.5. Tris-HCl (Fisher scientific, BP152-1)
   3.6. NaCl (Fisher scientific, S271-3)
   3.7. CaCl2 (Fisher scientific, C79-500)
   3.8. MgCl2 (Fisher scientific, BP214-500)
   3.9. Potassium Phosphate Monobasic (Fisher scientific, P285-3)
   3.10. dH20
   3.11. Cyanine 5-Streptavidin (ZYMED 43-4316)
   3.12. Appropriate secondary antibody, fluorescently labeled if available
   3.13. BSA (Fisher scientific, Bp1600-100)
   3.14. Tween-20 (EMD Biosciences, 655205)
   3.15. Sodium Azide (fisher scientific, S227-500)
   3.16. ProScanArray Scanner (Perkin Elmer)
4. Buffers:
   4.1. TSM=20 mM Tris-HCl, pH 7.4 150 mM NaCl, 2 mM CaCl2, 2 mM MgCl2
   4.2. TSM Wash Buffer (TSMW)=TSM Buffer+0.05% Tween-20
   4.3. TSM Binding Buffer (TSMBB)=TSM buffer+0.05% Tween 20+1% BSA
5. Protocol:
   5.1. Make working stocks of washing buffers (TSM, TSM Wash Buffer, and H2O) or collect reagents and bring to room temperature if they have been in the refrigerator.
   5.1.1. Buffer (A) TSM-20 mM Tris-HCl, pH 7.4 150 mM NaCl, 2 mM CaCl2, 2 mM MgCl2
   5.1.2. Buffer (B) TSM Wash Buffer (TSMW)-TSM Buffer+0.05% Tween-20
   5.1.3. Buffer (C) TSM Binding Buffer (TSMBB)-TSM buffer+0.05% Tween 20+1% BSA
   5.1.4. dH2O
   5.2. Prepare 100 µl of sample by diluting antibody in TSMBB or appropriate Binding Buffer based on properties of Antibody to a final concentration of 5-50 µg/ml or an appropriate concentration required for the analysis.

5.3. Remove slide(s) from desiccator and label slide with sample name near barcode, outside of the black marks.
   5.4. Hydrate the slide by placing in a glass Coplin staining jar containing 100 ml of TSMW for 5 min.
   5.5. Remove excess liquid from slide by setting the slide upright to drain the liquid off.
   5.6. Carefully apply 70 µl of sample (see 5.2) close to the left edge slide in between the black marks.
   5.7. Slowly place cover slip on slide, trying to avoid the formation of bubbles in the sample under the cover slip. Remove any bubbles by gently tapping the cover slip with a pipette tip if necessary, or slowly lifting one side of the cover slip. Make sure the cover slip is between the black marks.

SDS-PAGE and Western Blot Analysis:

Briefly, $10^5$ or $10^6$ cell equivalents (cell lysate, plasma membrane lipid extract) were analysed for FG27 binding. Tumour cell plasma membrane lipid extracts and cell lysates were reduced with dithiothreitol (DTT; Pierce Biotechnology, ThermoFisher, Loughborough, UK) and subjected to SDS-PAGE using NOVEX 4% to 12% Bis-Tris gels (Invitrogen), and transferred to Hybond-P PVDF membranes (GE Healthcare, Amersham, UK) using 1× transfer buffer (20×, Invitrogen) and 20% (v/v) methanol at 30V for 1 hr. Membranes were blocked with 5% (w/v) non-fat dry milk in 0.05% (v/v) Tween-PBS for 1 hr then probed with primary antibodies diluted in Tween-PBS, 2% BSA for 1 hr. Primary antibody binding was detected using biotin-conjugated anti-mouse IgG Fc specific secondary antibody (Sigma; 1/2000 dilution in Tween-PBS, 2% BSA) for 1 hr, and visualised using IRDye 800CW streptavidin (LICOR Biosciences, UK; 1/1000 in Tween-PBS 2% BSA).

Immunohistochemistry Assessment for FG27:

To determine the therapeutic value of FG27, it was screened on gastric, colorectal, ovarian and breast tumour tissue microarrays by immunohistochemistry (IHC).

Methodology: Immunohistochemistry was performed using the standard avidin-biotin peroxidise method. Paraffin embedded tissue sections were placed on a 60° C. hot block to melt the paraffin. Tissue sections were deparaffinised with xylene and rehydrated through graded alcohol. The sections were then immersed in 500 ml of citrate buffer (pH6) and heated for 20 mins in a microwave (Whirlpool) to retrieve antigens. Endogenous peroxidase activity was blocked by incubating the tissue sections with endogenous peroxidase solution (Dako Ltd, Ely, UK) for 5 mins. Normal swine serum (NSS; Vector Labs, CA, USA; 1/50 PBS) was added to each section for 20 mins to block non-specific primary antibody binding. All sections were incubated with Avidin D/Biotin blocking kit (Vector Lab) for 15 mins each in order to block non-specific binding of avidin and biotin. The sections were re-blocked with NSS (1/50 PBS) for 5 mins. Then tissue sections were incubated with primary antibody at RT for an hr. Anti-beta-2-microglobulin (Dako Ltd; 1/100 in PBS) mAb and PBS alone were used as positive and negative controls respectively. Tissue sections were washed with PBS and incubated with biotinylated goat anti-mouse/rabbit immunoglobulin (Vector Labs; 1/50 in NSS) for 30 mins at RT. Tissue sections were washed with PBS and incubated with preformed 1/50 (PBS) streptavidin-biotin/horseradish peroxidase complex (Dako Ltd) for 30 mins at RT. 3, 3'-Diaminobenzidine tetra hydrochloride (DAB) was used as a substrate. Each section was incubated twice with 100 µl of DAB solution for 5 mins. Finally, sections were lightly counterstained with haematoxylin (Sigma-Aldrich, Poole Dorset, UK) before dehydrating in graded alcohols, cleaning by immersing in xylene and mounting the slides with Distyrene, plasticiser, xylene (DPX) mountant (Sigma). Identification of FG27.10 and FG27.18 Heavy and Light Chain Variable Regions Cell Source and Total RNA Preparation:

Approximately $5 \times 10^6$ cells from hybridomas FG27.10 and FG27.18 were taken from tissue culture, washed once in PBS, and the cell pellet treated with 500 µl Trizol (Invitrogen). After the cells had been dispersed in the reagent, they were stored at −80° C. until RNA was prepared following manufacturer's protocol. RNA concentration and purity were determined by Nanodrop. Prior to cDNA synthesis, RNA was DNase I treated to remove genomic DNA contamination (DNase I recombinant, RNase-free, Roche Diagnostics, Burgess Hill, UK) following manufacturer's recommendations.

cDNA Synthesis:

First-strand cDNA was prepared from 3 µg of total RNA using a first-strand cDNA synthesis kit and AMV reverse transcriptase following manufacturer's protocol (Roche Diagnostics). After cDNA synthesis, reverse transcriptase activity was destroyed by incubation at 90° C. for 10 mins and cDNA stored at −20° C.

GAPDH PCR to Assess cDNA Quality:

A PCR was used to assess cDNA quality; primers specific for the mouse GAPDH house-keeping gene (5'-TTAGCACCCCTGGCCAAGG-3' (SEQ ID NO: 61) and 5'-CTTACTCCCTTGGAGGCCATG-3') (SEQ ID NO: 62) were used with a hot-start Taq polymerase (NEB, Hitchen, UK) for 35 cycles (95° C., 3 mins followed by 35 cycles of 94° C./30 secs, 55° C./30 secs, 72° C./1 min; final polishing step of 10 mins at 72° C.). Amplified products were assessed by agarose gel electrophoresis.

PCR Primer Design for Cloning FG27 Variable Regions:

Primers were designed to amplify the heavy and light chain variable regions based upon the PCR product sequence data. Primers were designed to allow cloning of the relevant chain into unique restriction enzyme sites in the hIgG1/kappa double expression vector pDCOrig-hIgG1. Each 5' primer was targeted to the starting codon and leader peptide of the defined variable region, with a Kozak consensus immediately 5' of the starting codon. Each 3'primer was designed to be complementary to the joining region of the antibody sequence, to maintain reading frame after cloning of the chain, and to preserve the amino acid sequence usually found at the joining region/constant region junction. All primers were purchased from Eurofins MWG.

Heavy Chain Variable Region PCR:

Immunoglobulin heavy chain variable region usage was determined using PCR with a previously published set of primers (Jones and Bendig 1991). Previous results using a mouse mAb isotyping test kit (Serotec, Oxford, UK) had indicated that FG27.10 was a mouse IgG3 and FG27.18 a mouse IgG1 antibody. Appropriate constant region reverse primers were therefore used to amplify from the constant regions. PCR amplification was carried out with 12 mouse VH region-specific 5' primers and 3' primers specific for previously determined antibody subclass with a hot-start Taq polymerase for 35 cycles (94° C., 5 mins followed by 35 cycles of 94° C./1 min, 60° C./1 min, 72° C./2 mins; final polishing step of 20 mins at 72° C.). Amplified products were assessed by agarose gel electrophoresis. Positive amplifications resulted for the VH4 primer.

Light (κ) Chain Variable Region PCRs:

Immunoglobulin light chain variable region usage was determined using PCR with a previously published set of primers (Jones and Bendig 1991). Previous results using a mouse mAb isotyping test kit had indicated that both FG27.10 and FG27.18 used κ light chains. PCR amplification was carried out with mouse Vκ region-specific 5' and 3' mouse Cκ specific primers with a hot-start Taq polymerase for 35 cycles (94° C., 5 mins followed by 35 cycles of 94° C./1 min, 60° C./1 min, 72° C./2 mins; final polishing step of 20 mins at 72° C.). Amplification products were assessed by agarose gel electrophoresis. Positive amplifications resulted with the Vκ1 and Vκ2 primers for both FG27.10 and FG27.18.

PCR Product Purification and Sequencing:

PCR products were purified using a Qiaquick PCR purification kit (Qiagen, Crawley, UK). The concentration of the resulting DNA was determined by Nanodrop and the purity assessed by agarose gel electrophoresis. PCR products were sequenced using the originating 5' and 3' PCR primers at the University of Nottingham DNA sequencing facility (http://www.nottingham.ac.uk/life-sciences/facilities/dna.se-quecncing/index.aspx). Sequences were analysed (V region identification, junction analysis) using the IMGT database search facility (http://www.imgt.org/IMGT.vquest/vquest?llvret=0&Option=mouseIg). Sequencing indicated that FG27.10 and FG27.18 shared identical heavy and light chain variable regions. Sufficient residual constant region was present in the heavy chain sequences to confirm that FG27.10 was of the mIgG3 subclass and FG27.18 a mIgG1 with the two having resulted from a single splenocyte-NSO fusion event.

Cloning Strategy:

Direct cloning of the PCR products into the pDCOrig-hIgG1 vector using the restriction sites incorporated into the PCR primers was known to be relatively inefficient from previous Scancell experience. A dual cloning strategy was therefore adopted; the PCR product generated using a proof-reading polymerase was cloned into both pDCOrig-hIgG1 and a TA vector (pCR2.1; Invitrogen) simultaneously, with the TA vector-cloned product acting as an easily expanded backup source of material for cloning should the initial pDCOrig-hIgG1 cloning fail.

FG27.18 Heavy/Light Chain PCR for Cloning:

PCR amplification was carried out using a proof-reading polymerase (Phusion; NEB) and the cloning primers described above using the FG27.18 cDNA template previously described for 35 cycles (98° C., 3 mins followed by 35 cycles of 98° C./30 secs, 58° C./30 secs, 72° C./45 secs; final polishing step of 3 mins at 72° C.). Successful amplification was confirmed by agarose gel electrophoresis.

Method 1—Direct light chain cloning: Amplified FG27.18 light chain was digested sequentially with the restriction enzymes BsiWI and BamHI according to manufacturer's instructions (NEB). Vector (pDCOrig-hIgG1, containing V regions from a previously cloned antibody) was simultaneously digested. Vector DNA was agarose gel purified using a QIAquick gel extraction kit (Qiagen) and insert DNA purified using a PCR purification kit. After DNA quantification by Nanodrop, vector DNA was phosphatase treated according to manufacturer's recommendations (Antarctic Phosphatase, NEB) and light chain insert ligated into the vector (T4 DNA ligase, NEB). Ligated DNA was transformed into chemically competent TOP10F' cells (Invitrogen) and spread on 35 µg/ml Zeocin (Invitrogen, Toulouse, France) supplemented LB agar plates which were then incubated overnight at 37° C.

Method 2—TOPO light chain cloning: Amplified FG27.18 light chain was treated with Taq polymerase (NEB) for 15 mins at 72° C. to add 'A' overhangs compatible with TA cloning. Treated PCR product was incubated with the TOPO TA vector pCR2.1 (Invitrogen) and transformed into chemically competent TOP10F' cells according to manufacturer's instructions. Transformed bacteria were spread on ampicillin (80 µg/ml) supplemented LB agar plates which were then incubated overnight at 37° C. Colonies were grown in liquid culture (LB supplemented with 80 µg/ml ampicillin) and plasmid DNA prepared (spin miniprep kit, Qiagen). Presence of an insert was confirmed by sequential digestion with BsiWI and BamHI and agarose gel electrophoresis. Sequencing was carried out on miniprep DNA from colonies using T7 and M13rev primers. The DNA insert from one such colony had the predicted FG27.18 light chain sequence; a 300 ml bacterial LB/ampicillin culture was grown overnight and plasmid DNA prepared by maxiprep (plasmid maxi kit, Qiagen). Maxiprep DNA insert was confirmed by sequencing.

TOPO Heavy Chain Cloning:

Amplified FG27.18 heavy chain was treated with Taq polymerase (NEB) for 15 mins at 72° C. to add 'A' overhangs. Treated PCR product was incubated with the TOPO TA vector pCR2.1 and transformed into chemically competent TOP10F' cells as above. Transformed bacteria were spread on ampicillin supplemented LB agar plates which were then incubated overnight at 37° C. Colonies were grown in liquid culture (LB/ampicillin) and plasmid DNA prepared (spin miniprep kit). Presence of an insert was confirmed by digestion with HindII and AfeI and agarose gel electrophoresis. Sequencing was carried out on miniprep DNA from a number of colonies using T7 and M13rev primers. The DNA insert from one such colony had the predicted FG27.18 heavy chain sequence; a 300 ml bacterial LB/ampicillin culture was grown overnight and plasmid DNA prepared by maxiprep (plasmid maxi kit, Qiagen). Maxiprep DNA insert was confirmed by sequencing.

pDCOrig-hIgG1 Double Expression Vector Light Chain Cloning:

The FG27.18 light chain was digested from the TOPO vector pCR2.1 by sequential digestion with BsiWI and BamHI and the 400 bp insert DNA agarose gel purified using a QIAquick gel extraction kit (Qiagen) following manufacturer's recommendations. This insert was ligated into previously prepared pDCOrig-hIgG1 vector (see above) and transformed into chemically competent TOP10F' cells. Transformations were spread on 35 µg/ml Zeocin supplemented LB agar plates which were then incubated overnight at 37° C.

Colonies were grown in liquid culture (LB supplemented with 35 µg/ml Zeocin) and plasmid DNA prepared (spin miniprep kit, Qiagen). Sequencing was carried out on miniprep DNA from all colonies using the P6 sequencing primer sited in the human kappa constant region. The DNA insert from a colony had the predicted FG27.18 light chain sequence correctly inserted in pDCOrig-hIgG1; a 300 ml bacterial LB/zeocin culture was grown overnight and plasmid DNA prepared by maxiprep (plasmid maxi kit, Qiagen).

pDCOrig-higG1 Double Expression Vector Heavy Chain Cloning:

The FG27.18 heavy chain insert was digested from the TOPO vector pCR2.1 by digestion with HindIII and AfeI. Vector (pDCOrig-hIgG1-27.18k) containing the FG27.18 kappa light chain (prepared above) was also digested with HindIII and AfeI. The vector DNA was then phosphatase treated according to manufacturer's recommendations (Antarctic Phosphatase, NEB). After agarose gel electrophoresis, the 6.5 kb pDCOrig-hIgG1 vector band and 400 bp FG27.18H insert band were isolated using a QIAquick gel extraction kit (Qiagen) following manufacturer's recommendations. The insert was ligated into the pDCOrig-hIgG1 vector and transformed into chemically competent TOP10F' cells. Transformations were spread on 35 µg/ml Zeocin supplemented LB agar plates which were then incubated overnight at 37° C. Colonies were grown in liquid culture (LB supplemented with 35 µg/ml Zeocin) and plasmid DNA prepared (spin miniprep kit, Qiagen). Presence of an insert was confirmed by digestion with HindIII and AfeI and agarose gel electrophoresis. Sequencing was carried out on miniprep DNA from a number of the colonies using the P3rev sequencing primer sited in the human IgG1 constant region. The DNA insert from one of the colonies had the predicted FG27.18 heavy chain sequence correctly inserted in pDCOrig-hIgG1; a 300 ml bacterial LB/zeocin culture was grown overnight and plasmid DNA prepared by maxiprep (plasmid maxi kit, Qiagen). Sequencing was used to confirm that both heavy and light chain loci.

Expression, Purification and Characterisation of the Chimeric Antibody Constructs:

The methodology for the expression and purification of chimeric antibody described in the present invention can be achieved using methods well known in the art. Briefly, antibodies can be purified from supernatant collected from transiently, or subsequently stable, transfected cells by protein A or protein G affinity chromatography based on standard protocols, for example Sambrook et al., 2001 (Sambrook and Russell 2001).

QuikChange Lightning Site-Directed Mutagenesis Kit (Stratagene)

Prepare the reaction(s) as indicated below:

5 µl of 10× reaction buffer 0.12 µl (25 ng) of RHA or RKA template 1.3 µl (125 ng) of oligonucleotide mutation primer For 1.3 µl (125 ng) of oligonucleotide mutation primer Rev 1 µl of dNTPmix 1.5 µl of QuikSolution reagent ddH₂O to a final volume of 50 µl 1 µl of QuikChange Lightning Enzyme 1. Cycle each reaction using the cycling parameters outlined in the following table:

| | 3-step protocol | | |
| --- | --- | --- | --- |
| Cycle step | Time | Temp. | Cycles |
| Initial denaturation | 95° C. | 2 mins | 1 |
| Denaturation Temp. | 95° C. | 20 secs | 18 |
| Annealing Extension | 60° C. | 10 secs | |
| | 68° C. | 3 mins | |
| Final extension | 68° C. | 5 mins | 1 |
| | 4° C. | hold | |

2. Add 2 µl of the Dpn I restriction enzyme

3. Gently and thoroughly mix each reaction, microcentrifuge briefly, then immediately incubate at 37° C. for 5 mins to digest the parental dsDNA 4. Transform 2 µl of the Dpn I-treated DNA from each reaction into separate 45 µl (+2 µl β-ME) aliquots of XL10-Gold ultracompetent cells (see Transformation of TOP10™ E. coli).

5. Screen colonies using the Phusion method, miniprep and sequence to check for the correct mutation.

Q5® Site-Directed Mutagenesis Kit (NEB Protocol):

1. Assemble the following reagents in a thin-walled PCR tube:

| Reagent | Volume for 25 μl final reaction volume) |
|---|---|
| Q5 Hot Start High-Fidelity 2 × Master Mix | 12.5 μl |
| 10 μM Forward Primer | 1.25 μl |
| 10 μM Reverse Primer | 1.25 μl |
| Template DNA (1-25ng/μl) | 1 μl |
| Nuclease-free water | 9 μl |

Cycle

| | 3-step protocol | | |
|---|---|---|---|
| Cycle step | Time | Temp. | Cycles |
| Initial denaturation | 98° C. | 30 secs | 1 |
| Denaturation Temp. | 98° C. | 10 secs | 25 |
| Annealing Extension | 69° C. | 30 secs | |
| | 72° C. | 180 secs | |
| Final extension | 72° C. | 2 mins | 1 |
| | 4° C. | hold | |

Kinase, Ligase & DpnI (KLD) Treatment
  2. Add the following reagents and incubate for 5 mins at
     RT: 1 μl of PCR product
  5 μl 2×KLD Reaction Buffer 1 μl 10×KLD Enzyme Mix
  3 μl Nuclease-free Water
  3. Transform 5 μl of the KDL mix from each reaction into
     separate 50 μl of NEB 5-alpha Competent *E. coli*
     Carefully flick the tube 4-5 times to mix. Do not vortex.
  4. Place the mixture on ice for 30 mins.
  5. Heat shock at 42° C. for 30 secs. Place on ice for 5
     mins.
  6. Pipette 950 μl of RT SOC into the mixture.
  7. Incubate at 37° C. for 60 mins with shaking (250 rpm).
  8. Mix the cells thoroughly by flicking the tube and
     inverting, then spread 50 μl onto a kanamycin plate and
     incubate overnight at 37° C.
  9. Screen colonies using the GoTaq Green method, mini-
     prep and sequence to check for the correct mutation.
IgG Quantification:
  Coat each well of a 96-well immunoplate with 100 μl
aliquots of 0.4 μg/ml goat anti-human IgG antibody, diluted
in PBS, incubate overnight at 4° C. (Plates may be stored for
1 month at this stage). Also coat another blank plate with
BSA/PBS blocking solution. Remove the excess coating
solutions and wash the plate three times with 200 μl/well of
washing buffer. Into the blank plate, dispense 120 μl of SEC
buffer into all wells except the wells in column 2, rows B to
G. Prepare a 1 μg/ml solution of the human IgG1/kappa
antibody in SEC buffer to serve as a standard. Pipette 240
μl/well into the wells in column 2, rows B and C. Centrifuge
the medium from transfected cells (250g, 5 mins) and save
the supernatant. Pipette 240 μl of the supernatant from the
"no DNA" control (where cos cells were transfected in the
absence of DNA) into the well in column 2, row D. Pipette
240 μl/well of experimental supernatants into the wells in
column 2, rows E, F, and G. Mix the 240 μl aliquots in the
wells of column 2, rows B to G, and then transfer 120 μl to
the neighbouring wells in column 3. Continue to column 11
with a series of 2-fold dilutions of the standard, control, and
experimental samples. Transfer 100 μl from each well to the
corresponding well of the anti-IgG-coated plate. Incubate at
37° C. for 1 hr. Rinse all the wells 3× with washing buffer
(200 μl). Dilute the goat anti-human kappa light chain
peroxidase conjugate 5000-fold in SEC buffer and add 100
μl to each well. Repeat the incubation and washing steps (step 9). Add 150 μl of K-BLUE substrate to each well,
incubate in the dark at RT for 10 mins. Stop the reaction by
adding 50 μl of RED STOP solution to each well. Read the
optical density at 655 nm.
Lewis$^y$ Binding ELISA
  Coat each well of a 94-well MaxiSorp plate (Nunc) with
100 ng/well of Lewis Y HSA peptide in PBS and incubate
overnight at 4° C. Wash 3× with PBS-T (0.1% Tween20).
Block a fresh plate with 250 μl of PBS/0.2% BSA/0.05%
Tween20 per well and incubate for 1 hr at RT. Wash 3× with
PBS-T. Add 240 μl of antibody (diluted in PBS/0.2% BSA/
0.05% Tween20 if necessary) to wells in column 1; 120 μl
of buffer (PBS/0.2% BSA/0.05% Tween20) in the other
wells. Transfer 120 μl from column 1 to the neighbouring
wells in column 2. Continue to column 12 with a series of
2-fold dilutions of the experimental samples. Transfer 100 μl
per well from the dilution plate to the experimental plate.
Incubate for 1 hr at RT. Wash wells 3× with PBS-T. Dilute
the goat anti-human Fc peroxidase conjugate 10000-fold (or
anti-mouse at 10000-fold dilution) in PBS/0.2% BSA/0.05%
Tween20 and add 100 μl to each well. Incubate 1 hr at RT
and repeat washing step. Add 150 μl of substrate (K-Blue)
per well and incubate for 150 mins at RT. Stop the reaction
by adding 50 μl of RED STOP solution to each well. Read
the optical density at 650 nm.
Thermal Stability
  Dilute fully humanised antibodies and the chimeric con-
trol to 1 μg/ml in TBS/0.2% Tween and aliquot at the
appropriate volume for the EC80 concentration into PCR
tubes. Bring the volume up to 100 μl with the same buffer.
Heat separately each tube for 10 mins at temperatures
between 30° C. and 85° C. with a 5° C. interval and cool to
4° C. Freeze down the 1 μg/ml stock for 1 hr and then dilute
to the EC80 concentration. Perform the binding assay
against Lewis Y HSA peptide using 100 μl of each antibody
per well (assay each temperature in duplicate) in a 96-well
plate.
Thermal Shift Comparison
  Prepare samples directly into 96 well white PCR plate in
a final volume of 25 μl (purified antibody final concentration
of 1 and 2 μM. Sypro Orange-make stock 1:100 in PBS
buffer, then add 1:10 to final samples (e.g. 2.5 μl in 25 μl).
Load into the qPCR machine an use the MxPro software,
SYBR Green method, (filter=FRROX, no reference dye).
Thermal profile setup—71 cycles of 1° increase. Plot the
results and determine Tm.
Purification of Humanised mab
  Instrument: GE Healthcare ÄKTAxpress™ Purification
    System
  Software: UNICORN
  Columns: HiTrap MabSelect SuRe, 1 ml; HiLoad 16/600
    Superdex 200pg
  Mobile phase: IgG Elution Buffer; Dulbecco's 1×PBS
  Sample prep: Filtering through 0.22 μm
  Injection volume: 200 ml Expi293 conditioned medium
    (1:1) in DPBS
  Flow rate: Sample loading at 0.5 ml/min; Gel filtration at
    1.5 ml/min; Elution at 1 ml/min
Aggregation Comparison
  Instruments: Agilent 1260 infinity HPLC system with
    thermostatted column compartment, Wyatt Technology
    Dawn Heleos, Wyatt Technology Optilab TRex
  Analysis software: Wyatt Technology Astra version
    6.1.1.17
  Column: Acquity UPLC BEH200 SEC, 4.6×150 mm, 1.7
    μm Mobile phase: Dulbecco's 1×PBS with 0.05% sodium azide Sample prep: Filtering through PES 0.22 µm Sample concentration: Varying Injection volume: 20 µl Analysis temperature: 30° C.

Flow rate: 0.4 ml/min

Cross-Interaction Chromatography (CIC)

Cross-interaction chromatography (CIC) analysis was carried out to assess proneness to non-specific protein-protein interactions and provide an indication of any solubility issues, which can give rise to downstream manufacturing problems.

Samples were analyzed by two separate 20 µl injections (0.5 mg/ml); firstly onto a 1 ml NHS activated resin (GE Healthcare) coupled with 30 mg human polyclonal IgG (Sigma 14506) and secondly onto a 1 ml NHS activated resin blank coupled, as control column. The mobile phase consisted of Dulbecco's PBS (Sigma D8537) containing 0.01% sodium azide (0.1 ml/min) and all experiments were performed at 25° C. Eluted samples were detected by UV absorbance (Agilent 1260 Infinity HPLC system with thermostatted column compartment) and data was analysed using Wyatt Technology ASTRA software (version 6.1.2.83) to determine sample peak retention times. These were then used to calculate a retention factor k':

$$k' = \frac{(Tr - Tm)}{Tm}$$

where Tr is the retention time of the sample on the poly-IgG column and Tm is the retention time on the mock (control) column.

Surface Plasmon Resonance (SPR):

Lewis Y HSA conjugate was coupled to a CM5 chip and the FG27.10 and FG27.18 mAbs (concentration range 0.01 µM-1 µM) injected at 30 µl/min. Binding data were fitted to a heterogenous ligand model using the BIA evaluation software.

Antibody Internalisation:

Cancer cells were plated at a density of $2 \times 10^3$ cells/well and left to adhere overnight. Cells were cultured at 37° C. for 72 hrs in 96-well plates and treated with the indicated concentration of mAb in combination with secondary antibody: saporin-conjugated goat antibody (F' ab fragment) to mouse (ATSbio, IT #48) or human IgG. Control wells consisted of cells incubated with culture medium only and with secondary conjugate only. The amount of secondary antibody per well was 75 ng and primary antibody concentration was varied from 0.01 nM to 30 nM. Saporin internalisation was assessed via inhibition of thymidine uptake (thymidine was added for the last 24 hrs of the incubation).

ADCC and CDC:

Cells ($5 \times 10^3$) were co-incubated with 100 µl of PBMCs, 10% autologous serum or media alone or with mAbs at a range of concentrations. Spontaneous and maximum releases were evaluated by incubating the labeled cells with medium alone or with 10% Triton X-100, respectively. After 4 hrs of incubation, 50 µl of supernatant from each well was transferred to 96 well lumaplates. Plates were allow to dry overnight and counted on a Topcount NXT counter (Perkin Elmer, Cambridge, UK). The mean percentage lysis of target cells was calculated according to the following formula:

Mean % lysis =

$$100 \times \frac{\text{mean experimental counts} - \text{mean spontaneous counts}}{\text{mean maximum counts} - \text{mean spontaneous counts}}$$

PI Uptake Assay:

FG27.10 and FG27.18 were incubated with AGS cells and tested for uptake of the small molecular weight dye propidium iodide (PI, Sigma) at various concentrations; the number of PI positive cells representing the number of dying/dead cells. Tumour cells ($5 \times 10^4$) were incubated on a 96-well round bottom microtitre plate with 50 µl of primary antibodies at RT for 2 hrs. 1 µg of PI was added and cells were incubated at RT for 30 mins. Samples were analysed on a FC-500 flow cytometer (Beckman Coulter). To analyse and plot raw data WinMDI 2.9 software was used. For comparison, mAb SC104 which is known to induce membrane damage and 791T/36 were also included as internal controls for the experiment.

Proliferation Inhibition Assay:

Proliferation inhibition by the constructs was assessed by using the water-soluble tetrazolium salt WST-8 (CCK8 kit, Sigma-Aldrich) to measure the activity of cellular hydrogenases which is directly proportional to the number of viable cells. Briefly, after overnight plating of cancer cells (2000 cells/90 µl/well), constructs were added at different concentrations in a final volume of 10 µl/well and the plates were incubated at 37° C., (5% CO2) for 72-96 h. WST-8 reagent was then added (10 µl/well) and after a further 3 h incubation, the plates were read at 450 nm (Tecan Infinite F50) and percentage inhibition calculated. EC50 values were determined using nonlinear regression (curve fit) with GraphPad Prism v 8.0 (GraphPad Inc, La Jolla, CA).

In Vivo Model:

The studies were conducted under a UK Home Office Licence. NCRI guidelines for the welfare and use of animals in cancer research, LASA good practice guidelines and FELAS working group on pain and distress guidelines was also followed. Endotoxin free (<10 EU/ml) FG27 mAb was supplied in pre-formulated aliquots ready for dosing and stored at −20° C. until use. Age matched male MF-1 nude mice were obtained from Harlan Laboratories (Bichester, UK) with each group, FG27, control mAbs or the vehicle control, consisting of n≥8 animals.

Mice were implanted with C170HM2 DLuX cells and monitored by optical imaging to determine tumour establishment and suitability to be entered into the study. Mice were dosed with either FG27 or a positive control mAb (505/4, FG88.2 or FG88.7 (1 mg/ml) as appropriate) at 0.1 mg 2× weekly 100 µl intravenously (i.v.) until termination, or PBS, the vehicle control for the mAb, 100 µl 2× weekly i.v. until termination. Weekly bioluminescent imaging was carried out on all mice to obtain pre and post dosing tumour measurements. In this way each mouse provided pre-dose control readings against which tumour growth could be compared.

All measurements and readouts were transferred from the original dictation/notation to excel (tab delineated) format for data processing in SPSS v16.0. Data integrity was checked using explore and descriptive functions. Erroneous points when identified were cross referenced against the original data and corrected accordingly. The data was screened for outliers and distribution profile; data-points falling outside the 95% confidence limit (outliers) were removed from analysis, but kept in the datasheet for reference purposes.

Mice were imaged weekly for bioluminescent tumour burden (BLI) over the duration of the study as follows; 60 mg/kg D-Luciferin substrate was administered subcutaneously (s.c.), the mice were anesthetised and BLI readings taken 15 mins post substrate administration on open filter block (2D) and sequential emission filters (for DLIT, 3D reconstruction). Ventral and dorsal imaging was undertaken; the optimum position for imaging was abdomen uppermost. BLI was measured over the entire abdominal area, one Region of Interest (ROI) for each mouse in order to include all lesions present. Each mouse had a pre-dosing or baseline image taken to allow calculation of percentage tumour growth over time; these data were averaged per group. BLI readings were also taken after termination to identify tumours in PM tissue.

Example 1—Generation and Initial Characterisation of FG27 mAbs

FG27 was Raised by Immunisation with Gastric Tumour Cell Glycolipid

Analysis of antibody response to immunisations: Antibody titres were initially monitored by lipid enzyme-linked immunosorbent assay (ELISA). Thin layer chromatography (TLC) analysis using ST16 total and plasma membrane lipid extracts, flow cytometry analysis (FACS) using ST16 tumour cells and Western blot using ST16 whole cell extract, total and plasma membrane lipid extracts were subsequently performed. The mouse considered to have the best response, compared to the pre-bleed serum control was boosted intravenously (i.v.) with ST16 plasma membrane lipid extract prior to fusion.

Binding of FG27 hybridoma supernatant to a panel of tumour cell lines was analysed by direct immunofluorescence and FACS analysis. Both FG27.10 and FG27.18 bound ST16 but did not bind human umbilical vein endothelial cells (HUVECs) or peripheral blood mononuclear cells (PBMCs) when compared to positive control anti-HLA mAb, W6/32 (eBioscience, CA, USA), and the negative control (FIG. 4). FG27.10 and FG27.18 were both cloned. FG27.10 was an IgG3κ and FG27.18 was an IgG1κ subclass. To ensure that both mAbs bound to glycolipid, glycolipid was extracted from a range of cell lines, dried onto an ELISA plate before incubating with FG27.10 and FG27.18. Binding was seen with C170, ST16 and AGS derived glycolipid with both mAbs but not cell lines which showed a lack of binding to whole cells (MKN-45, OAW28, OVCAR-3, OVCAR-4 and OAW42; FIG. 5).

Example 2—Defining the Epitopes Recognised by FG27 mAbs

To determine the degree of specificity of FG27.10, the antibody was initially assessed for binding to the HSA-coupled $Le^a$, $Le^b$, $Le^x$ and $Le^y$ antigens by ELISA. FG27.10 failed to recognise $Le^a$, $Le^{a-x}$ or $Le^b$ but strongly recognised $Le^y$ (FIG. 6). To further clarify the fine specificities of the FG27 mAbs, they were screened against ≥600 natural and synthetic glycans by the Consortium for Functional Glycomics. Binding of FG27.10 and FG27.18 mAbs to the glycan array showed that both mAbs bound specifically to $Le^y$ (FIG. 7). For comparison, binding of 692/29 demonstrated the mAb bound most strongly to $Le^b$, glycans containing $Le^b$ and also to tri-$Le^y$ and its variants. In contrast, BR96 was shown to bind $Le^y$ as well as a range of $Le^y$ variants ($Le^{yx}$, $Le^{y-x-x}$) and more weakly to $Le^x$.

FG27.10 and FG27.18 were also screened on a panel of tumour cells lines by SDS/PAGE/Western blot for their ability to recognise glycoproteins as well as glycolipids (FIG. 8). In addition to binding glycolipids, as evidenced by binding at the dye front, both mAbs, also recognised a range of glycoproteins.

As FG27 was $Le^y$ specific, its binding to cell lines (FIG. 9) was compared to mAb BR96, which recognises $Le^y$ and $Le^x$, and mAb 692/29, which recognises $Le^y$ and $Le^b$. All three mAbs bound C170 and AGS cells. In contrast, BR96 bound strongly to Colo201, 692/29 bound moderately whereas FG27 failed to bind (FIG. 9). This shows that this cell line does not express $Le^y$ but probably expresses $Le^x$ and $Le^b$, which could not have been concluded using the non specific mAbs. HT29 cells failed to bind any of the mAbs whereas FG27.10 bound best to OVCAR3 and ST16 and 692/29 to LoVo cells.

Example 3—Immunohistochemistry Assessment for FG27

To assess the binding of FG27 to normal human tissues it was screened on a panel of tissue types. In contrast to mAbs cross reacting with $Le^{y/b}$ (692/29) and $Le^{y/x}$ (BR96), FG27 only bound to subpopulations of cells within normal stomach, lung, tonsil, pancreas and duodenum (Table 1). Further, in contrast to other $Le^y$ cross reactive mAbs, FG27 failed to stain colon, jejunum, breast, kidney or the ileum. Representative IHC images of the normal staining of the oesophagus, stomach, duodenum, ileum, colon, pancreas, lung and kidney are shown in FIG. 10.

TABLE 1

Binding of FG27 to normal human tissues as assessed by immunohistochemistry (IHC). Staining of these tissue microarrays (TMAs) were analysed via new viewer software 2010 and given a semi-quantitative score according to intensity of staining of tumour tissue. Strong staining was given a score of 3, moderate staining a score of 2, weak staining a score of 1 and a negative score of 0. The results also demonstrate differential staining of specific cell types within these tissues.

| Tissue type | 692/29 ($Le^{y/b}$) | BR96 ($Le^{y/x}$) | FG27 ($Le^y$) |
|---|---|---|---|
| Placenta | 0 | 2 | 0 |
| Oesophagus | 0 | 3 | 0 |
| Rectum | 0 | 1 | 0 |
| Gallbladder | 1 | 2 | 0 |
| Skin | 0 | 0 | 0 |
| Adipose | 0 | 0 | 0 |
| Heart | 0 | 0 | 0 |
| Skeletal | 0 | 0 | 0 |

TABLE 1-continued

Binding of FG27 to normal human tissues as assessed by
immunohistochemistry (IHC). Staining of these tissue microarrays (TMAs) were analysed
via new viewer software 2010 and given a semi-quantitative score according to intensity
of staining of tumour tissue. Strong staining was given a score of 3, moderate
staining a score of 2, weak staining a score of 1 and a negative score of 0. The results
also demonstrate differential staining of specific cell types within these tissues.

| Tissue type | 692/29 (Le$^{y/b}$) | BR96 (Le$^{y/x}$) | FG27 (Le$^{y}$) |
|---|---|---|---|
| Bladder | 0 | 0 | 0 |
| Ileum | 2 | 3 | 0 |
| Spleen | 0 | 0 | 0 |
| Brain | 0 | 0 | 0 |
| Jejunum | 3 | 3 | 0 |
| Stomach | 2 | 3 | 0/2 |
| Breast | 0 | 3 | 0 |
| Kidney | 0 | 1 | 0 |
| Testis | 0 | 0 | 0 |
| Cerebellum | 0 | 0 | 0 |
| Liver | 0 | 0 | 0 |
| Thymus | 1 | 0 | 0 |
| Cervix | 0 | 0 | 0 |
| Lung | 1 | 3 | 0/1 |
| Smooth Muscle | 0 | 0 | 0 |
| Colon | 1 | 1 | 0 |
| Ovary | 0 | 0 | 0 |
| Tonsil | 2 | 3 | 0/1 |
| Diaphram | 0 | 0 | 0 |
| Pancreas | 1 | 3 | 0/2 |
| Uterus | 0 | 0 | 0 |
| Duodenum | 1 | 3 | 0/2 |
| Thyroid | 0 | 0 | 0 |

To determine the therapeutic value of FG27, it was screened on human gastric, colorectal, ovarian and breast TMAs by IHC. It stained 80% of gastric (69/86), 100% of colorectal (55/55), 95% of ovarian (36/38) and 85% of breast (39/46) tumour tissues stained at differing intensities (Table 2).

of gastro-oesophageal joining regions tumours stained but 37% of these stained strongly. 46% of tumours in the lower one third of the oesophagus stained with FG27 with 53% of them staining strongly.

Due to cross-reactivity of FG27 with ovarian cancer cell lines, it was screened against an ovarian cancer TMA with

TABLE 2

Binding of FG27 mAb to human gastric, colorectal, ovarian and breast
tumour tissues as assessed by immunohistochemistry. Staining of these tissue
microarrays were analysed via new viewer software 2010 and given a semi-quantitative
score according to intensity of staining of tumour tissue. Strong staining was given a score
of 3, moderate staining a score of 2, weak staining a score of 1 and a negative score of 0.
Frequency and intensity of Lewis$^{y}$ expression on human tumour types

| Tumour type | No | Total positive | Immunohistochemistry (IHC) scores of Lewis$^{y}$ | | |
|---|---|---|---|---|---|
| | | | 3+ | 2+ | 1+ |
| Gastric | 86 | 69 | 19 | 25 | 25 |
| Colorectal | 55 | 55 | 29 | 18 | 8 |
| Ovarian | 38 | 36 | 2 | 18 | 16 |
| Breast | 46 | 39 | 7 | 13 | 19 |

Scoring showed that FG27 bound widely to gastric tumours with positive staining in 59% of tumours and 18% of tumours staining strongly. 19% of tumours stained moderately and 22% stained weakly. Results show that FG27 has the potential to target a wide range of gastric tumours and bind strongly to 18% of them. Kaplan Meier analysis revealed no association between expression of FG27 antigens and survival (data not shown). However, there was a correlation between FG27 antigen expression and M30 (apoptotic marker) expression (Pearson's chi-squared p=0.049). There was also a correlation between FG27 antigen expression and tumour site (Pearson's chi-squared p=0.008) with 65% of stomach specific tumours staining with FG27 with 26% staining strongly. In contrast, only 53%

360 tumours by immunohistochemistry. Scoring showed that FG27.18 bound poorly to ovarian tumours with 85% of tumours staining negatively. Only 15% of tumours stained positively and only 3% stained strongly. 3% of tumours stained moderately and 9% stained weakly.

Kaplan Meier survival analysis showed that patients whose tumours expressed FG27 antigen had a significantly (log rank p=0.049) better survival than those with no expression. There was a correlation between FG27 antigen expression and FIGO stage (Pearson's chi-squared p=0.024). There was also correlation between FG27 antigen expression and types of ovarian cancer (Pearson's chi-squared p=0.024) with over a third of mucinous and endometriod tumours expressing FG27 whereas less than 14% of serous, clear cells and undifferentiated tumours stained with this mAb. Cox multivariate analysis showed that FG27 did not confer any further prognostic value over FIGO stage, residual disease and response to chemotherapy.

TABLE 3

Comparison of staining tumours with the Lewis
y specifc mab FG27 with other Lewisy cross
reactive mabs BR96 (Lewisy/x) and 692/29 (lewisy/b).

| A) FG27.10 VS 692/29 on human tumour microarrays | | | | |
|---|---|---|---|---|
| Tumour type | No. | Both positive | Both negative | FG27.10 only | 692/29 only |
| Breast | 41 | 21 (51%) | 4 (10%) | 16 (39%) | 0 (0%) |
| Ovarian | 38 | 21 (55%) | 1 (3%) | 15 (39%) | 1 (3%) |
| Gastric | 72 | 59 (82%) | 3 (4%) | 2 (3%) | 8 (11%) |
| Colorectal | 52 | 43 (83%) | 0 (0%) | 9 (17%) | 0 (0%) |

| b) FG2.10 VS BR96 on human tumour microarrays | | | | |
|---|---|---|---|---|
| Tumour type | No. | Both positive | Both negative | FG27.10 only | BR96 only |
| Breast | 40 | 19 (48%) | 3 (8%) | 17 (43%) | 1 (3%) |
| Ovarian | 40 | 19 (48%) | 2 (5%) | 19 (48%) | 0 (0%) |
| Gastric | 62 | 43 (69%) | 6 (10%) | 4 (6%) | 9 (15%) |
| Colorectal | 51 | 38 (75%) | 0 (0%) | 13 (25%) | 0 (0%) |

The monospecific Lewis y mab, FG27.10, stained 3-39% more tumours then the Lewis y/b 692/29 mab and 6-48% more tumours than the Lewis y/x Br96 mab, reflecting its unique specificity. The greatest variation was seen on the ovarian and breast tumours.

Unlike FG27, which only demonstrated moderate binding to normal stomach, pancreas and duodenum in one of two samples, and weak binding to lung and tonsil in one of two samples, BR96 demonstrated strong binding to a number of tissues including oesophagus, ileum, jejunum, stomach, breast, lung, tonsil, pancreas and duodenum. BR96 also demonstrated moderate binding to the placenta and gallbladder, and weak binding to the rectum, kidney and colon. In comparison, 692/29 bound the jejunum strongly, the ileum, stomach and tonsil moderately, and the gallbladder, thymus, lung, colon, pancreas and duodenum weakly (Table 1). This limited normal binding profile of FG27, particularly in regard to the gastro-intestinal tissues, did not diminish the binding of the antibody to tumour tissues with 80% of gastric and 100% of colorectal tumour tissues demonstrating antigen expression. In comparison, 692/29 and BR96 displayed a good distribution on colorectal tumours binding 82% and 90% respectively (Noble, Spendlove et al. 2013), a similar figure for the later, 15/18 samples i.e. 83% also being reported in U.S. Pat. No. 5,491,088. 39% and 49% of these tumours stained moderately or strongly compared to 85% for FG27. 2-25 LE showed a poorer distribution, binding only 52% of colorectal tumours with 19% staining moderately and none staining strongly (Noble, Spendlove et al. 2013).

It is therefore demonstrated the FG27 has a significantly better normal binding profile, particularly in regard to the gastro-intestinal tissues, and the differential binding between each of Le$^y$ mAbs indicates the distinct nature of the invention.

Example 4—In Vivo Anti-Tumour Activity of FG27 in an Established Colorectal Metastatic Xenograft Model Comparison of the therapeutic effect of the mAb FG27 in the C170HM2 DLuX human hepatic metastasis model: The mouse C170HM2 DLuX human hepatic metastasis tumour model was used to investigate the anti-tumour activity of the murine FG27 mAb. The C170HM2 DLuX cell line is a bioluminescent variant of a liver metastasising colon tumour cell line passaged to invade the liver parenchyma when implanted into the peritoneal cavity and left 10 days to mestatasise to the live before mAb treatment was started. Growth and distribution/location of such labelled cells and tissue can be assessed non-invasively in real time and in excised tissue at post mortem (PM) in a suitable optical imaging system.

Anti-tumour data: FG27 administered twice a weekly (100 μg i.v.) reduced peritoneal cavity and associated tumour growth compared to the vehicle control as assessed by bioluminescent intensity (FIG. 11a). The study was terminated on day 32. Treatment with FG27 resulted in a significant reduction in bioluminescent tumour burden by the last day of the study compared to the vehicle control (p=0.014). There was a significant reduction in injection site tumour growth with FG27 treatment (p=0.05; FIG. 11b).

In a second in vivo study extending the duration of treatment, FG27 demonstrated a significant reduction in percentage tumour growth by day 51 (p=0.019) compared to the treatment control group (FIG. 12a). Analysis by Log Rank Mantel-Cox test demonstrates significant enhanced survival in the FG27 (p=0.0251) treatment group compared to the vehicle only control (FIG. 12b).

Example 5—Chimeric mAb

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody. Chimeric (or humanised) antibodies of the present invention can be prepared based on the sequence of a murine mAb prepared as described above. When the gene and amino acid sequence of the antibodies was analysed it showed that FG27.10 (FIG. 1) and FG27.18 (FIG. 2) had identical variable regions but different constant regions IgG3 and IgG1 respectively. This suggested that a single B cell had subclass switched and then expanded during the immunisation protocol and that both of these clones were successfully fused.

Compared to the closest germline sequences, FG27 contains 7 mutations in its heavy chain (all non-silent) and 3 mutations in its light chain (all non-silent). 4 amino acid differences to the germline are in the heavy chain CDRs and 3 in FR3. In the CDR1, there is an amino acid change from D to H at position 36. In the CDR2, the amino acid changes are a G to D at positions 59 and 63 and at position 64, S to N (FIG. 2a). For the light chain, there are 2 amino acid differences in the CDR1 germline, S to I at position 28 and S to T at position 32, and 1 in the FR2, K51N which is unique.

There are several other mabs that bind Lewis$^y$ but cross react with other related Lewis antigens. FG27.10/18 are the only antibodies with monospecificity for just Lewis y. This is reflected in the similar but distinct sequence of the FG27 variable heavy and light chain regions (FIG. 13*a,b*). FG27 shows 16-68% differences in the amino acid sequences CDRs within the heavy chain, 4.3-16% differences in amino acid differences in the CDR sequence in the light chain, 8.6-49.5% differences in amino acid sequence in the variable region of the heavy chain, 2-24% differences in amino acid sequence in the variable region of the light chain from the other cross reactive lewis y mabs (Table 4). The most variation is within CDRH2 with 3-5 of the 8 amino acids varying between the different mabs.

killing of a range of antigen positive (AGS, Colo201, C170, C170HM, MCF-7, OVCAR4) cell lines with the two mAbs showing variable amounts of killing. Neither mAb showed killing of the antigen negative cell lines (LoVo, MKN45, 791T, SKOV3).

FIG. 15*c* shows PI uptake in the colorectal cell line C170 by a range of mAbs. FG27.10 and the positive control antibody SC101 showed strong titratable killing. FG27.18

TABLE 4

Differences in amino acid sequences in the variable heavy and light regions of FG27 from anti-lewis y cross reactive mabs.

| mab | FR1 | CDRH1 | FR2 | CDRH2 | FR3 | CDRH3 | TOTAL | TOTAL CDRs Diff fg27 | TOTAL Diff fg27 |
|---|---|---|---|---|---|---|---|---|---|
| | 25 | 8 | 17 | 8 | 38 | 9 | 105 | 25 | |
| FG27 | 0 | 1 | 0 | 3 | 3 | ARGKYDGAW | 6.7 | — | |
| S56976 | 0 | 0 | 1 | 3 | 0 | same | 3.8 | 16 | 8.6 |
| H18A | 3 | 0 | 1 | 3 | 1 | same | 7.6 | 16 | 11 |
| BR96 | 1 | 0 | 0 | 3 | 0 | 2 | 2.9 | 20 | 8.6 |
| PASTAN B3 | 1 | 0 | 3 | 4 | 5 | 4 | 12.4 | 32 | 11.4 |
| HU38193 | 1 | 0 | 3 | 5 | 10 | 4 | 18.1 | 32 | 19 |
| SC101 | 13 | 5 | 8 | 3 | 23 | 9 | 49.5 | 68 | 49.5 |

| mab | FR1 | CDRL1 | FR2 | CDRL2 | FR3 | CDRL3 | TOTAL | TOTAL CDRs Diff fg27 | TOTAL Diff fg27 |
|---|---|---|---|---|---|---|---|---|---|
| | 26 | 11 | 17 | 3 | 36 | 9 | 102 | 23 | |
| FG27 | 0 | 0 | 2 | 1 | 0 | 0 | 3 | — | |
| S56976 | | | | | | | | | |
| H18A | 1 | 1 | 2 | 0 | 0 | 0 | 4 | 8.7 | 3 |
| BR96 | 2 | 2 | 1 | 0 | 0 | 0 | 5 | 4.3 | 4 |
| PASTAN B3 | 0 | 1 | 0 | 0 | 0 | 0 | 1 | 4.3 | 2 |
| HU38193 | 9 | 1 | 4 | 0 | 10 | 0 | 24 | 8.7 | 24 |
| SC101 | 1 | 0 | 0 | 1 | 0 | 0 | 2 | 16 | 6 |

FG27.18 heavy and light chain variable regions were cloned into human IgG1 and IgG2 expression vectors. This was transfected into CHO-S cells and human antibody purified on protein G. The chimeric mAbs bound to Le$^y$ expressing tumour cell lines, including the gastric cell line, AGS (FIG. 14).

Example 6—Direct Cell Killing

A number of anti-glycan mAbs have been shown to induce direct cell death in antigen positive cell lines with no need for effector cells or complement. This can potentially enhance their in vivo efficacy as tumours can develop mechanisms to avoid immune-mediated cell death. This capability is mainly associated with glycan-binding mAbs of the mIgG3 isotype, hence the property is lost upon chimerisation or humanisation.

In order to determine whether FG27.10 and FG27.18 have the ability to cause direct cell death, ST16 cells were incubated with FG27.10, FG27.18 and the anti-sialyl Le$^a$ mAb SC104 for 2 hrs at RT, before cell death was measured by the uptake of propidium iodide, which is a DNA inter-cellating agent that is only taken up by dying cells (FIG. 15*a*). Interestingly, despite having the same variable region, only FG27.10 was able to induce direct cell death, with no uptake of PI observed with FG27.18. FIG. 15*b* shows direct showed weak non titratable killing. The human IgG1 chimeric showed moderate titratable killing whereas the IgG2 variant did not.

Example 6—Internalisation

FG27.10, FG27.18 and CH27 were all assessed for internalisation using a variety of tumour cell lines (FIG. 16). FG27.18 demonstrated dose-dependent internalisation on most cell lines tested with decreases in cell viability ranging from 60% (C170) up to 75% (MCF7) and 85% (AGS) at the highest concentration tested. FG27.10 showed best internalisation on AGS (up to 50% decrease in viability) and MCF7 (up to 70% decrease in viability). Internalisation on the H322 cell line was more variable for both the murine mAbs. The CH27 mAb was efficiently internalised by MCF7, with up to a 75% reduction in cell viability being observed, and by H322 with a ~40% reduction in cell viability.

Example 7—In Vitro Anti-Tumour Activity of FG27

ADCC and CDC: The ability of murine and chimeric FG27 mAbs to induce tumour cell death through ADCC was screened. Human PBMCs were used as the source of effector cells while a panel of tumour cells served as target cells. Initially ADCC analysis was undertaken with FG27.10 IgG3 supernatant (FIG. 17*a*). The extent of ADCC seen corresponded to expression of the Lewis Y antigen and was therefore seen for ST16 and OVCAR3 with only low levels being observed with C170s and background alone for LoVo, HT29 or Colo201 (FIG. 17*a*). The extent of ADCC MCF7 and OVCAR3 target cell killing by murine FG27.10 (mIgG3), FG27.18 (mIgG1), CH27 IgG1 and IgG2 was measured and compared after 18 hrs incubation at 37° C.; the CH27 IgG1 gave the highest level of killing of the cell lines, MCF7 and OVCAR3 (FIG. 17*b*).

CDC is known to be an important mechanism involved in eliminating tumour cells in vivo. The capacity of ST16 cells to be killed by CDC induced by the mAbs FG27.10, FG27.18, CH27 IgG1 and CH27 IgG2 in the presence or absence of human serum as source of complement at 37° C. for 18 hrs was assayed. As shown in FIG. 17*c*, of the FG27 mAbs, FG27.10 (mIgG3) gave the highest level of killing at 3 μg/ml whereas nonsignificant levels were seen for the CH27 IgG2 which, given the nature of IgG2 antibodies, was as expected. Likewise, FG27.10 gave the highest level of killing, followed by the CH27 IgG1 when AGS cells were used. Again no killing was seen with the CH27 IgG2 (FIG. 17*d*).

In summary, the FG27 mAbs strongly induced ADCC using human PBMCs as effector cells as well as significant CDC with human serum as a complement source.

Example 9—Generation of a Humanised Version of the FG27 Antibody

Human VH and VK cDNA Databases

The protein sequences of human and mouse immunoglobulins from the International Immunogenetics Database 2009 (Lefranc 307-10) and the Kabat Database Release 5 of Sequences of Proteins of Immunological interest (last update 17 Nov. 1999) (Kabat et al. 1-3242) were used to compile a database of human immunoglobulin sequences in Kabat alignment. Our database contains 10,906 VH and 2,912 VK sequences.

FG27 Human Framework Selection

Humanisation requires the identification of suitable human V regions. The sequence analysis program, Gibbs, was used to interrogate the human VH and VK databases with FG27 VH and VK protein sequences using various selection criteria. Using the program Discovery Studio (Accelrys), FW residues within 4 Å of the CDR residues (Kabat definition) in the structures of mouse FG27 antibody were identified, and designated as the "4 Å Proximity Residues". Human VH sequences with highest identity to FG27 VH in the 4 Å Proximity Residues are shown in FIG. 19, together with a list of these envelope residues and VCIs, and the number of residues in either the FW, VCI or 4 Å Proximity Residues which are identical to the mouse equivalent position. FIG. 18 shows the alignment and residue identity of all the VH sequences in FIG. 19. The number of apparent somatic mutations in each FW, identified by comparison with the most identical human germline V gene, is indicated in FIG. 20.

Humanised sequences, murine and incomplete sequences were removed from the analysis. The sequence AJ579110 was chosen as the human donor candidate due to its higher sequence identity and similarity. It has no somatic mutations from its germline ABO19439 or HM855436

Design of FG27 RHA and FG27 RHB

As a suitable human framework has been identified, the synthetic protein and DNA sequence can be designed. The initial design of the humanised version of FG27 is the grafting of CDR 1, 2 and 3 from FG27 VH into the acceptor FW of AJ579110. One VCI+4 Å Proximity Residue, at Kabat position 24 is not conserved in FG27 RHA, and this is back-mutated to the mouse equivalent residue to produce the humanised version FG27 RHB FIG. 21 compares the murine and the humanised versions of FG27 VH protein sequences.

FG27 RKA Framework Selection

In order to humanise the light chain a human kappa chain was identified in a similar process to that of the heavy chain. FIG. 22,23 show 4 Å Proximity Residues and the number of residues, in the FW or the 4 Å Proximity Residues, which are identical to the mouse equivalent position, alignment of VK sequences and comparison to human germline. Initial analysis found several potential donor candidates, but all these proved to be Human VK4 which show poor expression. Extending the analysis to include CDR1 with one less residue resulted in a single candidate, X72449, which showed a higher degree of sequence homology to the murine antibody than the VK4 candidates. This candidate has a single somatic mutation from the human VK2 germline, but no somatic mutations from the human VK2D germline (FIG. 24).

Design of FG27 RKA and FG27 RKB

The framework from X72449 was used to design the DNA and protein for the humanised constructs. CDR 1, 2 and 3 from FG27 VK are shown grafted into the acceptor FW of X72449 to generate the initial version of humanised FG27. There is a single unmatched 4 Å Proximity residue, 5, in FG27 RKA that was back-mutated to the equivalent mouse residue in variant FG27 RKB (FIG. 25).

Generation and Properties of a Humanised Version of FG27

Generation of FG27 Humanised Antibodies

The genes for FG27 RHA and FG27 RKC were synthesized by Genewiz and codon optimised for human sequences (FIG. 3*ab*). The natural human framework sequences M65092 and X72449, heavy and light chains, respectively, and the natural mouse CDR sequences were assembled in silico and designated FG27 RHA to FG27 RHB and FG27 RKA to FG27 RKD. Using software algorithms proprietary to Genewiz, the sequences were optimised by silent mutagenesis to use codons preferentially utilised by human cells and synthesized. RHA/B and RKA/B constructs were PCR amplified with specific primers to the expression vector+ insert (as described previously for the chimeric versions) and inserted into pHuG1 and pHuK in ligase independent cloning reactions and used to transform TOP10 bacteria. RKA and RHA were subsequently modified by PCR mutagenesis to obtain all human variants annotated in the FIGS. 21 and 25.

Clones were sequenced and expression plasmid DNA was prepared using the QIAGEN Plasmid Miniprep Kit or Qiagen Plasmid Maxiprep kit. The expression construct sequences (RHA, RHB, RKA and RKB) are shown in FIGS. 21 and 25. Expression plasmid preparations encoding (humanised or chimeric) VH and VK were used to transfect Expi293 cells, cultured for 10 days in serum free media, whereupon the conditioned medium containing secreted antibody was harvested.

Antibody Expression

The concentrations of IgG1κ antibodies in Expi293 cell conditioned media were measured by ELISA and are shown in Table 5. Most antibodies were produced at a satisfactory level, except for those highlighted in red.

TABLE 5

| IgG levels in transfected Expi293 cell conditioned medium | | |
|---|---|---|
| CONSTRUCTS USED | | IgG CONCENTRATION (ng/ml) IN |
| VK | VH | µg/mL |
| 1210VH | 1210VK ctrl | 256.39 |
| FG27 | FG27 | 20.19 |
| FG27 | FG27 | 112.34 |

Lewis Y-HSA Binding by FG27 Antibodies

Binding activity to the LewisY-HSA antigen was measured by Binding ELISA. Initial experiments showed there was essentially no difference between the binding potency of the mouse or chimeric antibodies. This result gives us some confidence in the success of the humanisation process.

The data shown in FIG. 26 show the binding potency of the initial versions of the humanised FG27. Although all versions bound to LewisY-HSA. Versions of the antibody consisting of RHA/RKB, RHA/RKC, RHA/RKD and RHB/RKC were chosen as possible lead candidates.

Thermo Stability of Humanised Candidate Antibodies to High Temperatures

The aim of this experiment is to compare the thermo stability of the humanised antibodies. When subjected to higher temperatures, varying from 30° to 85° C. for 10 mins, cooled to 4° C. and used in an ELISA assay at the EC80 concentration of each candidate. All the antibodies tested appear equally stable (FIG. 27), all becoming inactive at >72° C.

Determination of Humanised Candidate Antibodies Tm

In order to determine the melting temperature of the chimeric and humanised lead antibodies RHA/RKB, RHA/RKC, RHA/RKD and RHB/RKC all antibodies were purified in a 2-step affinity chromatography and gel filtration system and tested in a thermal shift assay. Samples were incubated with a fluorescent dye (Sypro Orange) for 71 cycles with 1° C. increase per cycle in a qPCR thermal cycler. Tm for the chimeric and the four humanised antibodies are indicated in FIG. 28. All of the candidate antibodies and the chimeric antibody have the same Tm's (72° C.).

Affinity of Humanised Candidate Antibodies

Antibody affinity determination using SPR analysis was carried out using a Biacore T3000. Lewis Y-HSA was covalently immobilised to a CM5 chip (Cat: BR-1005-30) in accordance with the manufacturer's instructions. Chimeric FG27, RHA/RKB, RHA/RKC, RHA/RKD and RHB/RKC antibodies were diluted in buffer in concentrations ranging from 200 nM to 0.274 nM (serial 3-fold dilutions) and then injected at a flow rate of 50 µl/min. Association time was set at 120 secs and disassociation time 600 secs.

The kinetics of binding/dissociation was analysed according to the best fit to heterogenous ligand model using BIAcore 3000 evaluation software package. An overlay of the 200 nM binding curves is shown in the sensogram (FIG. 29). RHA/RKB, RHA/RKC, and RHB/RKC show similar affinities to chimeric FG27 (RHA/RKB>RHA/RKC>RHB/RKC>>RHA/RKD). These results suggest that the humanisation has successfully retained the binding activity within the desired parameters and RHA/RKB or RHA/RKC have the highest affinities.

Aggregation of Humanised Candidate Antibodies

Samples were injected at 0.4 ml/min into a size exclusion column in an HPLC system and analyzed by multi-angle light scattering to determine the absolute molar masses and check for aggregation. All variants show no signs of aggregation with an average molecular weight ranging of 140.19 kDa, which is the expected range for an IgG monomer in this analysis setup. All samples are monodispersed (Mw/Mn<1.05). The mass recoveries (calculated mass over injected mass) are 100% which indicates good protein recovery and that the samples do not seem to stick to the column or contain insoluble aggregates, which would be retained by the guard column. Overall the data suggest there are no aggregation concerns in any of the anti-FG27 antibody samples analysed.

Non-specific Protein-Protein Interactions (CIC)

Cross-Interaction Chromatography using bulk purified human polyclonal IgG is a technique for monitoring non-specific protein-protein interactions, and can be used to discriminate between soluble and insoluble antibodies. An elevated Retention Index (k') indicates a self-interaction propencity and a low solubility. RHA/RKB, RHA/RKC, RHB/RKC antibodies shows a Retention Index below 0.044, indicating a low propensity for non-specific interactions and good solubility (FIG. 30).

The antibody has been engineered and expressed as a fully humanised antibody without losing Lewis Y HSA binding potency (FIGS. 26 and 29). Experiments with chimeric antibodies, consisting of murine variable regions on human constant regions, showed a similar potency in a Lewis Y HSA binding ELISA to that of the murine antibody. This result lends some confidence in a positive outcome for the humanisation process.

The initial experiments showed that the fully humanised heavy and light chains, i.e. without framework mutations to introduce murine 4 A proximity residues, does not bind the Lewis Y HSA peptide as well as the chimeric positive control antibody but the versions with a single back mutation bind on a par with the chimeric positive control. Assays measuring antibody solubility, thermostability and aggregation suggest all the humanised candidates have acceptable biophysical characteristics.

In our view the combination of the excellent binding, expression, thermostability, affinity and cell binding makes RHA heavy chain version, in conjunction with the RKC light chain version the best candidate antibody for further development.

Example 10-FG27 Binding Studies

The humanised (humanized 27) and chimeric mAbs (CH27) demonstrated a similar cell binding pattern on titration on cancer cell lines (FIG. 31). Equilibrium affinity constants are overall on the same order, but slightly higher compared to the parental murine antibodies, whereas the maximum binding capacity of the humanised 27 and CH27 are larger compared to those of the murine mAbs. This result suggests a successful outcome of the humanization process.

Example 11—Direct Killing of the Humanised mab

In order to enhance the direct cell killing of the human IgG1 27 chimeric (27hIgG1), we transferred selected mIgG3 constant region residues into the hIgG1 Fc domain thereby creating an improved 'i27G1' LewisY glycan binding mAb with improved in vitro direct cell killing ability. FIG. 33 shows the amino acid and nucleic acid sequences of the respective light and heavy chains of the 'i27G1' antibody. This antibody forms another aspect of the invention.

FIG. 32 shows direct cell killing, functional affinity as well as effector functions of the improved i27G1. The mIgG3 27 antibody has direct cell killing ability on the Lewis$^y$-expressing AGS (i) and MCF7 cell lines (ii) whereas the chimeric 27hIgG1 does not. Our i27G1, containing selected mIgG3 constant region residues, displays significantly improved direct cell killing, compared to 27hIgG1, equivalent to the 27mG3 mAb, on both AGS (i) and MCF7 (ii). Additionally, 127G1 exhibits significantly improved functional Lewis$^y$ affinity compared to the 27hIgG1 (iii). Importantly, the effector functions of i27G1, ADCC as well as CDC, were both equivalent to those of 27hIgG1, on MCF7 (iv and v). Collectively the results indicate that transfer of selected regions from the mIgG3 constant region into the 27hIgG1 backbone created a hybrid mAb with direct cell killing ability, increased functional affinity as well as robust immune effector functions.

REFERENCES

Altschul, S. F., W. Gish, W. Miller, E. W. Myers and D. J. Lipman (1990). "Basic local alignment search tool." *J Mol Biol* 215(3): 403-410.

Altschul, S. F., T. L. Madden, A. A. Schaffer, J. Zhang, Z. Zhang, W. Miller and D. J. Lipman (1997). "Gapped BLAST and PSI-BLAST: a new generation of protein database search programs." *Nucleic Acids Res* 25(17): 3389-3402.

Alvarez-Rueda, N., S. Leprieur, B. Clemenceau, S. Supiot, V. Sebille-Rivain, A. Faivre-Chauvet, F. Davodeau, F. Paris, J. Barbet, J. Aubry and S. Birkle (2007). "Binding activities and antitumor properties of a new mouse/human chimeric antibody specific for GD2 ganglioside antigen." *Clin Cancer Res* 13(18 Pt 2): 5613s-5620s.

Ausubel, F. (1992). *Short protocols in molecular biology*, John Wiley & Sons.

Barbas, C. F., 3rd, D. Hu, N. Dunlop, L. Sawyer, D. Cababa, R. M. Hendry, P. L. Nara and D. R.

Azinovic, I., G. L. DeNardo, K. R. Lamborn, G. Mirick, D. Goldstein, B. M. Bradt, and S. J. DeNardo. 2006. 'Survival benefit associated with human anti-mouse antibody (HAMA) in patients with B-cell malignancies', Cancer *Immunol Immunother*, 55:1451-8.

Burton (1994). "In vitro evolution of a neutralizing human antibody to human immunodeficiency virus type 1 to enhance affinity and broaden strain cross-reactivity." *Proc Natl Acad Sci USA* 91(9): 3809-3813.

Bird, R. E., K. D. Hardman, J. W. Jacobson, S. Johnson, B. M. Kaufman, S. M. Lee, T. Lee, S. H. Pope, G. S. Riordan and M. Whitlow (1988). "Single-chain antigen-binding proteins." *Science* 242(4877): 423-426.

Bodanzsky, M. and A. Bodanzsky (1984). *The practice of peptide synthesis. New York*, Springer Verlag.

Chou, H. H., H. Takematsu, S. Diaz, J. Iber, E. Nickerson, K. L. Wright, E. A. Muchmore, D. L. Nelson, S. T. Warren and A. Varki (1998). "A mutation in human CMP-sialic acid hydroxylase occurred after the Homo-Pan divergence." *Proc Natl Acad Sci USA* 95(20): 11751-11756.

D'Arcy, C. A., and M. Mannik. 2001. 'Serum sickness secondary to treatment with the murine-human chimeric antibody IDEC-C2B8 (rituximab)', *Arthritis Rheum*, 44:1717-8.

Durrant, L. G., P. Noble and I. Spendlove (2012). "Immunology in the clinic review series; focus on cancer: glycolipids as targets for tumour immunotherapy." *Clin Exp Immunol* 167(2): 206-215.

Eppstein, D. A., Y. V. Marsh, M. van der Pas, P. L. Felgner and A. B. Schreiber (1985). "Biological activity of liposome-encapsulated murine interferon gamma is mediated by a cell membrane receptor." *Proc Natl Acad Sci USA* 82(11): 3688-3692.

Furukawa, K., S. Welt, B. W. Yin, H. J. Feickert, T. Takahashi, R. Ueda and K. O. Lloyd (1990). "Analysis of the fine specificities of 11 mouse monoclonal antibodies reactive with type 2 blood group determinants." *Mol Immunol* 27(8): 723-732.

Gram, H., L. A. Marconi, C. F. Barbas, 3rd, T. A. Collet, R. A. Lerner and A. S. Kang (1992). "In vitro selection and affinity maturation of antibodies from a naive combinatorial immunoglobulin library." *Proc Natl Acad Sci USA* 89(8): 3576-3580.

Hellstrom, I., H. J. Garrigues, U. Garrigues and K. E. Hellstrom (1990). "Highly tumor-reactive, internalizing, mouse monoclonal antibodies to Le (y)-related cell surface antigens." *Cancer Res* 50(7): 2183-2190.

Holliger, P., T. Prospero and G. Winter (1993). "Diabodies": small bivalent and bispecific antibody fragments." *Proc Natl Acad Sci USA* 90(14): 6444-6448.

Holliger, P. and G. Winter (1993). "Engineering bispecific antibodies." *Curr Opin Biotechnol* 4(4): 446-449.

Huston, J. S., D. Levinson, M. Mudgett-Hunter, M. S. Tai, J. Novotny, M. N. Margolies, R. J. Ridge, R. E. Bruccoleri, E. Haber, R. Crea and et al. (1988). "Protein engineering of antibody binding sites: recovery of specific activity in an anti-digoxin single-chain Fv analogue produced in *Escherichia coli.*" *Proc Natl Acad Sci USA* 85(16): 5879-5883.

Hwang, K. J., K. F. Luk and P. L. Beaumier (1980). "Hepatic uptake and degradation of unilamellar sphingomyelin/cholesterol liposomes: a kinetic study." *Proc Natl Acad Sci USA* 77(7): 4030-4034. Jespers, L. S., A. Roberts, S. M. Mahler, G. Winter and H. R. Hoogenboom (1994). "Guiding the selection of human antibodies from phage display repertoires to a single epitope of an antigen." *Biotechnology* (N Y) 12(9): 899-903.

Jones, S. T. and M. M. Bendig (1991). "Rapid PCR-cloning of full-length mouse immunoglobulin variable regions." *Biotechnology* (N Y) 9(1): 88-89.

Karlin, S. and S. F. Altschul (1990). "Methods for assessing the statistical significance of molecular sequence features by using general scoring schemes." *Proc Natl Acad Sci USA* 87(6): 2264-2268.

Karlin, S. and S. F. Altschul (1993). "Applications and statistics for multiple high-scoring segments in molecular sequences." *Proc Natl Acad Sci USA* 90(12): 5873-5877.

Kitamura, K., E. Stockert, P. Garin-Chesa, S. Welt, K. O. Lloyd, K. L. Armour, T. P. Wallace, W. J. Harris, F. J. Carr and L. J. Old (1994). "Specificity analysis of blood group Lewis-y (Le (y)) antibodies generated against synthetic and natural Le (y) determinants." *Proc Natl Acad Sci USA* 91(26): 12957-12961.

Lefranc, M. P., V. Giudicelli, C. Ginestoux, J. Jabado-Michaloud, G. Folch, F. Bellahcene, Y. Wu, E. Gemrot, X. Brochet, J. Lane, L. Regnier, F. Ehrenmann, G. Lefranc and P. Duroux (2009). "IMGT, the international ImMunoGeneTics information system." *Nucleic Acids Res* 37 (Database issue): D1006-1012.

Loo, D., N. Pryer, P. Young, T. Liang, S. Coberly, K. L. King, K. Kang, P. Roberts, M. Tsao, X. Xu, B. Potts and J. P. Mather (2007). "The glycotope-specific RAV12 monoclonal antibody induces oncosis in vitro and has antitumor activity against gastrointestinal adenocarcinoma tumor xenografts in vivo." *Mol Cancer Ther* 6(3): 856-865.

Marks, J. D., A. D. Griffiths, M. Malmqvist, T. P. Clackson, J. M. Bye and G. Winter (1992). "By-passing immunization: building high affinity human antibodies by chain shuffling." Biotechnology (N Y) 10(7): 779-783.

Miotti, S., D. R. Negri, O. Valota, M. Calabrese, R. L. Bolhuis, J. W. Gratama, M. I. Colnaghi, and S. Canevari. 1999. 'Level of anti-mouse-antibody response induced by bi-specific monoclonal antibody OC/TR in ovarian-carcinoma patients is associated with longer survival', Int J Cancer, 84:62-8.

Myers, E. W. and W. Miller (1989). "Approximate matching of regular expressions." Bull Math Biol 51(1): 5-37.

Noble, P., I. Spendlove, S. Harding, T. Parsons and L. G. Durrant (2013). "Therapeutic targeting of Lewis (y) and Lewis (b) with a novel monoclonal antibody 692/29." PLOS One 8(2): e54892.

Pai, L. H., R. Wittes, A. Setser, M. C. Willingham and I. Pastan (1996). "Treatment of advanced solid tumors with immunotoxin LMB-1: an antibody linked to Pseudomonas exotoxin." Nat Med 2(3): 350-353.

Pearson, W. R. and D. J. Lipman (1988). "Improved tools for biological sequence comparison."Proc Natl Acad Sci USA 85(8): 2444-2448.

Pluckthun, A. (1991). "Antibody engineering: advances from the use of Escherichia coli expression systems." Biotechnology (N Y) 9(6): 545-551.

Rabu, C., R. McIntosh, Z. Jurasova and L. Durrant (2012). "Glycans as targets for therapeutic antitumor antibodies." Future Oncol 8(8): 943-960.

Reff, M. E. (1993). "High-level production of recombinant immunoglobulins in mammalian cells."Curr Opin Biotechnol 4(5): 573-576.

Remington, R. (1980). Remington's pharmaceutical sciences, Mack Pub. Co.

Sambrook, J. (1989). Molecular cloning: A laboratory manual, Cold Spring Harbor Laboratory Press.

Sambrook, J. and D. Russell (2001). Molecular cloning: A laboratory manual. Cold Spring Harbor, N.Y., Cold Spring Harbor Laboratory Press.

Schier, R., A. McCall, G. P. Adams, K. W. Marshall, H. Merritt, M. Yim, R. S. Crawford, L. M. Weiner, C. Marks and J. D. Marks (1996). "Isolation of picomolar affinity anti-c-erbB-2 single-chain Fv by molecular evolution of the complementarity determining regions in the center of the antibody binding site." J Mol Biol 263(4): 551-567.

Schuster, M., P. Umana, C. Ferrara, P. Brunker, C. Gerdes, G. Waxenecker, S. Wiederkum, C. Schwager, H. Loibner, G. Himmler and G. C. Mudde (2005). "Improved effector functions of a therapeutic monoclonal Lewis Y-specific antibody by glycoform engineering." Cancer Res 65(17): 7934-7941.

Scott, A. M., D. Geleick, M. Rubira, K. Clarke, E. C. Nice, F. E. Smyth, E. Stockert, E. C. Richards, F. J. Carr, W. J. Harris, K. L. Armour, J. Rood, A. Kypridis, V. Kronina, R. Murphy, F. T. Lee, Z. Liu, K. Kitamura, G. Ritter, K. Laughton, E. Hoffman, A. W. Burgess and L. J. Old (2000). "Construction, production, and characterization of humanized anti-Lewis Y monoclonal antibody 3S193 for targeted immunotherapy of solid tumors." Cancer Res 60(12): 3254-3261.

Sidman, K. R., W. D. Steber, A. D. Schwope and G. R. Schnaper (1983). "Controlled release of macromolecules and pharmaceuticals from synthetic polypeptides based on glutamic acid." Biopolymers 22(1): 547-556.

Schroff, R. W., K. A. Foon, S. M. Beatty, R. K. Oldham, and A. C. Morgan, Jr. 1985. 'Human anti murine immunoglobulin responses in patients receiving monoclonal antibody therapy', Cancer Res, 45:879-85.

Soejima, M. and Y. Koda (2005). "Molecular mechanisms of Lewis antigen expression." Leg Med (Tokyo) 7(4): 266-269.

Stemmer, W. P. (1994). "Rapid evolution of a protein in vitro by DNA shuffling." Nature 370(6488): 389-391.

Stewart, J. and J. Young (1984). Solid phase peptide synthesis. Rockford, Illinois, Pierce Chemical Company.

Tolcher, A. W., S. Sugarman, K. A. Gelmon, R. Cohen, M. Saleh, C. Isaacs, L. Young, D. Healey, N. Onetto and W. Slichenmyer (1999). "Randomized phase II study of BR96-doxorubicin conjugate in patients with metastatic breast cancer." J Clin Oncol 17(2): 478-484.

Torelli, A. and C. A. Robotti (1994). "ADVANCE and ADAM: two algorithms for the analysis of global similarity between homologous informational sequences." Comput Appl Biosci 10(1): 3-5.

Traunecker, A., A. Lanzavecchia and K. Karjalainen (1991). "Bispecific single chain molecules (Janusins) target cytotoxic lymphocytes on HIV infected cells." EMBO J 10(12): 3655-3659.

Trill, J. J., A. R. Shatzman and S. Ganguly (1995). "Production of monoclonal antibodies in COS and CHO cells." Curr Opin Biotechnol 6(5): 553-560.

Ward, E. S., D. Gussow, A. D. Griffiths, P. T. Jones and G. Winter (1989). "Binding activities of a repertoire of single immunoglobulin variable domains secreted from Escherichia coli." Nature 341(6242): 544-546.

Yin, B. W., C. L. Finstad, K. Kitamura, M. G. Federici, M. Welshinger, V. Kudryashov, W. J. Hoskins, S. Welt and K. O. Lloyd (1996). "Serological and immunochemical analysis of Lewis y (Le$^y$) blood group antigen expression in epithelial ovarian cancer." Int J Cancer 65(4): 406-412.

Yuriev, E., W. Farrugia, A. M. Scott and P. A. Ramsland (2005). "Three-dimensional structures of carbohydrate determinants of Lewis system antigens: implications for effective antibody targeting of cancer." Immunol Cell Biol 83(6): 709-717.

Zhang, G., H. Zhang, Q. Wang, P. Lal, A. M. Carroll, M. de la Llera-Moya, X. Xu and M. I. Greene (2010). "Suppression of human prostate tumor growth by a unique prostate-specific monoclonal antibody F77 targeting a glycolipid marker." Proc Natl Acad Sci USA 107(2): 732-737.

Zhong, L. T., A. Manzi, E. Skowronski, L. Notterpek, A. L. Fluharty, K. F. Faull, I. Masada, S. Rabizadeh, M. Varsanyi-Nagy, Y. Ruan, J. D. Oh, L. L. Butcher and D. E. Bredesen (2001). "A monoclonal antibody that induces neuronal apoptosis binds a metastasis marker." Cancer Res 61(15): 5741-5748.

The invention claimed is:

1. An isolated antibody or antibody fragment that binds specifically to Fucal-2Galb1-4(Fucal-3)GlcNAc (Le$^y$), wherein the antibody or the antibody fragment comprises the following complementarity determining regions (CDRs):

CDRH1, CDRH2 and CDRH3 having the amino acid sequences GFTFSHYY (SEQ ID NO: 63), ISNDGDNT (SEQ ID NO: 64), and ARGKYDGAWFAY (SEQ ID NO: 65), respectively, and CDRL1, CDRL2 and CDRL3 having the amino acid sequences QIIVHTNGNTY (SEQ ID NO: 66), KVS (SEQ ID NO: 67), and FQGSHVPFT (SEQ ID NO: 68), respectively.

2. The antibody or antibody fragment of claim 1, comprising a VH having the amino acid sequence set forth in SEQ ID NO: 27 and a VL having the amino acid sequence set forth in SEQ ID NO: 36.

3. The antibody or antibody fragment of claim 1, wherein the CDRs are carried by a human antibody framework.

4. The antibody or antibody fragment of claim 1, further comprising a human constant region.

5. The antibody of claim 1, comprising a heavy chain having the amino acid sequence set forth in SEQ ID NO: 87 and a light chain amino acid sequence set forth in SEQ ID NO: 88.

6. The antibody of claim 1, comprising a heavy chain having the amino acid sequence set forth in SEQ ID NO: 89 and a light chain having the amino acid sequence set forth in SEQ ID NO: 90.

7. The antibody or antibody fragment of claim 1, which is attached to a chemotherapeutic or cytotoxic agent.

8. A pharmaceutical composition comprising an antibody or antibody fragment of claim 1 and a pharmaceutically acceptable excipient, diluent, carrier, buffer or stabiliser.

9. A method for treating a tumor in a subject in need thereof comprising administering an effective amount of the antibody or antibody fragment of claim 1.

10. The method of claim 9, further comprising administration of an active agent, wherein the antibody or the antibody fragment and the active agent are administered simultaneously, separately or sequentially.

11. The method of claim 9, wherein the tumor is a colorectal, gastric, pancreatic, lung, ovarian or breast tumor.

12. A nucleic acid the antibody or antibody fragment of claim 1.

13. An antibody or antibody fragment comprising a heavy chain having an amino acid sequence set forth in SEQ ID NO: 22 and a light chain having an amino acid sequence substantially as set forth in SEQ ID NO: 20.

14. The antibody or antibody fragment of claim 13 comprising a heavy chain encoded by the nucleic acid sequence set forth in SEQ ID NO: 21 and/or a light chain encoded by a nucleic acid sequence set forth in SEQ ID NO: 19.

15. The method of claim 9, wherein the tumor is a colorectal, gastric, pancreatic, lung, ovarian or breast tumor.

* * * * *